US012708608B2

(12) United States Patent
Goldman et al.

(10) Patent No.: US 12,708,608 B2
(45) Date of Patent: Aug. 18, 2026

(54) METHODS OF TREATING SCHIZOPHRENIA AND OTHER NEUROPSYCHIATRIC DISORDERS

(71) Applicants: UNIVERSITY OF ROCHESTER, Rochester, NY (US); UNIVERSITY OF COPENHAGEN, Copenhagen K (DK)

(72) Inventors: Steven A. Goldman, Webster, NY (US); Zhengshan Liu, Rochester, NY (US); Mikhail Osipovitch, Frederiksberg (DK)

(73) Assignees: University of Rochester, Rochester, NY (US); University of Copenhagen, Copenhagen K (DK)

( * ) Notice: Subject to any disclaimer, the term of this patent is extended or adjusted under 35 U.S.C. 154(b) by 881 days.

(21) Appl. No.: 17/254,008

(22) PCT Filed: Jun. 18, 2019

(86) PCT No.: PCT/US2019/037754

§ 371 (c)(1),
(2) Date: Dec. 18, 2020

(87) PCT Pub. No.: WO2019/246112

PCT Pub. Date: Dec. 26, 2019

(65) Prior Publication Data

US 2021/0260002 A1 Aug. 26, 2021

Related U.S. Application Data

(60) Provisional application No. 62/686,346, filed on Jun. 18, 2018.

(51) Int. Cl.

| | |
|---|---|
| ***A61K 31/19*** | (2006.01) |
| ***A61K 31/4184*** | (2006.01) |
| ***A61K 31/5377*** | (2006.01) |
| ***A61P 25/28*** | (2006.01) |
| ***C12N 15/113*** | (2010.01) |

(52) U.S. Cl.

CPC .......... *A61K 31/19* (2013.01); *A61K 31/4184* (2013.01); *A61K 31/5377* (2013.01); *A61P 25/28* (2018.01); *C12N 15/113* (2013.01); *C12N 2310/11* (2013.01); *C12N 2310/14* (2013.01); *C12N 2310/16* (2013.01); *C12N 2310/531* (2013.01)

(58) Field of Classification Search

CPC ........ A61P 25/28; A61P 25/18; C12N 15/113; C12N 2310/11; C12N 2310/14; C12N 2310/531; C07K 16/18

See application file for complete search history.

(56) References Cited

U.S. PATENT DOCUMENTS

| | | | | |
|---|---|---|---|---|
| 7,524,491 | B2 | 4/2009 | Goldman et al. | |
| 8,206,699 | B2 | 6/2012 | Goldman et al. | |
| 8,263,402 | B1 | 9/2012 | Goldman et al. | |
| 9,371,513 | B2 | 6/2016 | Goldman et al. | |
| 9,709,553 | B2 | 7/2017 | Goldman et al. | |
| 9,724,432 | B2 | 8/2017 | Goldman | |
| 10,190,095 | B2 | 1/2019 | Goldman et al. | |
| 10,279,051 | B2 | 5/2019 | Goldman | |
| 10,450,546 | B2 | 10/2019 | Goldman et al. | |
| 10,626,369 | B2 | 4/2020 | Goldman et al. | |
| 10,779,519 | B2 | 9/2020 | Goldman et al. | |
| 11,344,582 | B2 | 5/2022 | Goldman et al. | |
| 11,596,700 | B2 | 3/2023 | Goldman | |
| 2003/0027153 | A1 | 2/2003 | Meyer et al. | |
| 2010/0247543 | A1 * | 9/2010 | Maes ................ | A61K 31/7105 514/23 |
| 2017/0182097 | A1 | 6/2017 | Goldman | |
| 2020/0048604 | A1 | 2/2020 | Goldman et al. | |
| 2020/0048605 | A1 | 2/2020 | Goldman et al. | |
| 2020/0197445 | A1 | 6/2020 | Goldman et al. | |
| 2022/0025379 | A1 | 1/2022 | Goldman et al. | |
| 2022/0062378 | A1 | 3/2022 | Goldman et al. | |
| 2022/0267737 | A1 | 8/2022 | Goldman et al. | |
| 2022/0273728 | A1 | 9/2022 | Goldman et al. | |
| 2022/0290099 | A1 | 9/2022 | Goldman et al. | |
| 2023/0057355 | A1 | 2/2023 | Goldman et al. | |

(Continued)

FOREIGN PATENT DOCUMENTS

| | | | | |
|---|---|---|---|---|
| EP | 1393776 A1 | 3/2004 | | |
| WO | WO-2011031998 A1 * | 3/2011 | ........... | C12N 15/113 |
| WO | 2012036433 A2 | 3/2012 | | |

OTHER PUBLICATIONS

Khakh and Sofroniew, Astrocytes and Huntington's Disease, 2014, ACS Chemical Neuroscience, 5, p. 494-496) (Year: 2014).*
Huntington's Disease Mayo Clinic Overview, 2022, https://www.mayoclinic.org/diseases-conditions/huntingtons-disease/symptoms-causes/syc-20356117 (Year: 2022).*
Koerber et al., Molecular Evolution of Adeno-associated Virus for Enhanced Glial Gene Delivery, 2009, Molecular Therapy, 17, 2088-2095 (Year: 2009).*
Faideau et al., In vivo expression of polyglutamine-expanded huntingtin by mouse striatal astrocytes impairs glutamate transport: a correlation with Huntington's disease subjects, 2010, 19, p. 3053-3067. (Year: 2010).*

(Continued)

*Primary Examiner* — Jennifer Dunston
*Assistant Examiner* — Keyur A Vyas
(74) *Attorney, Agent, or Firm* — Fox Rothschild LLP

(57) ABSTRACT

The present disclosure is directed to methods of restoring glial cell $K^+$ uptake in a subject. This method involves selecting a subject having impaired glial cell $K^+$ uptake, and administering, to the selected subject, a RE1-Silencing Transcription factor (REST) inhibitor under conditions effective to restore glial cell $K^+$ uptake. Subjects having impaired glial cell $K^+$ uptake include those at risk of having or having a neuropsychiatric disease or disorder.

15 Claims, 18 Drawing Sheets

Specification includes a Sequence Listing.

(56) References Cited

U.S. PATENT DOCUMENTS

2023/0173110 A1 6/2023 Goldman

OTHER PUBLICATIONS https://www.mayoclinic.org/diseases-conditions/huntingtons-disease/symptoms-causes/syc-20356117; May 17, 2022 last updated (Year: 2022).*
Tong et al., Astrocyte Kir4.1 ion channel deficits contribute to neuronal dysfunction in Huntington's disease model mice, 2014, Nature Neuroscience, 17, 694-703. (Year: 2014).*
Hibino et al., Inwardly rectifying potassium channels: their structure, function, and physiological roles, 2010, Physiol. Rev., 90, 291-366, abstract only. (Year: 2010).*
McClelland et al., Neuron-Restrictive SilencerFactor-Mediated Hyperpolarization-Activated Cyclic NucleotideGated Channelopathy in ExperimentalTemporal Lobe Epilepsy, 2011, Ann. Neurol., 70, 454-464. (Year: 2011).*
Phillips, Antisense Inhibition and Adeno-Associated Viral Vector Delivery for Reducing Hypertension, 1997, Hypertension, 29, 177-187. (Year: 1997).*
Ayano, 2016, Bipolar Disorders and Valproate: Pharmacokinetics, Pharmacodynamics, Therapeutic Effects and Indications of Valproate: Review of Articles, Bipolar Disord., 2, p. 1-5, DOI: 10.4172/2472-1077.1000109. (Year: 2016).*
Da Silveira Paulsen et al., Valproate reverts zinc and potassium imbalance in schizophrenia-derived reprogrammed cells, 2014, Schizophrenia Res., 154, 30-35. (Year: 2014).*
Office Action and Search Report in CN Application No. 201980053363.2 (mailed Mar. 10, 2023).
Zhao et al., "Brain REST/NRSF is not only a Silent Repressor but also an Active Protector," Mol. Neurobiol. 54:541-550 (2016).
Wang et al., "The Use of Psychiatric Drugs and Worsening Body Mass Index Among Inpatients with Schizophrenia," International Clinical Psychopharmacology 29(4):235-238 (2013).
Chiu et al., "Therapeutic Potential of Mood Stabilizers Lithium and Valproic Acid: Beyond Bipolar Disorder," Pharmacological Reviews 65:105-142 (2013).
International Search Report and Written Opinion for corresponding Application No. PCT/US2019/037754 (mailed Nov. 13, 2019).
Wang et al., "The Use of Psychiatric Drugs and Worsening Body Mass Index Among Inpatients with Schizophrenia," International Clin. Psychopharmacol. 29:235-238 (2014).
Chiu et al., "Therapeutic Potential of Mood Stabilizers Lithium and Valproic Acid: Beyond Bipolar Disorder," Pharmalogical Rev. 65(1):105-142 (2013).
Zhao et al., "Brain REST/NRSF is not Only a Silent Repressor but Also an Active Protector," Mol. Neurobiol. 54(1):541-550 (2016).
Schneider et al., "Behavioral Alterations in Rats Prenatally Exposed to Valproic acid: Animal Model of Autism," Neuropsychopharmacol. 30(1):80-89 (2004).
U.S. Appl. No. 17/430,768, filed Aug. 13, 2021, first named inventor Steven A. Goldman.
U.S. Appl. No. 17/920,140, filed Oct. 20, 2022, first named inventor Steven A. Goldman.
U.S. Appl. No. 18/135,543, filed Apr. 17, 2023, first named inventor Steven A. Goldman.
Notice of Reasons for Rejection in JP Application No. 2020-570726 (dated May 22, 2023).
Charbord et al., "High Throughput Screening for Inhibitors of Rest in Neural Derivatives of Human Embyronic Stem Cells Reveals a Chemical Compound that Promotes Expression of Neuronal Genes," Stem Cell 31(9):1816-1828 (2013).
Allen, M. et al., "Origin of the U87MG glioma cell line: Good news and bad news," Science Translational Medicine (2016); 8(354): p. 354re3.
Charbord, J. et al., "Stem Cell Technology: Epigenetics, Genomics, Proteomics, and Metabonomics," Stem Cells (2013); 31: pp. 1816-1828.
Windrem, M. S. et al., "Human iPSC glial mouse chimeras reveal glial contributions to schizophrenia," Cell Stem Cell (2017); 21(2): pp. 195-208.
Brismar, T. et al., "Mechanism of High K+ and T1+ Uptake in Cultured Human Glioma Cells," Cellular and Molecular Neurobiology (1995); 15(3): pp. 351-360.
Liu, Z., "The Contribution of Glial Molecular Pathology to Schizophrenia," Ph. D. thesis, Jan. 1, 2017, XP055672545, Rochester New York, USA.

* cited by examiner

SUBSTITUTE SHEET (RULE 26)

METHODS OF TREATING SCHIZOPHRENIA AND OTHER NEUROPSYCHIATRIC DISORDERS

This application is a national stage application under 35 U.S.C. § 371 of PCT Application No. PCT/US2019/037754, filed Jun. 18, 2019, which claims the benefit of U.S. Provisional Patent Application Ser. No. 62/686,346 and Jun. 18, 2018, respectively, which is hereby incorporated by reference in its entirety.

This invention was made with government support under R01 MH099578 awarded by the National Institutes of Health. The government has certain rights in this invention.

FIELD

The present disclosure relates to methods for restoring glial cell potassium ($K^+$) uptake in glial cells having impaired $K^+$ uptake. These methods are suitable for treating a subject suffering from a neuropsychiatric condition.

BACKGROUND

Schizophrenia is a psychiatric disorder characterized by delusional thought, auditory hallucination and cognitive impairment, which affects roughly 1% of the population worldwide, and yet remains poorly understood (Allen et al., "Systematic Meta-Analyses and Field Synopsis of Genetic Association Studies in Schizophrenia: The SzGene Database," *Nature Genetics* 40:827-834 (2008); Sawa & Snyder, "Schizophrenia: Diverse Approaches to a Complex Disease," *Science* 296:692-695 (2002)). Over the past decade, it has become clear that a number of schizophrenia-associated genes are involved in the development and physiology of glial cells (Yin et al., "Synaptic Dysfunction in Schizophrenia," *Adv. Exp. Med. Biol.* 970:493-516 (2012)). Accordingly, both astrocytic and oligodendrocytic dysfunction has been implicated in the etiology of schizophrenia. Astrocytes in particular have essential roles in both the structural development of neural networks as well as the coordination of neural circuit activity, the latter through their release of glial transmitters, maintenance of synaptic density, and regulation of synaptic potassium and neurotransmitter levels (Christopherson et al., "Thrombospondins are Astrocyte-Secreted Proteins That Promote CNS Synaptogenesis," *Cell* 120:421-433 (2005); Chung et al., "Astrocytes Mediate Synapse Elimination Through MEGF10 and MERTK Pathways," *Nature* 504:394-400 (2013); and Thrane et al., "Ammonia Triggers Neuronal Disinhibition and Seizures by Impairing Astrocyte Potassium Buffering," *Nat. Med.* 19:1643-1648 (2013)). However, the role that astrocyte dysfunction plays in the development of neuropsychiatric disorders, such as schizophrenia, is unknown. The present disclosure is aimed at overcoming this and other deficiencies in the art.

SUMMARY

A first aspect of the present disclosure relates to a method of restoring $K^+$ uptake by glial cells, where said glial cells have impaired $K^+$ uptake. This method involves administering, to the glial cells having impaired $K^+$ uptake, a RE1-Silencing Transcription factor (REST) inhibitor under conditions effective to restore $K^+$ uptake by said glial cells.

Another aspect of the present disclosure relates to a method of restoring $K^+$ uptake by glial cells in a subject. This method involves selecting a subject having impaired glial cell $K^+$ uptake, and administering, to the selected subject, a RE1-Silencing Transcription factor (REST) inhibitor under conditions effective to restore $K^+$ uptake by said glial cells.

Another aspect of the present disclosure relates to a method of treating or inhibiting the onset of a neuropsychiatric disorder in a subject. This method involves selecting a subject having or at risk of having a neuropsychiatric disorder, and administering, to the selected subject, a REST inhibitor under conditions effective to treat or inhibit the onset of the neuropsychiatric disorder in the subject.

To investigate the role of glial pathology in neurological and neuropsychiatric disorders like schizophrenia, a protocol for generating glial progenitor cells (GPCs) from induced pluripotent cells (iPSCs) was established (Wang et al., "Human iPSC-Derived Oligodendrocyte Progenitor Cells Can Myelinate and Rescue a Mouse Model of Congenital Hypomyelination," *Cell Stem Cell* 12:252-264 (2013), which is hereby incorporated by reference in its entirety). This model permits the generation of GPCs and their derived astrocytes and oligodendrocytes from patients with schizophrenia, in a manner that preserves their genetic integrity and functional repertoires. This protocol has provided a means by which to assess the differentiation, gene expression and physiological function of astrocytes derived from patients with schizophrenia, both in vitro and in vivo after engraftment into immune deficient mice (Windrem et al., "Human iPSC Glial Mouse Chimeras Reveal Glial Contributions to Schizophrenia," *Cell Stem Cell* 21:195-208.e6 (2017), which is hereby incorporated by reference in its entirety). It was noted that such human glial chimeric mice, colonized with iPSC-derived GPCs generated from schizophrenic patients, exhibited profound abnormalities in both astrocytic differentiation and mature structure that were associated with significant physiological and behavioral abnormalities. Importantly, RNA sequence analysis revealed that the developmental defects in these schizophrenia GPCs were associated with the down-regulation of a core set of differentiation-associated genes, whose transcriptional targets included a host of transporters, channels and synaptic modulators found similarly deficient in schizophrenia glia.

As described herein, targetable signaling nodes at which such schizophrenia-associated glial pathology might be moderated were identified. To that end, iPSC GPCs were generated from patients with childhood-onset schizophrenia or from their normal controls (CTR), and astrocytes were produced from these. Both patterns of gene expression and astrocytic functional differentiation by schizophrenic- and control-derived GPCs were compared. Since the preservation of $K^+$ homeostasis is a critical element of astrocytic functional competence, and the RNA-seq data indicated the down-regulation of a number of potassium channels, the uptake of $K^+$ by schizophrenic astrocytes was also assessed. It was found that the schizophrenic cells indeed manifested impaired $K^+$ uptake. Investigating the basis for the impaired transcription of $K^+$ channels by these schizophrenic glia, it was discovered that aberrant expression of the REST repressor is responsible for the diminished potassium channel gene expression and impaired $K^+$ uptake of these schizophrenic astrocytes. By focusing on the development of glial pathology in schizophrenia, the dysregulation of REST dependent transcription has been identified as critical to disease pathogenesis, and as viable target for the treatment of this devastating disorder.

Figure 1A:
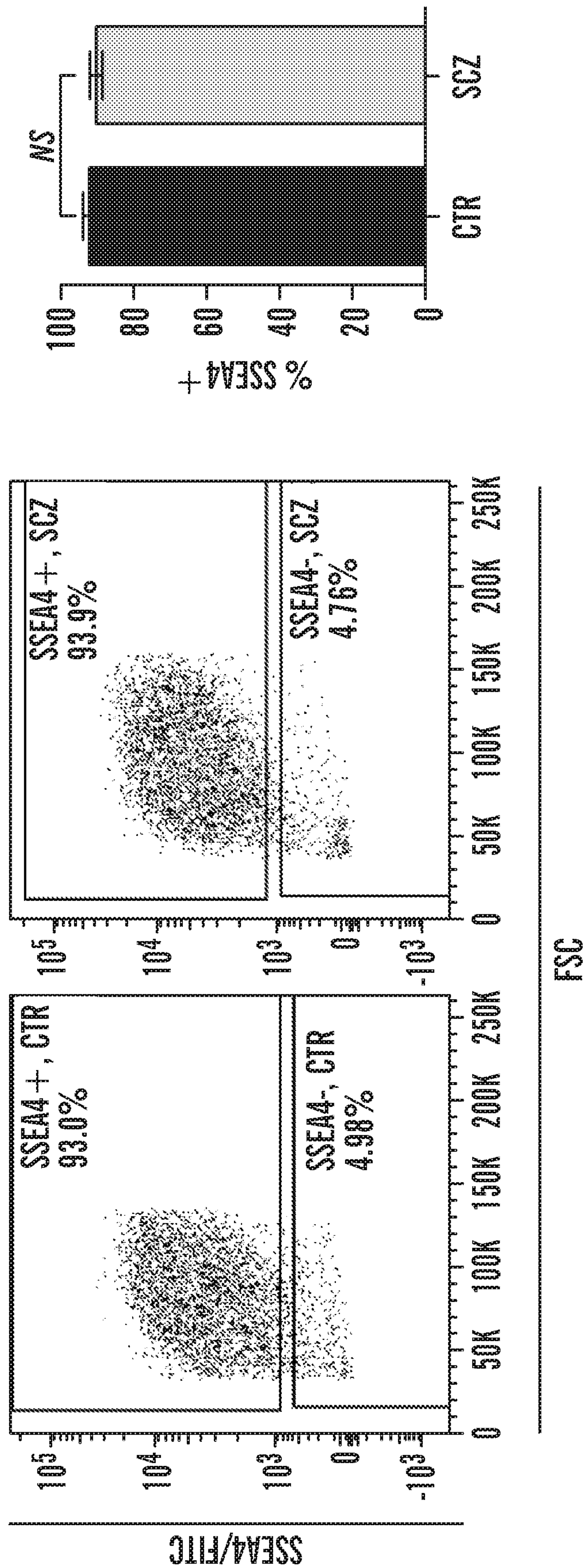
FIGS. 1A-1C show efficient generation of human glial progenitor cells (hGPCs) from schizophrenic (SCZ) iPSCs.
Figure 1B:
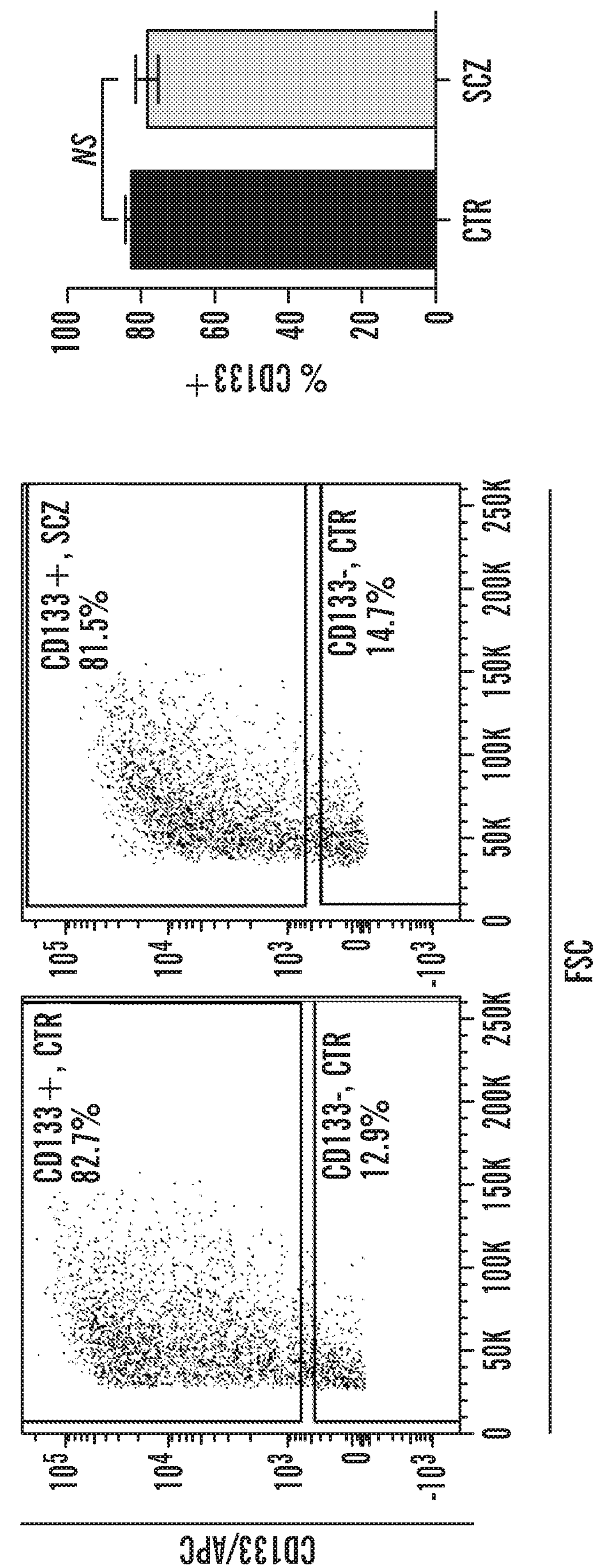
Figure 1C:
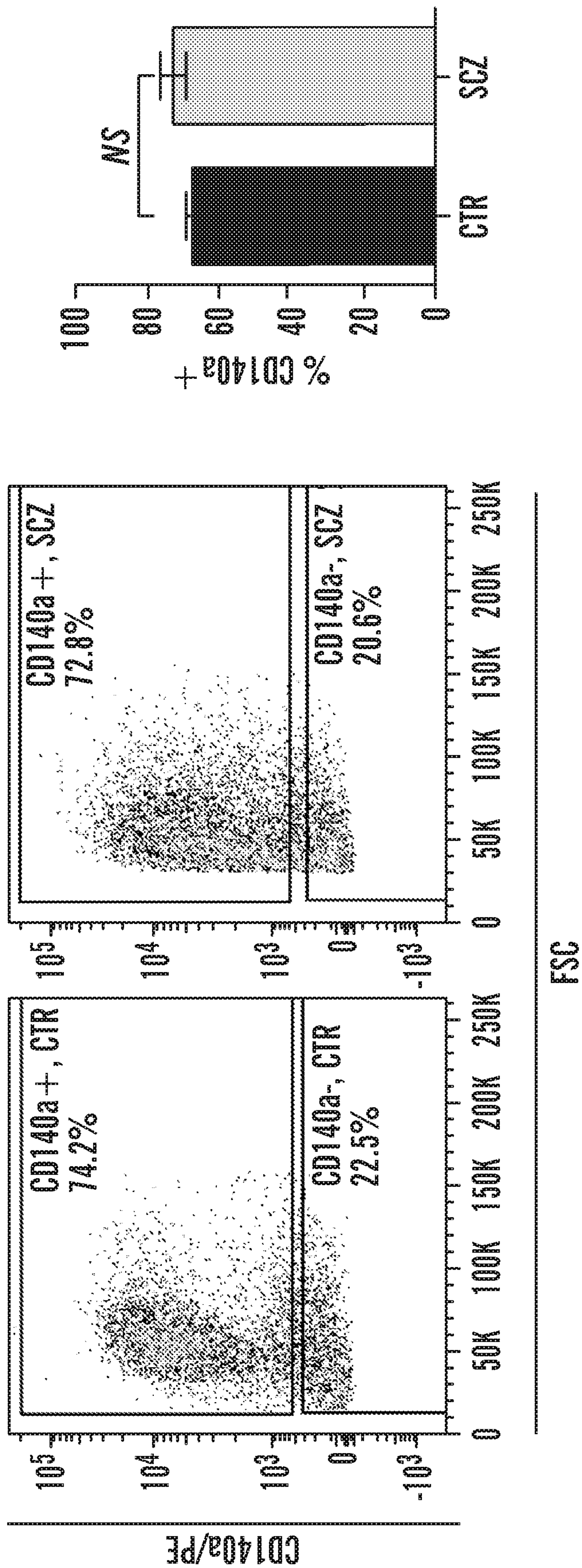

Flow cytometry analysis revealed that >90% of undifferentiated hiPSCs expressed SSEA4 in both SCZ (4 SCZ lines, n≥3/each line)- and control (CTR) (4 CTR lines, n≥3/each line)-derived hiPSCs (FIG. 1A). At the neural progenitor cell (NPC) stage, the expression of the NPC marker CD133 was no different between SCZ- and CTR-derived lines as shown in the flow cytometry data of FIG. 1B. CD140a-defined hGPCs were likewise similarly generated from both SCZ- and CTR-derived iPSCs, and the relative proportion of CD140a$^+$ cells was no different in SCZ and CTR hGPC cultures as shown in FIG. 1C. Two tailed t-tests; NS: not significant; means±SEM.

Figure 2A:
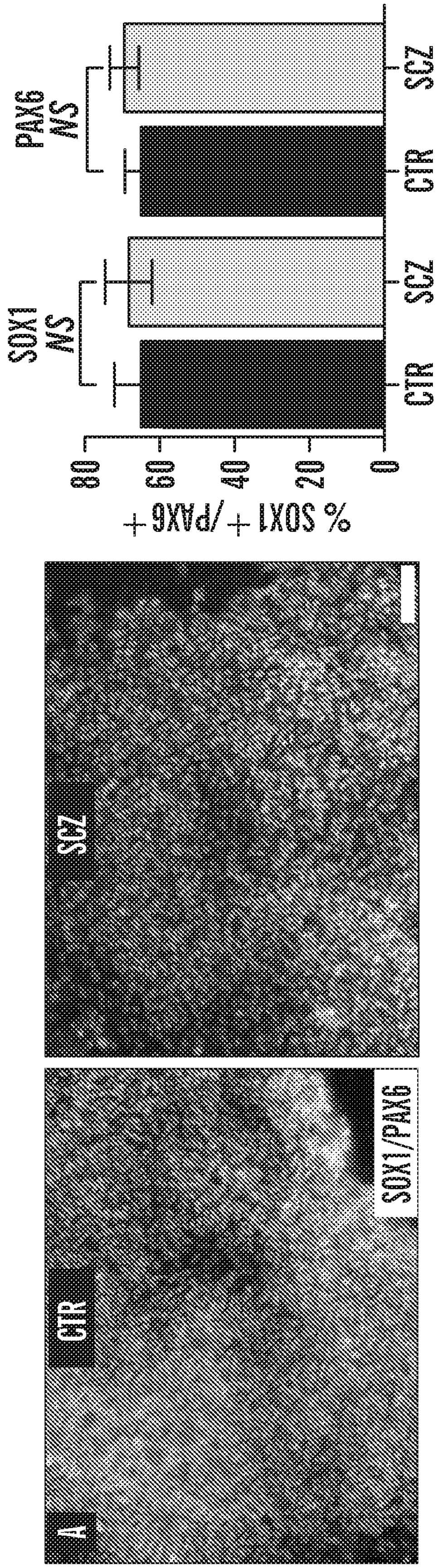
Figure 2B:
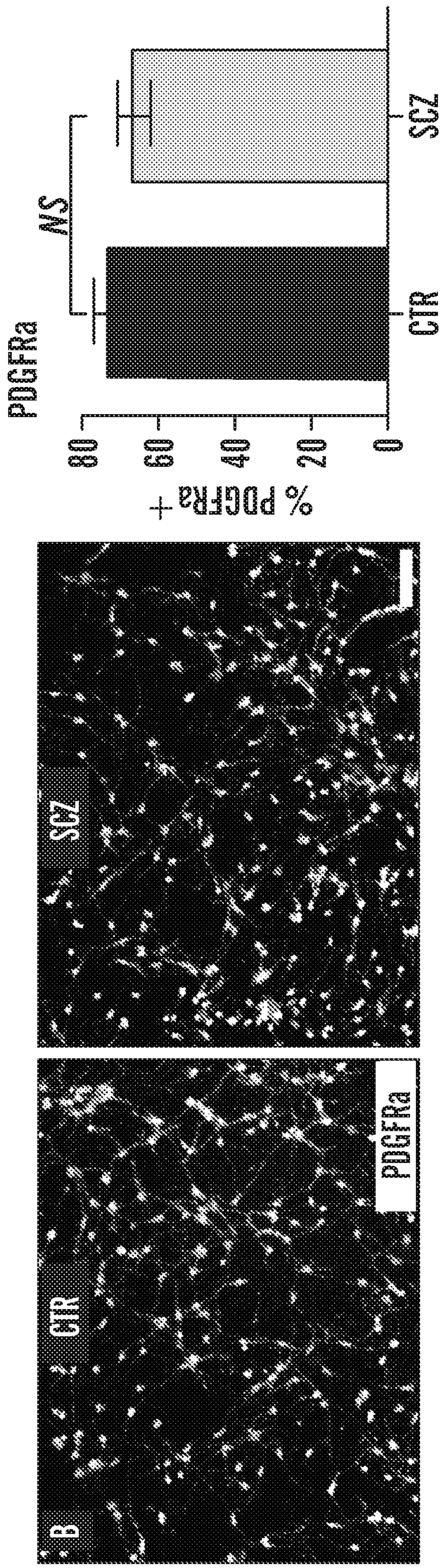
Figure 2C:
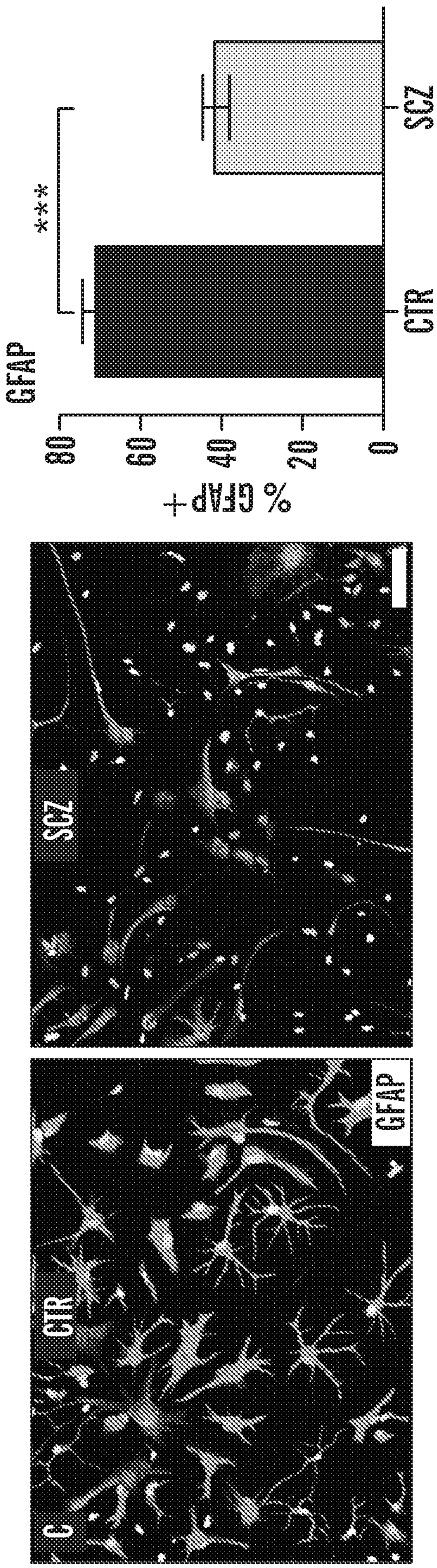

FIGS. 2A-2C show that astrocytic differentiation was impaired in SCZ GPCs. At the neural progenitor cell (NPC) stage, both SCZ and CTR (4 distinct patients and derived lines each, n≥33/each line) hNPCs highly expressed both SOX1 and PAX6 as shown by the immuncytochemical analysis of FIG. 2A. Similarly, the efficiency of PDGFRα/CD140a-defined hGPC generation did not differ between SCZ and CTR lines (4 different patient-specific lines each, n≥3/each line) (FIG. 2B). In contrast, the proportion of GFAP$^+$ astrocytes was significantly higher in CTR lines (4 CTR lines, n≥33/each line [70.1±2.4%]) vs. SCZ lines (4 SCZ lines, n≥33/each line, [39.9±2.0%]) as shown in FIG. 2C. Scale: 50 μm; ***p<0.001 by two tailed t-test; NS: not significant; mean±SEM.

Figure 3A:
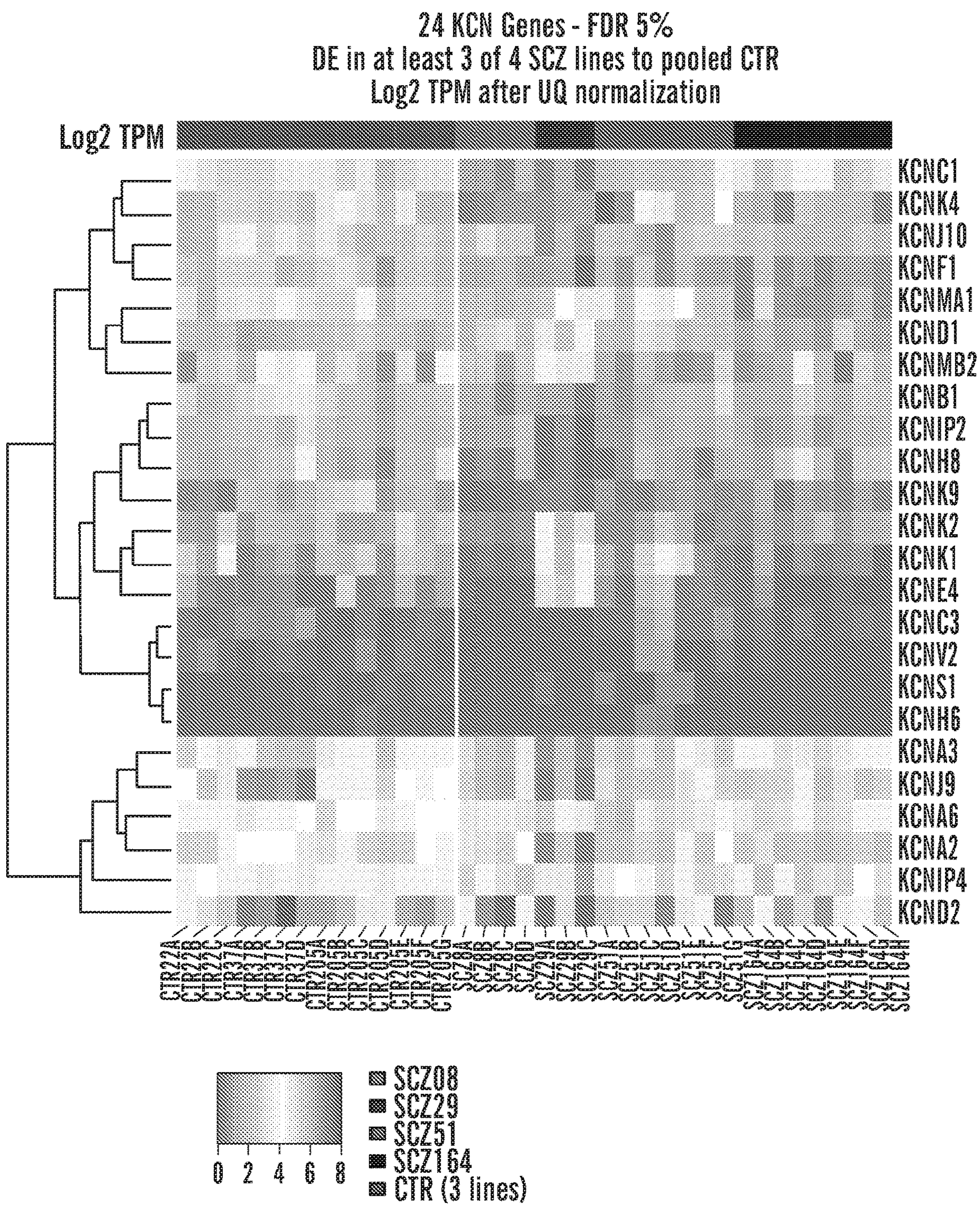
Figure 3B:
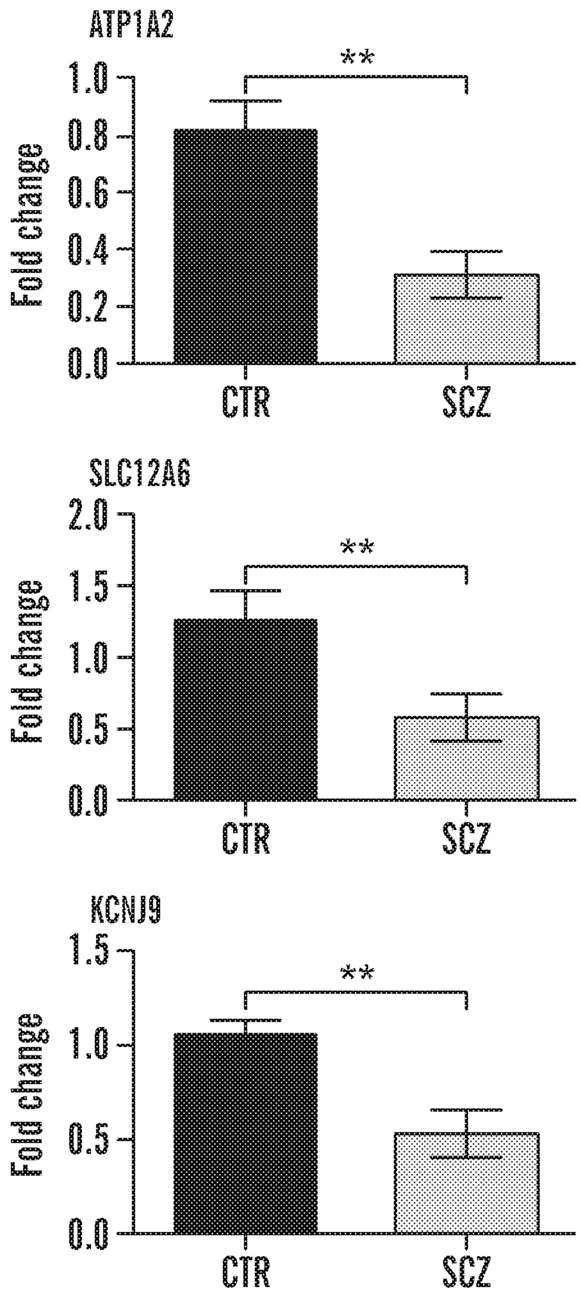
Figure 3C:
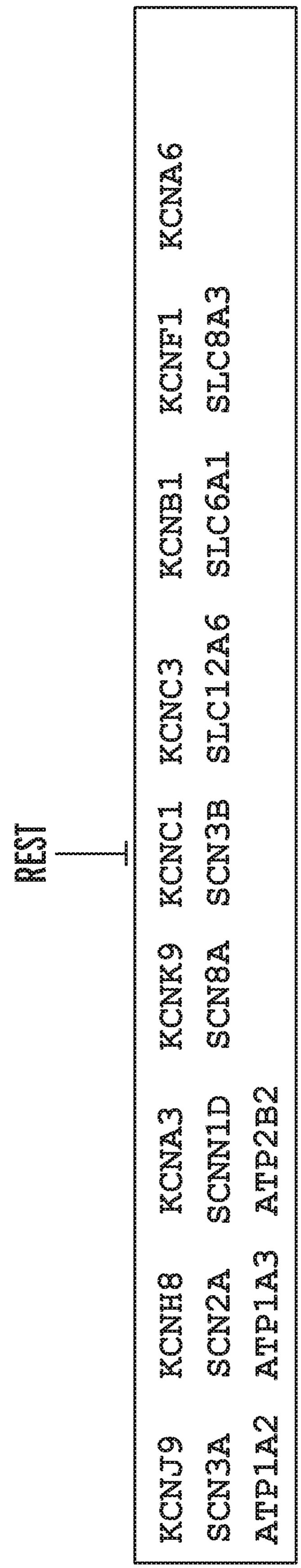

FIGS. 3A-3C show REST represses potassium channel (KCN)-associated gene expression in SCZ hGPCs. FIG. 3A is a heat map showing the differentially expressed potassium channel genes in SCZ-derived hGPC lines. Each SCZ-derived hGPC line was individually compared against three pooled CTR-derived hGPC lines (FDR 5%, FC>2.00 [if applicable]). Genes shown were found differentially expressed in at least three out of four assessed SCZ-derived hGPC lines. qPCR confirmed that potassium channel-associated genes including ATP1A2, SLC12A6, and KCNJ9 were all significantly downregulated in SCZ hGPCs (4 SCZ lines, 3 repeats/each line), relative to CTR cells (4 CTR lines, 3 repeats/each line) (FIG. 3B). Biobase-Transfac revealed that the majority of downregulated potassium channel-associated genes in SCZ hGPCs from the RNA-seq data were targets of the REST repressor as depicted in FIG. 3C. **p<0.01 by two tailed t-test; mean±SEM.

Figure 4A:
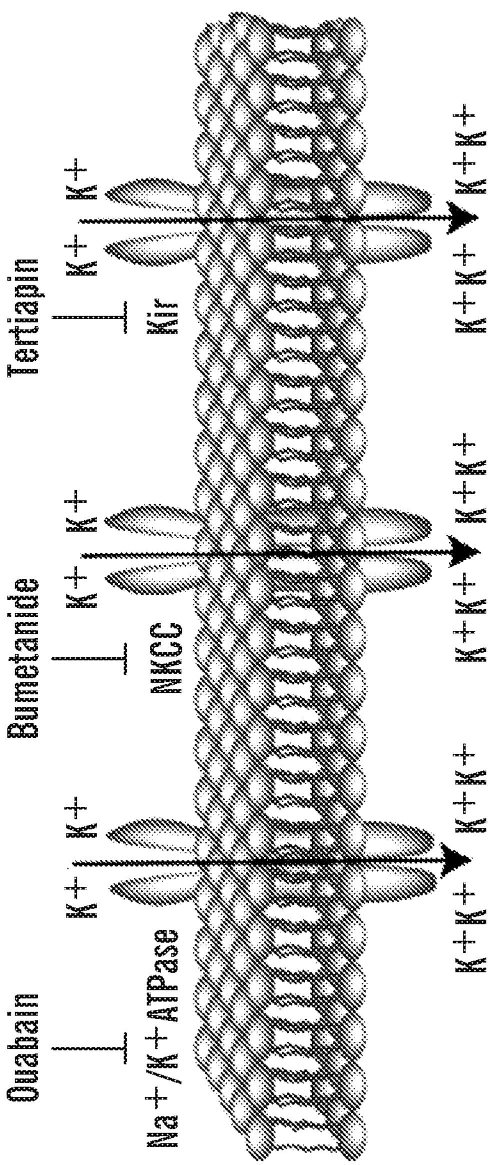
Figure 4B:
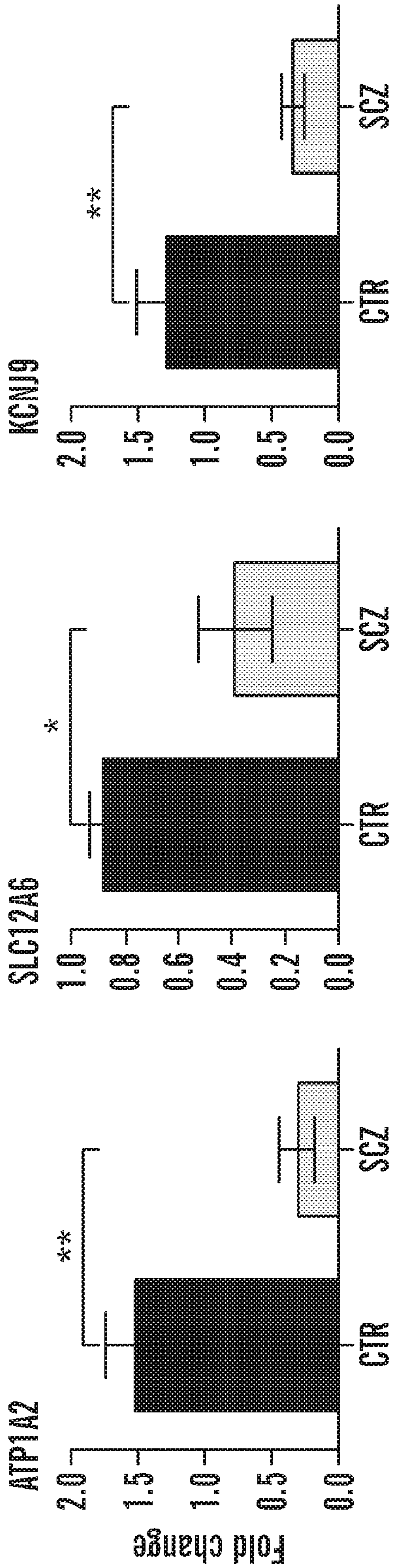
Figure 4C:
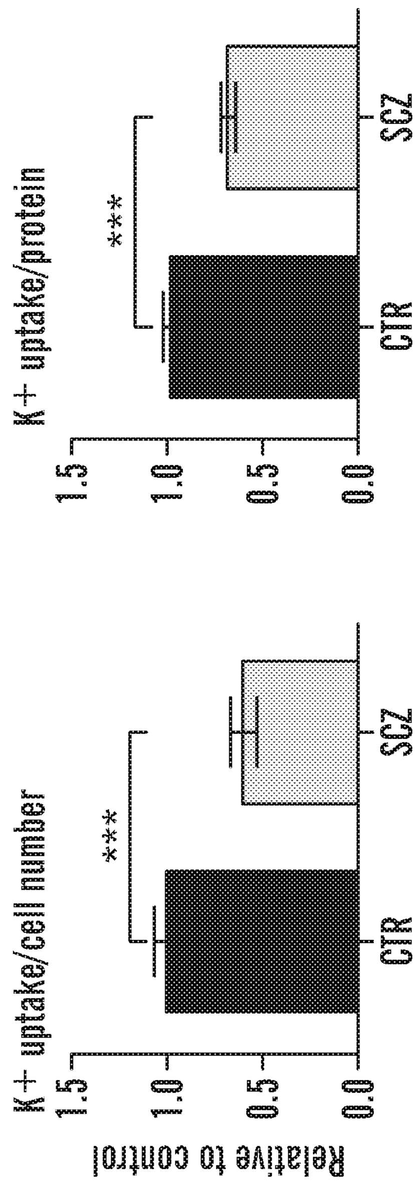

FIGS. 4A-4E show the decrease in potassium uptake in SCZ astrocytes. FIG. 4A is a schematic depiction of the Na$^+$/K$^+$-ATPase, Na$^+$/K$^+$/2Cl cotransporter (NKCC), and inwardly rectifying K$^+$ channel (Kir) involvement in the regulation of potassium uptake by astrocytes. qPCR confirmed that several K$^+$ channel-associated genes were down-regulated in SCZ CD44$^+$ astrocyte-biased GPCs relative to CTR cells as shown in the graphs of FIG. 4B. SCZ and CTR CD44$^+$ GPCs were cultured in FBS with BMP4 to produce mature GFAP$^+$ astrocytes, which were then assessed for K$^+$ uptake. FIG. 4C shows K$^+$ uptake in SCZ and CTR normalized to cell number (left graph) and normalized to total protein (right graph). K$^+$ uptake by SCZ astrocytes was significantly reduced (4 SCZ lines, 5 repeats/each line), compared to K$^+$ uptake by CTR astrocytes (4 CTR lines, 5 repeats/each line). Astrocytes were treated with ouabain, bumetanide, and tertiapin to assess which potassium channel classes were functionally impaired in SCZ astrocytes (4 SCZ lines, 4 repeats/each line). Both ouabain and bumetanide efficiently decreased K$^+$ uptake by CTR astrocytes (4 CTR lines, 4 repeats/each line) (FIGS. 4D and 4E, left graphs), whereas neither affected K$^+$ uptake by SCZ astrocytes (FIGS. 4D and 4E, right graphs. *P<0.05, P<0.01, *P<0.001 by two tailed t-test for B and C; ***P<0.001 by one-way ANOVA for D; NS: not significant; mean±SEM.

Figure 5A:
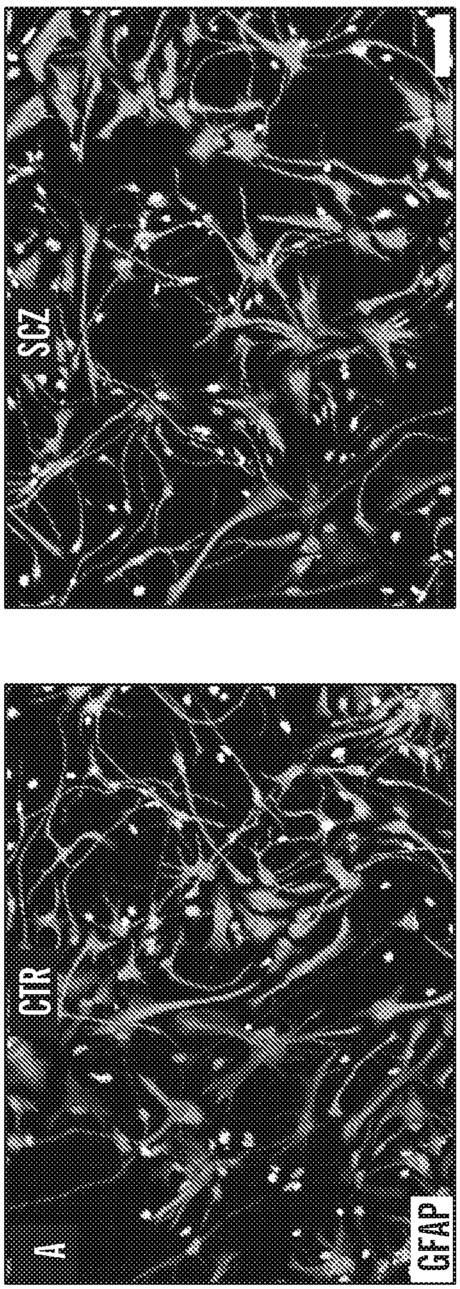
Figure 5B:
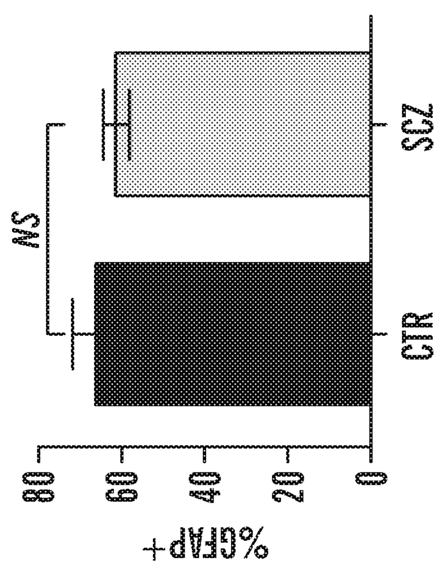
Figure 5C:
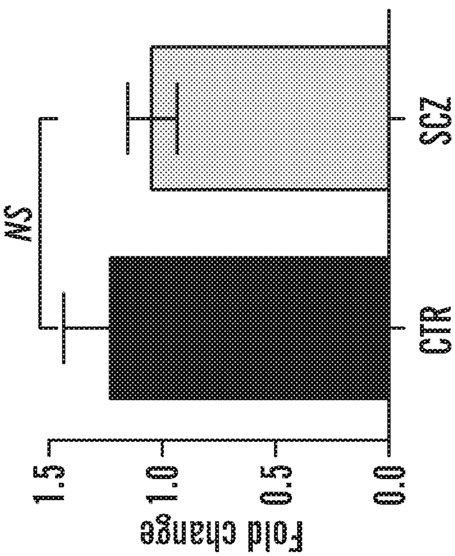
Figure 6A:
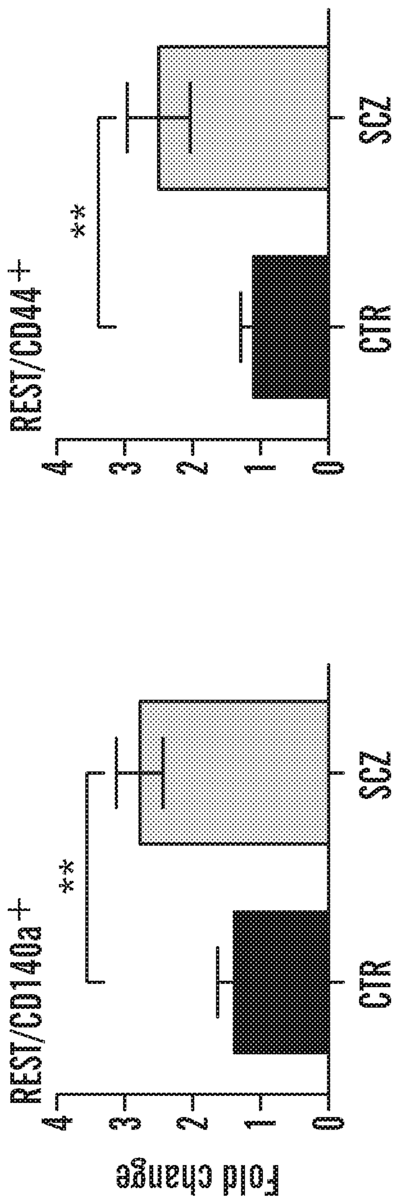
Figure 6B:
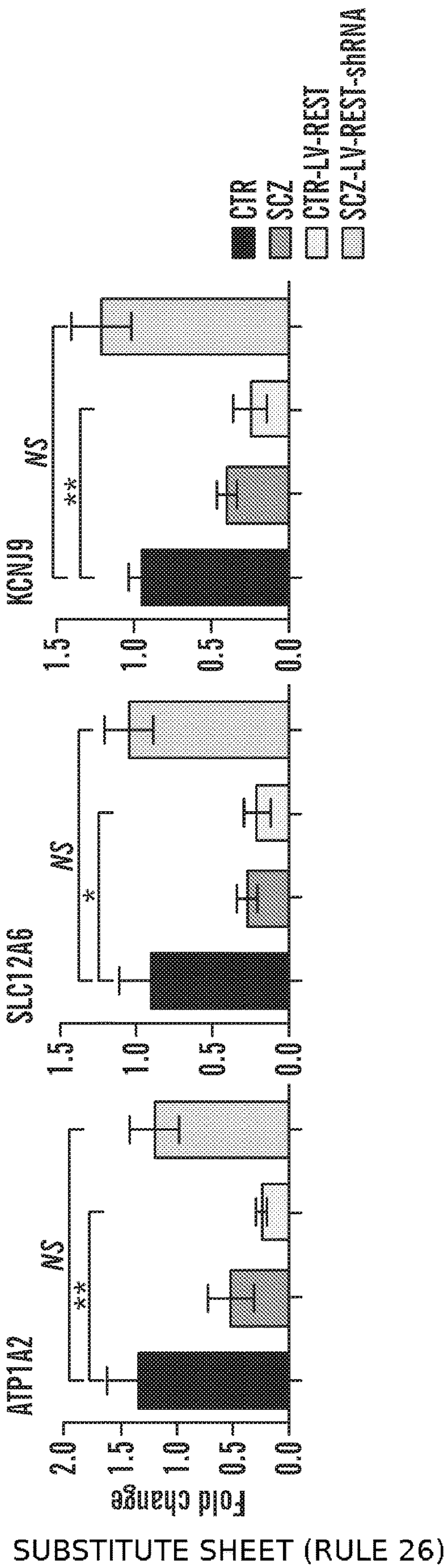

FIGS. 5A-5C show generation of astrocytes from SCZ CD44+ astrocyte-biased progenitors. Both SCZ-derived and CTR-derived CD44+ astrocytic precursors were induced to differentiate into astrocytes. Immunostaining for GFAP demonstrated that the efficiencies of astrocytic generation were not significantly different between SCZ-derived lines (FIG. 5A, right image; 4 SCZ lines, 5 repeats/each line) and CTR-derived lines (FIG. 5A, left image; 4 CTR lines, 5 repeats/each line) (see also graph of FIG. 5B). qPCR revealed no difference in GFAP mRNA expression between SCZ- and CTR-derived CD44+ astrocytic precursors as depicted in FIG. 5C. Scale: 50 μm. Two tailed t-tests for B and C; NS: not significant; mean±SEM FIGS. 6A-6E show that REST regulates potassium uptake by SCZ astrocytes. qPCR confirmed that REST was upregulated in both CD140a-sorted SCZ hGPCs relative to their controls (FIG. 6A, left graph) and in CD44-sorted SCZ astrocytic progenitor cells relative to CTR cells (FIG. 6A, right graph). The expression of several K$^+$ channel-associated genes, including ATP1A2 (FIG. 6B, left graph), SLC12A6 (FIG. 6B, middle graph), and KCNJ9 (FIG. 6B, right graph) was significantly repressed in CTR glia in which REST was overexpressed via lentiviral-REST transduction (4 CTR lines, 3 repeats/each line). In contrast, their expression was robustly upregulated in SCZ lines in which REST was knocked down via lentiviral REST shRNAi (4 SCZ lines, 3 repeats/each line) (FIG. 6B left, middle, and right graphs). K$^+$ uptake by REST-transduced CTR astrocytes fell, mimicking that SCZ glia (FIG. 6C, right and left graphs, compare 1$^{st}$ and 3$^{rd}$ bars), whereas K$^+$ uptake was rescued in SCZ lines subjected to REST knockdown (FIG. C, right and left graphs, compare 2$^{nd}$ and 4$^{th}$ bars). Both ouabain and bumetanide significantly reduced K$^+$ uptake by SCZ glia with REST knockdown (FIGS. 6D and 6E, right graphs; 4 SCZ lines, 3 repeats/each line). K$^+$ uptake in control cells exposed to similar conditions is shown in the left graphs of FIGS. 6D and 6E. **P<0.01 by two tailed t-test for A; *P<0.05, P<0.01, *P<0.001 by one-way ANOVA for B, C, and D; NS: not significant; mean±SEM.

Figure 7A:
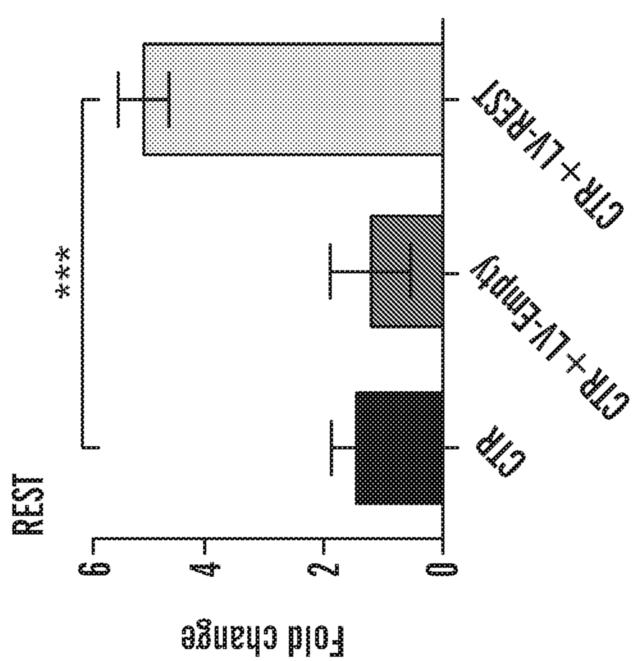
Figure 7B:
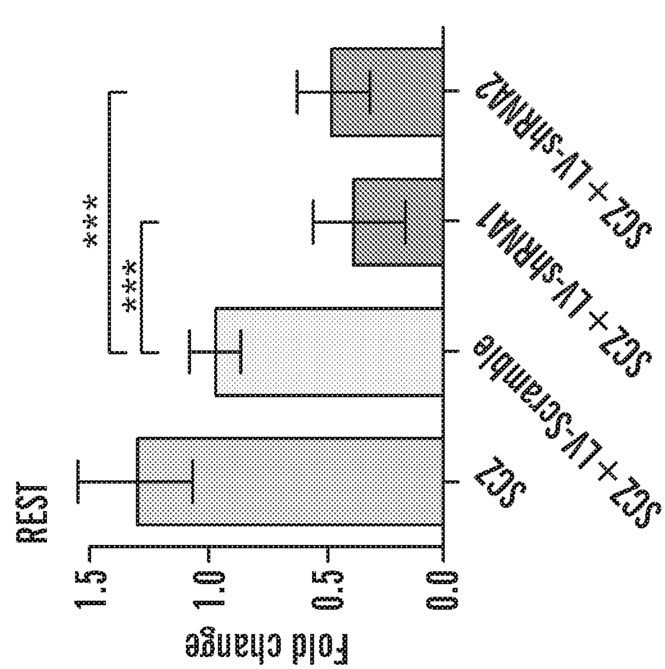

FIGS. 7A-7B show validation of REST overexpression and knockdown in control (FIG. 7A) and SCZ astroglial (FIG. 7B). PCR confirmed that lentiviral-REST transduction of CTR astroglia (4 CTR lines, 3 repeats/each line) yielded the significant up-regulation of REST expression, relative to untransduced cells (FIG. 7A). In contrast, lentiviral-REST-shRNAi transduction of CD44-defined SCZ astroglia (4 SCZ lines, 3 repeats/each line) substantially repressed REST expression (FIG. 7B). ***p<0.001 by one-way ANOVA; mean±SEM.

DETAILED DESCRIPTION

A first aspect of the present disclosure relates to a method of restoring K$^+$ uptake by glial cells, where said glial cells have impaired K$^+$ uptake. This method involves administering, to glial cells having impaired K$^+$ uptake, a RE1-Silencing Transcription factor (REST) inhibitor under conditions effective to restore K$^+$ uptake by said glial cells.

Another aspect of the present disclosure relates to a method of restoring K$^+$ uptake by glial cells in a subject. This method involves selecting a subject having impaired glial cell K$^+$ uptake, and administering, to the selected subject, a RE1-Silencing Transcription factor (REST) inhibitor under conditions effective to restore K$^+$ uptake by said glial cells. In some embodiment, the REST inhibitor is a glial cell targeted REST inhibitor as described herein.

As referred to herein, "glial cells" encompass glial progenitor cells, oligodendrocyte-biased progenitor cells, astrocyte-biased progenitor cells, oligodendrocytes, and astrocytes. Glial progenitor cells are bipotential progenitor cells of the brain that are capable of differentiating into both oligodendrocytes and astrocytes. Glial progenitor cells can be identified by their expression of certain stage-specific surface antigens, such as the ganglioside recognized by the A2B5 antibody and PDGFRα (CD140a), as well as stage-specific transcription factors, such as OLIG2, NKX2.2, and SOX10. Oligodendrocyte-biased and astrocyte-biased progenitor cells are identified by their acquired expression of stage selective surface antigens, including, for example CD9 and the lipid sulfatide recognized by the O4 antibody for oligodendrocyte-biased progenitor cells, and CD44 for astrocyte-biased progenitors. Mature oligodendrocytes are identified by their expression of myelin basic protein, and mature astrocytes are most commonly identified by their expression of glial fibrillary acidic protein (GFAP). In one embodiment of the methods described herein, $K^+$ uptake is restored in glial progenitor cells. In another embodiment, $K^+$ uptake is restored in astrocyte-biased progenitor cells. In another embodiment, $K^+$ uptake is restored in astrocytes.

In accordance with these aspects of the present disclosure, cells having impaired $K^+$ uptake, are glial cells, in particular glial progenitor cells, astrocyte-biased progenitor cells, and astrocytes, having reduced $K^+$ uptake as compared to normal, healthy glial cells. In one embodiment, glial cells having reduced $K^+$ uptake are glial cells where one or more potassium channel encoding genes is down regulated, causing a reduction in the corresponding potassium channel protein expression. In particular, a down regulation in expression of one or more potassium channel encoding genes selected from KCNJ9, KCNH8, KCNA3, KCNK9, KCNC1, KCNC3, KCNB1, KCNF1, KCNA6, SCN3A, SCN2A, SCNN1D, SCN8A, SCN3B, SLC12A6, SLC6A1, SLC8A3, ATP1A2, ATP1A3, ATP2B2 can lead to a reduction in glial cell $K^+$ uptake. As described herein, the down regulation of the aforementioned genes is caused by an upregulation in the expression and activity of the neuron restrictive silencing factor (NRSF), which is also known as RE1-Silencing Transcription Factor (REST). REST is a potent transcriptional repressor, typically involved in the repression of neural genes in non-neural cells.

Thus, in one embodiment, selecting a subject having impaired glial cell $K^+$ uptake involves assessing potassium uptake by glial cells of the subject, comparing the level of potassium uptake by said glial cells to the level of potassium uptake by a population of control, healthy glial cells, and selecting the subject having a reduction in glial cell $K^+$ uptake. In another embodiment, selecting a subject having impaired glial cell $K^+$ uptake involves assessing glial cell expression level of one or more potassium channel encoding genes selected from the group consisting of KCNJ9, KCNH8, KCNA3, KCNK9, KCNC1, KCNC3, KCNB1, KCNF1, KCNA6, SCN3A, SCN2A, SCNN1D, SCN8A, SCN3B, SLC12A6, SLC6A1, SLC8A3, ATP1A2, ATP1A3, ATP2B2, and selecting the subject if there is a downregulation in the expression of the one or more potassium channel encoding genes. In another embodiment, selecting a subject having impaired glial cell $K^+$ uptake involves assessing glial cell protein expression of one or more potassium channels including, GIRK-3 (encoded by KCNJ9), potassium voltage-gated channel subfamily H member 8 (encoded by KCNH8), potassium voltage-gated channel subfamily A member 3 (encoded by KCNA3), potassium channel subfamily K member 9 (encoded by KCNK9), potassium voltage-gated channel subfamily C member 1 (encoded by KCNC1), potassium voltage-gated channel subfamily C member 3 (encoded by KCNC3), potassium voltage-gated channel subfamily B member 1 (encoded by KCNB1), potassium voltage-gated channel subfamily F member 1 (encoded by KCNF1), potassium voltage-gated channel subfamily A member 6 (encoded by KCNA6), Sodium channel protein type 3 subunit alpha (encoded by SCN3A), sodium channel protein type 2 subunit alpha (encoded by SCN2A), amiloride-sensitive sodium channel subunit delta (encoded by SCNN1D), sodium channel protein type 8 subunit alpha (encoded by SCN8A), sodium channel subunit beta-3 (encoded by SCN3B), solute carrier family 12 member 6 (i.e., $K^+/Cl^-$ cotransporter 3) (encoded by SLC12A6), sodium- and chloride-dependent GABA transporter 1 (i.e., GAT-1) (encoded by SLC6A1), $Na^+/Ca^{+2}$ exchanger 3 (encoded by SLC8A3), $Na^+/K^+$-transporting ATPase subunit alpha-2 (encoded by ATP1A2), $Na^+/K^+$-transporting ATPase subunit alpha-2 (encoded by ATP1A3), plasma membrane calcium-transporting ATPase 2 (i.e., PMCA2) (encoded by ATP2B2). The subject is selected for treatment using the methods as described herein if there is a decrease in the level of one or more potassium channel proteins. In another embodiment, selecting a subject having impaired glial $K^+$ uptake involves assessing glial cell REST expression and selecting the subject if there is an increase in REST gene and/or protein expression.

Potassium uptake, potassium channel gene expression, potassium channel protein expression, and REST gene expression can each be assessed using methods described herein and that are well known to those of skill in the art. These parameters can be assessed in a glial cell sample taken from a subject. Alternatively, one or more of these parameters can be assessed in a glial cell sample derived from induced pluripotent stem cells (iPSCs) derived from the subject. iPSCs can be obtained from virtually any somatic cell of the subject, including, for example, and without limitation, fibroblasts, such as dermal fibroblasts obtained by a skin sample or biopsy, synoviocytes from synovial tissue, keratinocytes, mature B cells, mature T cells, pancreatic β cells, melanocytes, hepatocytes, foreskin cells, cheek cells, or lung fibroblasts, peripheral blood cells, bone marrow cells, etc. iPSCs may be derived by methods known in the art including the use of integrating viral vectors (e.g., lentiviral vectors, inducible lentiviral vectors, and retroviral vectors), excisable vectors (e.g., transposon and floxed lentiviral vectors), and non-integrating vectors (e.g., adenoviral and plasmid vectors) to deliver the aforementioned genes that promote cell reprogramming (see e.g., Takahashi and Yamanaka, *Cell* 126:663-676 (2006); Okita. et al., *Nature* 448:313-317 (2007); Nakagawa et al., *Nat. Biotechnol.* 26:101-106 (2007); Takahashi et al., *Cell* 131:1-12 (2007); Meissner et al. *Nat. Biotech.* 25:1177-1181 (2007); Yu et al. *Science* 318:1917-1920 (2007); Park et al. *Nature* 451:141-146 (2008); and U.S. Patent Application Publication No. 2008/0233610, which are hereby incorporated by reference in their entirety). Other methods for generating IPS cells include those disclosed in WO2007/069666, WO2009/006930, WO2009/006997, WO2009/007852, WO2008/118820, U.S. Patent Application Publication Nos. 2011/0200568 to Ikeda et al., 2010/0156778 to Egusa et al., 2012/0276070 to Musick, and 2012/0276636 to Nakagawa, Shi et al., *Cell Stem Cell* 3 (5): 568-574 (2008), Kim et al., *Nature* 454:646-650 (2008), Kim et al., *Cell* 136 (3): 411-419 (2009), Huangfu et al., *Nature Biotechnology* 26:1269-

1275 (2008), Zhao et al., *Cell Stem Cell* 3:475-479 (2008), Feng et al., *Nature Cell Biology* 11:197-203 (2009), and Hanna et al., *Cell* 133 (2): 250-264 (2008), which are hereby incorporated by reference in their entirety. Methods of driving the iPSCs toward a glial progenitor cell (GPC) fate and on to an astrocyte fate are described herein and known in the art, see e.g., Wang et al., "Human iPSC-Derived Oligodendrocyte Progenitor Cells can Myelinate and Rescue a Mouse Model of Congenital Hypomyelination," *Cell Stem Cell* 12:252-264 (2013), which is hereby incorporated by reference in its entirety.

In another embodiment, glial cells having impaired $K^+$ uptake are glial cells of a subject having a neuropsychiatric disorder. A "neuropsychiatric disorder" as referred to herein, includes any brain disorder with psychiatric symptoms including, but not limited to, dementia, amnesic syndrome, and personality-behavioral changes. Exemplary neuropsychiatric disorders involving impaired $K^+$ channel function and impaired $K^+$ uptake in glial cells that are suitable for treatment using the methods described herein include, without limitation, schizophrenia, autism spectrum disorders, and bipolar disorder.

Thus, another aspect of the present disclosure relates to a method of treating or inhibiting the onset of a neuropsychiatric disorder in a subject. This method involves selecting a subject having or at risk of having a neuropsychiatric disorder, and administering, to the selected subject, a inhibitor under conditions effective to treat or inhibit the onset of the neuropsychiatric disorder in the subject. In some embodiments, the REST inhibitor is a glial cell targeted REST inhibitor.

In one embodiment, the methods described herein are utilized to treat a subject having schizophrenia. Schizophrenia is a chronic and severe mental disorder that affects how an individual thinks, feels, and behaves. To date, there have been several suggested staging models of the disorder (Agius et al., "The Staging Model in Schizophrenia, and its Clinical Implications," *Psychiatr. Danub.* 22 (2): 211-220 (2010); McGorry et al., "Clinical Staging: a Heuristic Model and Practical Strategy for New Research and Better Health and Social Outcomes for Psychotic and Related Disorders," *Can. J. Psychiatry* 55 (8): 486-497 (2010); Fava and Kellner, "Staging: a Neglected Dimension in Psychiatric Classification," *Acta Psychiatr. Scand.* 87:225-230 (1993), which are hereby incorporated by reference in their entirety). However, generally, schizophrenia develops in at least three stages: the prodromal phase, the first episode, and the chronic phase. There is also heterogeneity of individuals at all stages of the disorder, with some individuals considered ultra-high risk, clinical-high risk, or at-risk for the onset of psychosis (Fusar-Poli et al., "The Psychosis High-Risk State: a Comprehensive State-of-the-Art Review," *JAMA Psychiatry* 70:107-120 (2013), which is hereby incorporated by reference in its entirety).

The methods described herein are suitable for treating a subject in any stage of schizophrenia, and at any risk level of psychosis, as all stages will involve impaired glial cell $K^+$ uptake. For example, in one embodiment, a subject treated in accordance with the methods described herein is a subject that is at risk for developing schizophrenia. Such a subject may have one or more genetic mutations in one or more genes selected from ABCA13, ATK1, C4A, COMT, DGCR2, DGCR8, DRD2, MIR137, NOS1AP, NRXN1, OLIG2, RTN4R, SYN2, TOP3B YWHAE, ZDHHC8, or chromosome 22 (22q11) that have been associated with the development of schizophrenia and may or may not be exhibiting any symptoms of the disease. In another embodiment, the subject may be in the prodromal phase of the disease and exhibiting one or more early symptoms of schizophrenia, such as anxiety, depression, sleep disorders, and/or brief intermittent psychotic syndrome. In another embodiment, the subject being treated in accordance with the methods described herein is experiencing psychotic symptoms, e.g., hallucinations, paranoid delusions, of schizophrenia.

In another embodiment, the methods describe herein are utilized to treat a subject having autism or a related disorder. Related disorders include, without limitation, Asperger's disorder, Pervasive Developmental Disorder-Not Otherwise Specified, Childhood Disintegrative Disorder, and Rett's Disorder, which vary in the severity of symptoms including difficulties in social interaction, communication, and unusual behaviors (McPartland et al., "Autism and Related Disorders," *Handb Clin Neurol* 106:407-418 (2012), which is hereby incorporated by reference in its entirety). The methods described herein are suitable for the treatment of each one of these conditions and at any stage of the condition. In one embodiment, the subject being treated in accordance with the methods described herein does not exhibit any symptoms of autism or a related condition. In another embodiment, the subject being treated exhibits one or more early symptoms of autism or a related condition. In yet another embodiment, the subject being treated in accordance with the methods described herein exhibits a multitude of symptoms of autism or a related condition.

In another embodiment, the methods describe herein are utilized to treat a subject having bipolar disorder. Bipolar disorder is a group of conditions characterized by chronic instability of mood, circadian rhythm disturbances, and fluctuations in energy level, emotion, sleep, and views of self and others. Bipolar disorders include, without limitation, bipolar disorder type I, bipolar disorder type II, cyclothymic disorder, and bipolar disorder not otherwise specified.

Generally, bipolar disorders are progressive conditions which develop in at least three stages: the prodromal phase, the symptomatic phase, and the residual phase (Kapczinski et al., "Clinical Implications of a Staging Model for Bipolar Disorders," *Expert Rev Neurother* 9:957-966 (2009), and McNamara et al., "Preventative Strategies for Early-Onset Bipolar Disorder: Towards a Clinical Staging Model," *CNS Drugs* 24:983-996 (2010); which are hereby incorporated by reference in their entirety). The methods described herein are suitable for treating subjects having any of the aforementioned bipolar disorders and subjects in any stage of a particular bipolar disorder. For example, in one embodiment, the subject treated in accordance with the methods described herein is a subject at the early prodromal phase exhibiting symptoms of mood lability/swings, depression, racing thoughts, anger, irritability, physical agitation, and anxiety. In another embodiment, the subject treated in accordance with the methods described herein is a subject at the symptomatic phase or the residual phase.

As used herein, the term "subject" and "patient" expressly includes human and non-human mammalian subjects. The term "non-human mammal" as used herein extends to, but is not restricted to, household pets and domesticated animals. Non-limiting examples of such animals include primates, cattle, sheep, ferrets, mice, rats, swine, camels, horses, poultry, fish, rabbits, goats, dogs and cats.

In accordance with the present disclosure, an inhibitor of REST is administered to glial cells having impaired $K^+$ uptake, which may be the result of impaired channel expression and/or function. In another embodiment, a REST inhibitor is administered to a subject having impaired glial cell $K^+$ uptake. REST is a Krüppel-type zinc finger transcription factor that represses target gene activity upon binding to a 21-nucleotide DNA sequence called repressor element-1 (RE1) that is located in the target gene. REST is the key component of a nuclear complex that includes the other core factors of SIN3A, SIN3B, and RCOR1, and epigenetic regulators such as histone deacetylases (HDACs), histone methyltransferase (EHMT2), and histone-demethylase (KDM1A).

At least four isoforms of human REST exist as a result of alternative splicing. The amino acid sequence of human REST isoform 1 (UniProt identifier Q13127-1) is provided below as SEQ ID NO: 1 below.

```
Met Ala Thr Gln Val Met Gly Gln Ser Ser Gly Gly Gly Gly Leu Phe
1               5                   10                  15

Thr Ser Ser Gly Asn Ile Gly Met Ala Leu Pro Asn Asp Met Tyr Asp
            20                  25                  30

Leu His Asp Leu Ser Lys Ala Glu Leu Ala Ala Pro Gln Leu Ile Met
        35                  40                  45

Leu Ala Asn Val Ala Leu Thr Gly Glu Val Asn Gly Ser Cys Cys Asp
    50                  55                  60

Tyr Leu Val Gly Glu Glu Arg Gln Met Ala Glu Leu Met Pro Val Gly
65                  70                  75                  80

Asp Asn Asn Phe Ser Asp Ser Glu Glu Gly Glu Gly Leu Glu Glu Ser
                85                  90                  95

Ala Asp Ile Lys Gly Glu Pro His Gly Leu Glu Asn Met Glu Leu Arg
            100                 105                 110

Ser Leu Glu Leu Ser Val Val Glu Pro Gln Pro Val Phe Glu Ala Ser
        115                 120                 125

Gly Ala Pro Asp Ile Tyr Ser Ser Asn Lys Asp Leu Pro Pro Glu Thr
    130                 135                 140

Pro Gly Ala Glu Asp Lys Gly Lys Ser Ser Lys Thr Lys Pro Phe Arg
145                 150                 155                 160

Cys Lys Pro Cys Gln Tyr Glu Ala Glu Ser Glu Glu Gln Phe Val His
                165                 170                 175

His Ile Arg Val His Ser Ala Lys Lys Phe Phe Val Glu Glu Ser Ala
            180                 185                 190

Glu Lys Gln Ala Lys Ala Arg Glu Ser Gly Ser Ser Thr Ala Glu Glu
        195                 200                 205

Gly Asp Phe Ser Lys Gly Pro Ile Arg Cys Asp Arg Cys Gly Tyr Asn
    210                 215                 220

Thr Asn Arg Tyr Asp His Tyr Thr Ala His Leu Lys His His Thr Arg
225                 230                 235                 240

Ala Gly Asp Asn Glu Arg Val Tyr Lys Cys Ile Ile Cys Thr Tyr Thr
                245                 250                 255

Thr Val Ser Glu Tyr His Trp Arg Lys His Leu Arg Asn His Phe Pro
            260                 265                 270

Arg Lys Val Tyr Thr Cys Gly Lys Cys Asn Tyr Phe Ser Asp Arg Lys
        275                 280                 285

Asn Asn Tyr Val Gln His Val Arg Thr His Thr Gly Glu Arg Pro Tyr
    290                 295                 300

Lys Cys Glu Leu Cys Pro Tyr Ser Ser Ser Gln Lys Thr His Leu Thr
305                 310                 315                 320

Arg His Met Arg Thr His Ser Gly Glu Lys Pro Phe Lys Cys Asp Gln
                325                 330                 335

Cys Ser Tyr Val Ala Ser Asn Gln His Glu Val Thr Arg His Ala Arg
            340                 345                 350

Gln Val His Asn Gly Pro Lys Pro Leu Asn Cys Pro His Cys Asp Tyr
        355                 360                 365

Lys Thr Ala Asp Arg Ser Asn Phe Lys Lys His Val Glu Leu His Val
    370                 375                 380
```

-continued

```
Asn Pro Arg Gln Phe Asn Cys Pro Val Cys Asp Tyr Ala Ala Ser Lys
385                 390                 395                 400

Lys Cys Asn Leu Gln Tyr His Phe Lys Ser Lys His Pro Thr Cys Pro
                405                 410                 415

Asn Lys Thr Met Asp Val Ser Lys Val Lys Leu Lys Lys Thr Lys Lys
            420                 425                 430

Arg Glu Ala Asp Leu Pro Asp Asn Ile Thr Asn Glu Lys Thr Glu Ile
        435                 440                 445

Glu Gln Thr Lys Ile Lys Gly Asp Val Ala Gly Lys Lys Asn Glu Lys
    450                 455                 460

Ser Val Lys Ala Glu Lys Arg Asp Val Ser Lys Glu Lys Lys Pro Ser
465                 470                 475                 480

Asn Asn Val Ser Val Ile Gln Val Thr Thr Arg Thr Arg Lys Ser Val
                485                 490                 495

Thr Glu Val Lys Glu Met Asp Val His Thr Gly Ser Asn Ser Glu Lys
            500                 505                 510

Phe Ser Lys Thr Lys Lys Ser Lys Arg Lys Leu Glu Val Asp Ser His
        515                 520                 525

Ser Leu His Gly Pro Val Asn Asp Glu Glu Ser Ser Thr Lys Lys Lys
    530                 535                 540

Lys Lys Val Glu Ser Lys Ser Lys Asn Asn Ser Gln Glu Val Pro Lys
545                 550                 555                 560

Gly Asp Ser Lys Val Glu Glu Asn Lys Lys Gln Asn Thr Cys Met Lys
                565                 570                 575

Lys Ser Thr Lys Lys Lys Thr Leu Lys Asn Lys Ser Ser Lys Lys Ser
            580                 585                 590

Ser Lys Pro Pro Gln Lys Glu Pro Val Glu Lys Gly Ser Ala Gln Met
        595                 600                 605

Asp Pro Pro Gln Met Gly Pro Ala Pro Thr Glu Ala Val Gln Lys Gly
    610                 615                 620

Pro Val Gln Val Glu Pro Pro Pro Pro Met Glu His Ala Gln Met Glu
625                 630                 635                 640

Gly Ala Gln Ile Arg Pro Ala Pro Asp Glu Pro Val Gln Met Glu Val
                645                 650                 655

Val Gln Glu Gly Pro Ala Gln Lys Glu Leu Leu Pro Pro Val Glu Pro
            660                 665                 670

Ala Gln Met Val Gly Ala Gln Lys Glu Leu Leu Pro Pro Val Glu Pro
        675                 680                 685

Pro Pro Met Glu Thr Ala Gln Thr Glu Val Ala Gln Met Gly Pro Ala
    690                 695                 700

Pro Met Glu Pro Ala Gln Met Glu Val Ala Gln Val Glu Ser Ala Pro
705                 710                 715                 720

Met Gln Val Val Gln Lys Glu Pro Val Gln Met Glu Leu Ser Pro Pro
                725                 730                 735

Met Glu Val Val Gln Lys Glu Pro Val Gln Ile Glu Leu Ser Pro Pro
            740                 745                 750

Met Glu Val Val Gln Lys Glu Pro Val Lys Ile Glu Leu Ser Pro Pro
        755                 760                 765

Ile Glu Val Val Gln Lys Glu Pro Val Gln Met Glu Leu Ser Pro Pro
    770                 775                 780

Met Gly Val Val Gln Lys Glu Pro Ala Gln Arg Glu Pro Pro Pro Pro
785                 790                 795                 800

Arg Glu Pro Pro Leu His Met Glu Pro Ile Ser Lys Lys Pro Pro Leu
                805                 810                 815
```

-continued

```
Arg Lys Asp Lys Lys Glu Lys Ser Asn Met Gln Ser Glu Arg Ala Arg
            820                 825                 830

Lys Glu Gln Val Leu Ile Glu Val Gly Leu Val Pro Val Lys Asp Ser
        835                 840                 845

Trp Leu Leu Lys Glu Ser Val Ser Thr Glu Asp Leu Ser Pro Pro Ser
    850                 855                 860

Pro Pro Leu Pro Lys Glu Asn Leu Arg Glu Glu Ala Ser Gly Asp Gln
865                 870                 875                 880

Lys Leu Leu Asn Thr Gly Glu Gly Asn Lys Glu Ala Pro Leu Gln Lys
                885                 890                 895

Val Gly Ala Glu Glu Ala Asp Glu Ser Leu Pro Gly Leu Ala Ala Asn
            900                 905                 910

Ile Asn Glu Ser Thr His Ile Ser Ser Ser Gly Gln Asn Leu Asn Thr
        915                 920                 925

Pro Glu Gly Glu Thr Leu Asn Gly Lys His Gln Thr Asp Ser Ile Val
    930                 935                 940

Cys Glu Met Lys Met Asp Thr Asp Gln Asn Thr Arg Glu Asn Leu Thr
945                 950                 955                 960

Gly Ile Asn Ser Thr Val Glu Glu Pro Val Ser Pro Met Leu Pro Pro
                965                 970                 975

Ser Ala Val Glu Glu Arg Glu Ala Val Ser Lys Thr Ala Leu Ala Ser
            980                 985                 990

Pro Pro Ala Thr Met Ala Ala Asn Glu Ser Gln Glu Ile Asp Glu Asp
        995                 1000                1005

Glu Gly Ile His Ser His Glu Gly Ser Asp Leu Ser Asp Asn Met
    1010                1015                1020

Ser Glu Gly Ser Asp Asp Ser Gly Leu His Gly Ala Arg Pro Val
    1025                1030                1035

Pro Gln Glu Ser Ser Arg Lys Asn Ala Lys Glu Ala Leu Ala Val
    1040                1045                1050

Lys Ala Ala Lys Gly Asp Phe Val Cys Ile Phe Cys Asp Arg Ser
    1055                1060                1065

Phe Arg Lys Gly Lys Asp Tyr Ser Lys His Leu Asn Arg His Leu
    1070                1075                1080

Val Asn Val Tyr Tyr Leu Glu Glu Ala Ala Gln Gly Gln Glu
    1085                1090                1095
```

The nucleotide sequence encoding human REST isoform-1 is provided below as SEQ ID NO: 2 (NCBI Reference Sequence identifier NM_005612.4).

```
ggcggcggcg gcggcgcgga ctgggtgcgc ggcgcagcgt cctgtgttgg aatgtgcggc    60

tgccgcgagc tcgcggcgca gcagcggagc gagcgccgcc gaggcccggg gccccagacc   120

ctggcggcgg ctgccgcagc cgagacggca gggcgaggcc cggaggcctg agcaccctct   180

gcagccccac tcctgggcct tcttggtcca cgacggcccc agcacccaac tttaccaccc   240

tcccccacct ctcccccgaa actccagcaa caaagaaaag tagtcggaga aggagcggcg   300

actcagggtc gcccgcccct cctcaccgag gaaggccgaa tacagttatg gccacccagg   360

taatggggca gtcttctgga ggaggagggc tgtttaccag cagtggcaac attggaatgg   420

ccctgcctaa cgacatgtat gacttgcatg acctttccaa agctgaactg gccgcacctc   480

agcttattat gctggcaaat gtggccttaa ctggggaagt aaatggcagc tgctgtgatt   540

acctggtcgg tgaagaaaga cagatggcag aactgatgcc ggttggggat aacaactttt   600
```

-continued

```
cagatagtga agaaggagaa ggacttgaag agtctgctga tataaaaggt gaacctcatg  660
gactggaaaa catggaactg agaagtttgg aactcagcgt cgtagaacct cagcctgtat  720
ttgaggcatc aggtgctcca gatatttaca gttcaaataa agatcttccc cctgaaacac  780
ctggagcgga ggacaaaggc aagagctcga agaccaaacc ctttcgctgt aagccatgcc  840
aatatgaagc agaatctgaa gaacagtttg tgcatcacat cagagttcac agtgctaaga  900
aatttttttgt ggaagagagt gcagagaagc aggcaaaagc cagggaatct ggctcttcca  960
ctgcagaaga gggagatttc tccaagggcc ccattcgctg tgaccgctgc ggctacaata 1020
ctaatcgata tgatcactat acagcacacc tgaaacacca caccagagct ggggataatg 1080
agcgagtcta caagtgtatc atttgcacat acacaacagt gagcgagtat cactggagga 1140
aacatttaag aaaccatttt ccaaggaaag tatacacatg tggaaaatgc aactattttt 1200
cagacagaaa aaacaattat gttcagcatg ttagaactca tacaggagaa cgcccatata 1260
aatgtgaact ttgtccttac tcaagttctc agaagactca tctaactaga catatgcgta 1320
ctcattcagg tgagaagcca tttaaatgtg atcagtgcag ttatgtggcc tctaatcaac 1380
atgaagtaac ccgccatgca agacaggttc acaatgggcc taaacctctt aattgcccac 1440
actgtgatta caaaacagca gatagaagca acttcaaaaa acatgtagag ctacatgtga 1500
acccacggca gttcaattgc cctgtatgtg actatgcagc ttccaagaag tgtaatctac 1560
agtatcactt caaatctaag catcctactt gtcctaataa aacaatggat gtctcaaaag 1620
tgaaactaaa gaaaaccaaa aaacgagagg ctgacttgcc tgataatatt accaatgaaa 1680
aaacagaaat agaacaaaca aaaataaaag gggatgtggc tggaaagaaa aatgaaaagt 1740
ccgtcaaagc agagaaaaga gatgtctcaa aagagaaaaa gccttctaat aatgtgtcag 1800
tgatccaggt gactaccaga actcgaaaat cagtaacaga ggtgaaagag atggatgtgc 1860
atacaggaag caattcagaa aaattcagta aaactaagaa aagcaaaagg aagctggaag 1920
ttgacagcca ttctttacat ggtcctgtga atgatgagga atcttcaaca aaaaagaaaa 1980
agaaggtaga aagcaaatcc aaaaataata gtcaggaagt gccaaagggt gacagcaaag 2040
tggaggagaa taaaaagcaa aatacttgca tgaaaaaaag tacaaagaag aaaactctga 2100
aaaataaatc aagtaagaaa agcagtaagc ctcctcagaa ggaacctgtt gagaagggat 2160
ctgctcagat ggaccctcct cagatggggc ctgctcccac agaggcggtt cagaaggggc 2220
ccgttcaggt ggagccgcca cctcccatgg agcatgctca gatggagggt gcccagatac 2280
ggcctgctcc tgacgagcct gttcagatgg aggtggttca ggaggggcct gctcagaagg 2340
agctgctgcc tcccgtggag cctgctcaga tggtgggtgc ccaaattgta cttgctcaca 2400
tggagctgcc tcctcccatg gagactgctc agacggaggt tgcccaaatg ggccctgctc 2460
ccatggaacc tgctcagatg gaggttgccc aggtagaatc tgctcccatg caggtggtcc 2520
agaaggagcc tgttcagatg gagctgtctc ctcccatgga ggtggtccag aaggagcctg 2580
ttcagataga gctgtctcct cccatggagg tggtccagaa ggaacctgtt aagatagagc 2640
tgtctcctcc catagaggtg gtccagaagg agcctgttca gatggagttg tctcctccca 2700
tgggggtggt tcagaaggag cctgctcaga gggagccacc tcctcccaga gagcctcccc 2760
ttcacatgga gccaatttcc aaaaagcctc ctctccgaaa agataaaaag gaaaagtcta 2820
acatgcagag tgaaagggca cggaaggagc aagtccttat tgaagttggc ttagtgcctg 2880
ttaaagatag ctggcttcta aaggaaagtg taagcacaga ggatctctca ccaccatcac 2940
caccactgcc aaaggaaaat ttaagagaag aggcatcagg agaccaaaaa ttactcaaca 3000
```

-continued

```
caggtgaagg aaataaagaa gcccctcttc agaaagtagg agcagaagag gcagatgaga 3060
gcctacctgg tcttgctgct aatatcaacg aatctaccca tatttcatcc tctggacaaa 3120
acttgaatac gccagagggt gaaactttaa atggtaaaca tcagactgac agtatagttt 3180
gtgaaatgaa aatggacact gatcagaaca caagagagaa tctcactggt ataaattcaa 3240
cagttgaaga accagtttca ccaatgcttc ccccttcagc agtagaagaa cgtgaagcag 3300
tgtccaaaac tgcactggca tcacctcctg ctacaatggc agcaaatgag tctcaggaaa 3360
ttgatgaaga tgaaggcatc cacagccatg aaggaagtga cctaagtgac aacatgtcag 3420
agggtagtga tgattctgga ttgcatgggg ctcggccagt tccacaagaa tctagcagaa 3480
aaaatgcaaa ggaagccttg gcagtcaaag cggctaaggg agattttgtt tgtatcttct 3540
gtgatcgttc tttcagaaag ggaaaagatt acagcaaaca cctcaatcgc catttggtta 3600
atgtgtacta tcttgaagaa gcagctcaag ggcaggagta atgaaacttt gaacaaggtt 3660
tcagttctta gtttgtaagg tatattacat tttatattca tttatgatag cagacaacct 3720
tttaagattg ctttaattag tatctgatgt tgatttttaa gtggcattct tttccttagg 3780
actttttatg tatacctgtt gattgttgtg taaattttag taaatctaag agagtgtact 3840
aaaccagcag gtatctgtta gcttatgtgt ttaattgaaa ttagaaggct aagatggtat 3900
aacagcattt tattgctttg tccagctaca acttgtcatt tttttctcca tgtcttatct 3960
tcctgtttca ctttagttta ttcttcgttt tttattgaga tctataaaaa attggcttac 4020
ttaatagcaa attacttgaa gaatttgcct gctttatata aagttagcac tttaagattt 4080
tttttttag agatgagaag acatttaaat tgaagaaaaa ttcccccagc aatagacagt 4140
ctatcagtcc aagtatttac ttcctgagtt ttgatcaata tttttattt gtgtatgtta 4200
atcgtcataa aaacagtgat tttggtgtgt tttttatttt ggtgctttaa tggcttaaga 4260
tgttgcacat tttttttttc ttttggtttc tgtttatgtt tttttgccta tgcagttaaa 4320
tttttcctag aaatagcatt tgtgttgaac agtaacactt tatacatata tatatgcatg 4380
tttattttgt ttggcgtctt tggagggatg cttttagact tgtttgcaaa agggcagttt 4440
tctttttctt tgctgcagtt gtctattttg cagaataata gtgtgtgcaa gtttgtgagc 4500
aaatgaaata tgcaggttca atctattgat tttgattttt acatcttata tctatgccag 4560
aatctgtatt tcatataact tatttatttc gaatggatgt agtaaattca cagctatcag 4620
ttttgatttt gcaataaata aaccactagg ttgcatgtcg aacaaatttt tatctcaaat 4680
accaaccatc agtttttttt ttcatgtgtt ttggtacagc taattcctaa ttgtagagtg 4740
ttaaatgttt gaggagaacc ttttctcata gatggttggt gttcatatgg ctactttaca 4800
ataaagagaa ctgtaagtga tatttggaaa ctacaaacct ggaattagga gatataatta 4860
ttccttcaag ttttatagaa tatcacttgg gagattccaa agccatagct attacgcggc 4920
aaacctagga taagaaaggt agtatgagtg ctggtagacc agctgcaact ttcctataca 4980
gtgaaaaagg ctggtgaaac aagtacagtc cagatttttt aaaatcatac tttctcaggg 5040
atctccacaa actggtgggt gtcctggctg tctgtgtgat agcctctttc tataggtgag 5100
gcctcaaatg aattgcagct atcctggtgt tcctatgagg gcactttgta tgaaaaaggg 5160
catgtactcc aaaacatttt tgtaggttct ttggccagtt gccaaagagt gtgaaagaat 5220
ccaatagagg atttttctta ctgatagcag tcattcattg cagtaaaata aaatatgatc 5280
ccattaggga atcttgaatt ctgacctccc atactccgtt ttgaaataac cactttatat 5340
ttcatttttt aaaaatctga tgatctcttt gaggcaggtt tcagatttgg cagtacaaca 5400
tgaaagatta ggaaaagcat taataacgtg tgggtggaaa gcttgttaaa aatctgagag 5460
```

-continued

```
tgaagtttga gttaaaagtt gtttgaacat ggcattgact gggaggccaa agatttaaag 5520
aagcggaaga ttcttctctt aagacatgag gagtaagttg tgtgataatg gtatgtgttt 5580
tgtgtgcatg aatggacatt gtaaatgttg aattctaggc tccgacaatc attgtcaaca 5640
gaagatcaag ctgcaaatat ttatgtttta aaacttaaat tataaagcta gttaagtctt 5700
tctaatgact agttttaatg ttcatgggta cattttacct aagttaccgt ttacattgta 5760
tagaaaaaga tacatcttaa gcacagattg gttattagga attagtttgg ggaagaggtt 5820
tttttgtgga ttctttcata ctgcaaagaa aaaccatttg ccttttgggg aattgagcta 5880
acttctaatc tagtcttaag actagaatgc taaaaacaaa aacatgaagg aaattaaaac 5940
cccttattat taaattgatt tgtaaaaaca ttgttactgg aaatttattg gacttgaggc 6000
cttcctccag aaaataagga cttgattgtc aggcctatat taggttctga accttaatgc 6060
catgtatttg tacttactaa aaattgtttc aatgaaaagt acattagcag tatgaacttc 6120
tggtccagtt ggaagttttt ccatttgaaa aatgtgatgt ttgcatggaa ctgtttgaaa 6180
ctttttttatt ttctagtccc cctcccccac actggataga atttagccta gaattttccc 6240
tttggataaa agaacaaaaa ttgaacatgt tatttgtaaa ttgatgttta gtaattagtg 6300
ataaacttga aatactagca tatattataa gccttaatct taggtagtct tatgaaaatg 6360
aatctcttaa ctatcttttg aacctgtatt cacattggtt ttcaagatat tttaagttat 6420
atttttttcct cttttcagag ctgcttctta ttctggggct actttttttt ttagttgtgt 6480
aattcacaaa gggctgcatt tttttttttt tttaataagg cttataacta tggctggatc 6540
ttttgctcta gtcttctaag aagggccatt ttatttttta gagtcacttc taaagtcatg 6600
tggtaattaa ctttggagac tgttttgcgt atgagtgctg atacaaatta aaacccaagt 6660
agacctcatt gcatgtcacc ctatgaatgt tgacaatgga aggaatacct tgcctgtagt 6720
atactgtcac ttctggattg ataagctgag gaagaaagtt aagtttcttt tttacataag 6780
tcagaaaaac ttacagctgg tgttcctagt ttcctggttg acctcagcag atgaagtgaa 6840
cagatagtgt taattcagat tgaagaaatt atctgaatct tggtttgtgt agatttacaa 6900
tctacatgca atattaacta aatcagatag cttttacagt ttcacatgtg tacataggtt 6960
ccctcccggt cccttccata tccattagtt attgaacttt ctaaactggc attgaaacat 7020
tacaacaatg ttttgttgca ccaattttat aaacttaagc agtgcaatac gtgttacttt 7080
tctgaggcaa accaaaggta aatttctcaa ggttcttgct gccttcttta gcagcatttg 7140
atggaagatc ttttatacat ttgtaataga taaaaataaa ccagattgca aatccttttt 7200
taaaatccta aaccatgtac caagtttttg gtccaaatta tgtaggataa gttaaactta 7260
aattgcattc tattaaccaa tatgagtgta tttctgtaag catagttatg ttgaaataaa 7320
gttttaaaaa cca                                                   7333
```

In one embodiment, a suitable REST inhibitor is any agent or compound capable of decreasing the level of REST expression in a glial cell relative to the level of REST expression occurring in the absence of the agent. In one embodiment, therapeutic agents that are suitable for inhibiting or decreasing the level of REST expression in glial cells include, without limitation inhibitory nucleic acid molecules such as a REST antisense oligonucleotide, a REST shRNA, a REST siRNA, and a REST RNA aptamer.

The use of antisense methods to inhibit the in vivo translation of genes and subsequent protein expression is well known in the art (e.g., U.S. Pat. No. 7,425,544 to Dobie et al.; U.S. Pat. No. 7,307,069 to Karras et al.; U.S. Pat. No. 7,288,530 to Bennett et al.; U.S. Pat. No. 7,179,796 to Cowsert et al., which are hereby incorporated by reference in their entirety). In accordance with the present disclosure, suitable antisense nucleic acids are nucleic acid molecules (e.g., molecules containing DNA nucleotides, RNA nucleotides, or modifications (e.g., modification that increase the stability of the molecule, such as 2'-O-alkyl (e.g., methyl) substituted nucleotides) or combinations thereof) that are complementary to, or that hybridize to, at least a portion of a specific nucleic acid molecule encoding REST (see e.g., Weintraub, H. M., "Antisense DNA and RNA," Scientific Am. 262:40-46 (1990), which is hereby incorporated by reference in its entirety). SEQ ID NO: 2 above is an exemplary nucleic acid molecule encoding REST. Variant nucleic acid molecules encoding REST are also known in the art, see e.g., NCBI Ref. Seq. NM_001363453 and NM_001193508.1, which are hereby incorporated by reference in their entirety, and are suitable for use in the design of inhibitory nucleic acid antisense molecules. Suitable antisense oligonucleotides for use in the method described herein are, or are up to 12, 13, 14, 15, 16, 17, 18, 19, 20, 21, 22, 23, 24, 25, 26, 27, 28, 29, or 30 nucleobases in length and comprise no more than 6, no more than 5, no more than 4, no more than 3, no more than 2, or no more than 1 non-complementary nucleobase(s) relative to the target REST nucleic acid, or specified portion thereof. The antisense nucleic acid molecule hybridizes to its corresponding target REST nucleic acid molecule, to form a double-stranded molecule, which interferes with translation of the mRNA, as the cell will not translate a double-stranded mRNA.

REST antisense nucleic acids can be introduced into cells as antisense oligonucleotides, or can be produced in a cell in which a nucleic acid encoding the antisense nucleic acid has been introduced, for example, using gene therapy methods. Anti-REST antisense oligonucleotides suitable for use in accordance with the methods described herein are disclosed in WO2011031998 to Sedaghat et al., which is hereby incorporated by reference in its entirety.

REST siRNAs are double stranded synthetic RNA molecules approximately 20-25 nucleotides in length with short 2-3 nucleotide 3' overhangs on both ends. The double stranded siRNA molecule represents the sense and antisense strand of a portion of the target mRNA molecule, in this case a portion of the REST nucleotide sequence, i.e., SEQ ID NO: 2 encoding REST isoform 1 or a portion of the nucleotide sequence of another REST isoform (i.e., NCBI Ref. Seq. Nos. NM_001363453 and NM_001193508.1, which are hereby incorporated by reference in their entirety). siRNA molecules are typically designed to target a region of the REST mRNA target approximately 50-100 nucleotides downstream from the start codon. Upon introduction into a cell, the siRNA complex triggers the endogenous RNA interference (RNAi) pathway, resulting in the cleavage and degradation of the target REST mRNA molecule. siRNA molecules that target REST and other members of the REST transcription complex that can be utilized in the methods described herein are disclosed in WO2009027349 to Maes, which is hereby incorporated by reference in its entirety. Various improvements of siRNA compositions, such as the incorporation of modified nucleosides or motifs into one or both strands of the siRNA molecule to enhance stability, specificity, and efficacy, have been described and are suitable for use in accordance with this aspect of the disclosure (see e.g., WO2004/015107 to Giese et al.; WO2003/070918 to McSwiggen et al.; WO1998/39352 to Imanishi et al.; U.S. Patent Application Publication No. 2002/0068708 to Jesper et al.; U.S. Patent Application Publication No. 2002/0147332 to Kaneko et al; U.S. Patent Application Publication No. 2008/0119427 to Bhat et al., which are hereby incorporated by reference in their entirety).

Short or small hairpin RNA molecules are similar to siRNA molecules in function, but comprise longer RNA sequences that make a tight hairpin turn. shRNA is cleaved by cellular machinery into siRNA and gene expression is silenced via the cellular RNA interference pathway. shRNA molecules that effectively interfere with REST expression have been developed, as described herein, and comprise the following nucleic acid sequences: 5'-CCAUUCCAAUGUUGCCACUGC-3' (SEQ ID NO: 3) targeting the REST nucleotide sequence of 5'-GCAGTGGCAACATTGGAATGG-3' (SEQ ID NO: 4) and 5'-UCGAUUAGUAUUGUAGCCG-3' (SEQ ID NO: 5) targeting the REST nucleotide sequence of 5'-CGGCTACAATACTAATCGA-3' (SEQ ID NO: 6)

Nucleic acid aptamers that specifically bind to REST are also suitable for use in the methods as described herein. Nucleic acid aptamers are single-stranded, partially single-stranded, partially double-stranded, or double-stranded nucleotide sequences, capable of specifically recognizing a selected target molecule, either protein or nucleic acid molecule, by a mechanism other than Watson-Crick base pairing or triplex formation. Aptamers include, without limitation, defined sequence segments and sequences comprising nucleotides, ribonucleotides, deoxyribonucleotides, nucleotide analogs, modified nucleotides, and nucleotides comprising backbone modifications, branchpoints, and non-nucleotide residues, groups, or bridges. An exemplary RNA aptamer known to inhibit REST, which is suitable for use in the accordance with the methods described herein comprises a double stranded RNA molecule as shown below, that contains a sequence corresponding to a 21 base pair DNA element known as the neuron-restrictive silencer element (NRSE) or RE1 (Kuwabara et al., "A Small Modulatory dsRNA Specifies the Fate of Adult Neural Stem Cells," *Cell* 116:779-793 (2004), which is hereby incorporated by reference in its entirety.

Exemplary RNA REST Aptamer

5'-UUCAGCACCACGGACAGCGCC-3' (SEQ ID NO: 7)

3'-AAGUCGUGGUGCCUGUCGCGG-5' (SEQ ID NO: 8)

Modifications to inhibitory nucleic acid molecules described herein, i.e., REST antisense oligonucleotides, siRNA, shRNA, PNA, aptamers, encompass substitutions or changes to internucleoside linkages, sugar moieties, or nucleobases. Modified inhibitory nucleic acid molecules are often preferred over native forms because of desirable properties such as, for example, enhanced cellular uptake, enhanced affinity for nucleic acid target, increased stability in the presence of nucleases, or increased inhibitory activity. For example, chemically modified nucleosides may be employed to increase the binding affinity of a shortened or truncated antisense oligonucleotide for its target nucleic acid. Consequently, comparable results can often be obtained with shorter antisense compounds that have such chemically modified nucleosides.

REST targeted inhibitory nucleic acid molecules can optionally contain one or more nucleosides wherein the sugar group has been modified. Such sugar modified nucleosides may impart enhanced nuclease stability, increased binding affinity or some other beneficial biological property to the nucleic acid molecule. In certain embodiments, nucleosides comprise a chemically modified ribofuranose ring moieties. Examples of chemically modified ribofuranose rings include without limitation, addition of substituted groups, including 5' and 2' substituent groups, bridging of non-geminal ring atoms to form bicyclic nucleic acids (BNA), replacement of the ribosyl ring oxygen atom with S, N(R), or C(R1)(R)2, where R=H, $C_1$-$C_{12}$ alkyl or a protecting group, and combinations thereof. Examples of chemically modified sugars include 2'-F-5'-methyl substituted nucleoside, replacement of the ribosyl ring oxygen atom with S with further substitution at the 2'-position.

In certain embodiments, nucleosides are modified by replacement of the ribosyl ring with a sugar surrogate (sometimes referred to as DNA analogs), such as a morpholino ring, a cyclohexenyl ring, a cyclohexyl ring, or a tetrahydropyranyl ring.

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to REST inhibitor nucleic acid molecules. Modified nucleobases include synthetic and natural nucleobases such as, for example, 5-methylcytosine (5-me-C). Certain nucleobase substitutions, including 5-methylcytosine substitutions, are particularly useful for increasing the binding affinity of a nucleic acid molecule to its target nucleic acid. Additional modified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl, 7-methyl guanine and 7-methyladenine, 2-F-adenine, 2-aminoadenine, 8-azaguanine and 8-azaadenine, 7-deazaguanine, 7-deazaadenine, 3-deazaguanine, and 3-deazaadenine.

The naturally occurring internucleoside linkage of RNA and DNA is a 3' to 5' phosphodiester linkage. Inhibitory nucleic acid molecules having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparing phosphorous-containing and non-phosphorous-containing linkages are well known. In certain embodiments, an inhibitory nucleic acid molecule targeting a REST nucleic acid comprises one or more modified internucleoside linkages.

The inhibitory nucleic acid molecules described here may be covalently linked to one or more moieties or conjugates which enhance the activity, cellular distribution, or cellular uptake of the resulting inhibitory nucleic acid molecule. Typical conjugate groups include cholesterol moieties and lipid moieties. Additional conjugate groups include carbohydrates, polymers, peptides, inorganic nanostructured materials, phospholipids, biotin, phenazine, folate, phenanthridine, anthraquinone, acridine, fluoresceins, rhodamines, coumarins, and dyes.

Inhibitory nucleic acid molecules described herein can also be modified to have one or more stabilizing groups, e.g., cap structures, that are generally attached to one or both termini of the inhibitory nucleic acid molecule to enhance properties such as, for example, nuclease stability. These terminal modifications protect inhibitory nucleic acid molecules from exonuclease degradation, and can help in delivery and/or localization within a cell. Cap structures can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an inhibitory nucleic acid molecule to impart nuclease stability include those disclosed in WO 03/004602 to Manoharan, which is hereby incorporated by reference in its entirety.

In another embodiment, a suitable REST inhibitor is any agent or compound capable of decreasing or preventing the level of nuclear translocation of REST in a glial cell relative to the level of REST nuclear translocation occurring in the absence of the agent.

In another embodiment, a suitable REST inhibitor is any agent or compound capable of antagonizing or decreasing REST suppressor activity in a glial cell relative to the level of REST suppressor activity occurring in the absence of the agent. Agents suitable to achieve REST inhibition in this manner include nucleic acid molecules that encode the DNA binding domain of REST, but lack the two repressor domains of the protein. These agents act as dominant negative REST agents, blocking the interaction of REST with its RE1 sequence in a target gene. Suitable REST dominant negative nucleic acid molecules that can be utilized in the methods described herein are disclosed in Chen et al., "NRSF/REST is Required in vivo for Repression of Multiple Neuronal Target Genes During Embryogenesis," *Nat. Genet.* 20:136-42 (1998) and Roopra et al., "Transcriptional Repression by Neuron-restrictive Silencer Factor is Mediated via the Sin3-histone Deacetylase Complex," *Mol Cell Biol* 20:2147-57 (2000), which are hereby incorporated by reference in their entirety).

In another embodiment, the agent capable of decreasing REST suppressor activity in a glial cell is a benzoimidazole-5-carboxamide derivative (Charbord et al., High Throughput Screening for Inhibitors of REST in Neural Derivatives of Human Embryonic Stem Cells Reveals a Chemical Compound that Promotes Expression of Neuronal Genes," *Stem Cells* 31:1816-1828 (2013), which is hereby incorporated by reference in its entirety). Particularly suitable benzoimidazole-5-carboxamide derivatives include, without limitation, 2-(2-Hydroxy-phenyl)-1H-benzoimidazole-5-carboxylic acid allyloxy-amide (X5050) and 2-Thiophen-2-yl-1H-benzoimidazole-5-carboxylic acid (2-ethyl-hexyl)-amide (X5917).

In another embodiment, the agent capable of decreasing REST suppressor activity in a glial cell is a pyrazole propionamide derivative (Charbord et al., High Throughput Screening for Inhibitors of REST in Neural Derivatives of Human Embryonic Stem Cells Reveals a Chemical Compound that Promotes Expression of Neuronal Genes," *Stem Cells* 31:1816-1828 (2013), which is hereby incorporated by reference in its entirety). Particularly suitable pyrazole propionamide derivatives include, without limitation, 3-[1-(3-Bromo-phenyl)-3,5-dimethyl-1H-pyrazol-4-yl]-1-{4-[5-(morpholine-4-carbonyl)-pyridin-2-yl]-2-phenyl-piperazin-1-yl}-propan-1-one (X38210), and 3-[1-(2,5-Difluoro-phenyl)-3,5-dimethyl-1H-pyrazol-4-yl]-1-{4-[5-(morpholine-4-carbonyl)-pyridin-2-yl]-2-phenyl-piperazin-1-yl}-propan-1-one (X38207).

In another embodiment, the agent capable of decreasing REST suppressor activity in a glial cell is an antibody or an antibody fragment that binds to and blocks the activity of REST directly, or that binds to any of the proteins of the transcriptional repressor complex and inhibits the formation of the REST transcription complex in a glial cell. Antibodies capable of binding REST and methods of making the same are disclosed in U.S. Pat. No. 6,824,774 to Anders and Schoenherr, which is hereby incorporated by reference in its entirety. Monoclonal antibodies suitable for inhibiting the formation of the REST transcription complex, thereby inhibiting the activity of REST repression include antibodies against BRG-1 associated factor (BAF) 57, BRG1, and BAF170 (Battaglioli et al., "REST Repression of Neuronal Gene Requires Components of the hSWI.SNF Complex," *J. Biol. Chem.* 277 (43): 41038-45 (2002), which is hereby incorporated by reference in its entirety). Other REST complex components that can be inhibited via antibody binding include, without limitation, MeCP2, mSin3a, AOF2, RCOR1, and JARID1C.

In another embodiment, a suitable REST inhibitor is any agent or compound that inhibits the formation of the REST transcriptional complex in a glial cell. REST-mediated gene repression is achieved by the recruitment of two separate corepressor complexes, i.e., N-terminal and C-terminal corepressor complexes (see Ooi et al., "Chromatin Crosstalk in Development and Disease: Lessons from REST," *Nat Rev Genet* 8:544-54 (2007), which is hereby incorporated by reference in its entirety). Thus, agents or compounds that inhibit the activity of components of these co-repressor complexes are suitable for inhibiting the activity of REST. For example, the histone deacetylases, HDAC1 and HDAC2, are required at both the N-terminal and C-terminal corepressor complexes. Thus, agents that inhibit the activity of these HDACs to inhibit REST activity are suitable for use in the methods described herein. Suitable HDAC inhibitors include, without limitation, valproic acid (VPA), trichostatin A (TSA), suberoylanilide hydroxamic acid (SAHA), N-Hydroxy-4-(Methyl {[5-(2-Pyridinyl)-2-Thienyl] Sulfonyl}Amino) Benzamide,4-Dimethylamino-N-(6 Hydroxycarbamoyethyl) Benzamide-N-Hydroxy-7-(4-Dimethylaminobenzoyl) Aminoheptanamide, 7-[4-(Dimethylamino) Phenyl]-N-Hydroxy-4,6-Dimethyl-7-Oxo-2,4-Heptadienamide, Docosanol, (5)-[5-Acetylamino-1-(2-oxo-4-trifluoromethyl-2H-chromen-7-ylcarbamoyl) pentyljcarbamic acid tert-butyi ester (BATCP), Benzyl ((S)-[1-(4-methyl-2-oxo-2H-chromen-7-ylcarbamoyl)-5-propionyl aminopentyljcarbamate (MOCPAC), and 4-(Dimethylamino)-N-[7-(hydroxyamino)-7-oxoheptyl]-benzamide (M344). Other suitable HDAC inhibitors that can be utilized in the methods described herein to inhibit REST activity are disclosed in WO2009/027349 to Maes et al., which is hereby incorporated by reference in its entirety.

In another embodiment, the REST complex is inhibited using an agent that inhibits the function of other members of the repression complex, including MeCP2, mSin3a, AOF2, RCOR1, JARID1C, BAF57, BAF170, and BRG1. Such agents act by preventing the transcriptional repression complex from binding to the gene promoter or act by preventing members of the complexes from interacting with each other. Suitable agents include inhibitory nucleic acid molecules, e.g., antisense oligonucleotides, siRNA, shRNA, aptamers, as described above, antibodies, and small molecule inhibitors.

In one embodiment, the REST inhibitor used in accordance with the methods described herein is packaged into a nanoparticle delivery vehicle to effectuate delivery of the inhibitor to glial cells of a subject, i.e., a glial cell targeted REST inhibitor. Suitable nanoparticle delivery vehicles for delivering REST inhibitors across the blood brain barrier and/or to glial cells include, without limitation, liposome, protein nanoparticles, polymeric nanoparticles, metallic nanoparticles, and dendrimers.

Liposomes are spherical vesicles composed of phospholipid and steroid (e.g., cholesterol) bilayers that are about 80-300 nm in size. Liposomes are biodegradable with low immunogenicity. The REST inhibitor as described herein can be incorporated into liposomes using the encapsulation process. The liposomes are taken up by target cells by adsorption, fusion, endocytosis, or lipid transfer. Release of the REST inhibitor from the liposome depends on the liposome composition, pH, osmotic gradient, and surrounding environment. The liposome can be designed to release the REST inhibitor in a cell organelle specific manner to achieve, for example, nuclear delivery of the REST inhibitor.

Methods and types of liposomes that can be utilized to deliver the REST inhibitors described herein to glial cells are known in the art, see e.g., Liu et al., "Paclitaxel loaded liposomes decorated with a multifunctional tandem peptide for glioma targeting," *Biomaterials* 35:4835-4847 (2014); Gao et al. "Glioma targeting and blood-brain barrier penetration by dual-targeting doxorubincin liposomes," *Biomaterials* 34:5628-5639 (2013); Zong et al., "Synergistic dual-ligand doxorubicin liposomes improve targeting and therapeutic efficacy of brain glioma in animals," *Mol Pharm.* 11:2346-2357 (2014); Yemisci et al., "Systemically administered brain-targeted nanoparticles transport peptides across the blood-brain barrier and provide neuroprotection," *J Cerebr Blood F Met.* 35:469-475 (2015), which are hereby incorporated by reference in their entirety.

In another embodiment, the REST inhibitors described herein are packaged in a polymeric delivery vehicle. Polymeric delivery vehicles are structures that are typically about 10 to 100 nm in diameter. Suitable polymeric nanoparticles for encapsulating the REST inhibitors as described herein can be made of synthetic polymers, such as poly-ε-caprolactone, polyacrylamine, and polyacrylate, or natural polymers, such as, e.g., albumin, gelatin, or chitosan. The polymeric nanoparticles used herein can be biodegradable, e.g., poly(L-lactide) (PLA), polyglycolide (PGA), poly(lactic acid-co-glycolic acid) (PLGA), or non-biodegradable, e.g., polyurethane. The polymeric nanoparticles used herein can also contain one or more surface modifications that enhance delivery. For example, in one embodiment, the polymeric nanoparticles are coated with nonionic surfactants to reduce immunological interactions as well as intermolecular interactions. The surfaces of the polymeric nanoparticles can also be functionalized for attachment or immobilization of one or more targeting moieties as described infra, e.g., an antibody or other binding polypeptide or ligand that directs the nanoparticle across the blood brain barrier and/or to glial cells for glial cell uptake (i.e., glia progenitor or astrocyte uptake).

Methods and types of polymeric nanoparticles that can be utilized to deliver the REST inhibitors as described herein to glial cells are known in the art, see e.g., Koffie et al. "Nanoparticles enhance brain delivery of blood-brain barrier-impermeable probes for in vivo optical and magnetic resonance imaging," *Proc Natl Acad Sci USA.* 108:18837-18842 (2011); Zhao et al., "The permeability of puerarin loaded poly(butylcyanoacrylate) nanoparticles coated with polysorbate 80 on the blood-brain barrier and its protective effect against cerebral ischemia/reperfusion injury," *Biol Pharm Bull.* 36:1263-1270 (2013); Yemisci et al., "Systemically administered brain-targeted nanoparticles transport peptides across the blood-brain barrier and provide neuroprotection," *J Cerebr Blood F Met.* 35:469-475 (2015), which are hereby incorporated by reference in their entirety.

In another embodiment, the composition of the present disclosure is packaged in a dendrimer nanocarrier delivery vehicle. Dendrimers are unique polymers with a well defined size and structure. Exemplary nanometric molecules having dendritic structure that are suitable for use as a delivery vehicle for the REST inhibitor as described herein include, without limitation, glycogen, amylopectin, and proteoglycans. Methods of encapsulating therapeutic compositions, such as the composition described herein, in the internal structure of dendrimers are known in the art, see e.g., D'Emanuele et al., "Dendrimer-drug interactions," *Adv Drug Deliv Rev* 57:2147-2162 (2005), which is hereby incorporated by reference in its entirety. The surface of dendrimers is suitable for the attachment of one or more targeting moieties, such as antibodies or other binding proteins and/or ligands as described herein capable of targeting the dendrimers across the blood brain barrier and/or to glial cells.

An exemplary dendrimer for encapsulation of a REST inhibitor for administration and delivery to a subject in need thereof is poly(amido amide) (PAMAM). PAMAM has been utilized for the delivery of both protein and nucleic acid therapeutics to target cells of interest. Methods of encapsulating therapeutic agents in PAMAM and utilization of PAMAM for delivering therapeutic agents to the central nervous system are also known in the art and can be utilized herein, see e.g., Cerqueira et al., "Multifunctionalized CMCht/PAMAM dendrimer nanoparticles modulate the cellular uptake by astrocytes and oligodendrocytes in primary cultures of glial cells," *Macromol Biosci.* 12:591-597 (2012); Nance et al., "Systemic dendrimer-drug treatment of ischemia-induced neonatal white matter injury," *J Control Release* 214:112-120 (2015); Natali et al., "Dendrimers as drug carriers: dynamics of PEGylated and methotrexate-loaded dendrimers in aqueous solution," *Macromolecules* 43:3011-3017 (2010); Han et al., "Peptide conjugated PAMAM for targeted doxorubicin delivery to transferrin receptor overexpressed tumors," *Mol Pharm* 7:2156-2165 (2010); Kannan et al., "Dendrimer-based Postnatal Therapy for Neuroinflammation and Cerebral Palsy in a Rabbit Model," *Sci. Transl. Med.* 4:130 (2012); and Singh et al., "Folate and Folate-PEG-PAMAM dendrimers: synthesis, characterization, and targeted anticancer drug delivery potential in tumor bearing mice," *Bioconjugate Chem* 19, 2239-2252 (2008), which is hereby incorporated by reference in its entirety.

In another embodiment, the REST inhibitor as disclosed herein is packaged in a silver nanoparticle or an iron oxide nanoparticle. Methods and preparations of silver and iron oxide nanoparticles that can be utilized to deliver a REST inhibitor described herein to glia cells are known in the art, see e.g, Hohnholt et al., "Handling of iron oxide and silver nanoparticles by astrocytes," *Neurochem Res.* 38:227-239 (2013), which is hereby incorporated by reference in its entirety.

In another embodiment, a REST inhibitor as described herein is packaged in gold nanoparticles. Gold nanoparticles are small particles (<50 nm) that enter cells via an endocytic pathway. In one embodiment, the gold nanoparticles are coated with glucose to facilitate transfer of the nanoparticles across the blood brain barrier and uptake of the nanoparticles by astrocytes via the GLUT-1 receptor as described by Gromnicova et al., "Glucose-coated Gold Nanoparticles Transfer across Human Brain Endothelium and Enter Astrocytes In vitro," *PLoS ONE* 8 (12): e81043 (2013), which is hereby incorporated by reference in its entirety.

In another embodiment, the composition of the present disclosure is packaged in silica nanoparticles. Silica nanoparticles are biocompatible, highly porous, and easily functionalized. Silica nanoparticles are amorphous in shape, having a size range of 10-300 nm. Silica nanoparticles that are suitable to deliver a therapeutic composition, such as a REST inhibitor to the CNS for glial cell uptake are known in the art, see e.g., Song et al., "In vitro Study of Receptor-mediated Silica Nanoparticles Delivery Across Blood Brain Barrier," *ACS Appl. Mater. Interfaces* 9 (24): 20410-20416 (2017); Tamba et al., "Tailored Surface Silica Nanoparticles for Blood-Brain Barrier Penetration: Preparation and In vivo Investigation," *Arabian J. Chem. doi.org/*10.1016/j.arabjc.2018.03.019 (2018), which are hereby incorporated by reference in their entirety.

In another embodiment, the REST inhibitor is packaged into a protein nanoparticle delivery vehicle. Protein nanoparticles are biodegradable, metabolizable, and are easily amenable to modification to allow entrapment of therapeutic molecules or compositions and attachment of targeting molecules if desired. Suitable protein nanoparticle delivery vehicles that are known in the art and have been utilized to deliver therapeutic compositions to the central nervous system include, without limitation, albumin particles (see e.g., Lin et al., "Blood-brain Barrier Penetrating Albumin Nanoparticles for Biomimetic Drug Delivery via Albumin-Binding Protein Pathway for Antiglioma Therapy," *ACS Nano* 10 (11): 9999-10012 (2016), and Ruan et al., "Substance P-modified Human Serum Albumin Nanoparticles Loaded with Paclitaxel for Targeted Therapy of Glioma," *Acta Pharmaceutica Sinica* B 8 (1): 85-96 (2018), which are hereby incorporated by reference in their entirety), gelatin nanoparticles (see e.g., Zhao et al., "Using Gelatin Nanoparticle Mediated Intranasal Delivery of Neuropeptide Substance P to Enhance Neuro-Recovery in Hemiparkinsoninan Rats," *PLoS One* 11 (2): e0148848 (2016), which is hereby incorporated by reference in its entirety), and lactoferrin nanoparticles (see e.g., Kumari et al., "Overcoming Blood Brain Barrier with Dual Purpose Temozolomide Loaded Lactoferrin Nanoparticles for Combating Glioma (SERP-17-12433)," *Scientific Reports* 7:6602 (2017), which is hereby incorporated by reference in its entirety).

Nanoparticle mediated delivery of a therapeutic composition can be achieved passively (i.e., based on the normal distribution pattern of liposomes or nanoparticles within the body) or by actively targeting delivery. Actively targeted delivery involves modification of the delivery vehicle's natural distribution pattern by attaching a targeting moiety to the outside surface of the liposome. In one embodiment, a delivery vehicle as described herein is modified to include one or more targeting moieties, i.e., a targeting moiety that facilitates delivery of the liposome or nanoparticle across the blood brain barrier and/or a targeting moiety that facilitates glial cell uptake (i.e., glial progenitor cell uptake and/or astrocyte uptake). In one embodiment, a delivery vehicle as described herein is surface modified to express a targeting moiety suitable for achieving blood brain barrier penetration. In another embodiment, a delivery vehicle as described herein is surface modified to express a targeting moiety suitable for glial cell uptake. In another embodiment, a delivery vehicle as described herein is surface modified to express dual targeting moieties.

Targeting moieties that facilitate delivery of the liposome or nanoparticle across the blood brain barrier take advantage of receptor-mediated, transporter-mediated, or adsorptive-mediated transport across the barrier. Suitable targeting moieties for achieving blood brain barrier passage include antibodies and ligands that bind to endothelial cell surface proteins and receptors. Exemplary targeting moieties include, without limitation, cyclic RGD peptides (Liu et al, "Paclitaxel loaded liposomes decorated with a multifunctional tandem peptide for glioma targeting," *Biomaterials* 35:4835-4847 (2014), which is hereby incorporated by reference in its entirety), a cyclic A7R peptide that binds to VEGFR2 and neuropilin-1 (Ying et al., "A Stabilized Peptide Ligand for Multifunctional Glioma Targeted Drug Delivery," *J. Contr. Rel.* 243:86-98 (2016), which is hereby incorporated by reference in its entirety), a transferrin protein, peptide, or antibody capable of binding to the transferrin receptors (Zong et al., "Synergistic dual-ligand doxorubicin liposomes improve targeting and therapeutic efficacy of brain glioma in animals," *Mol Pharm.* 11:2346-235773 (2014); Yemisci et al., "Systemically administered brain-targeted nanoparticles transport peptides across the blood-brain barrier and provide neuroprotection," *J Cerebr Blood F Met.* 35:469-475 (2015); and Wei et al., "Brain Tumor-targeted Therapy by Systemic Delivery of siRNA with Transferrin Receptor-Mediated Core-Shell Nanoparticles," *Inter. J. Pharm* 510 (1): 394-405), Niewoehner et al., "Increased Brain Penetration and Potency of a Therapeutic Antibody Using a Monovalent Molecular Shuttle," *Neuron* 81:49-60 (2014), which are hereby incorporated by reference in in their entirety), a folate protein or peptide that binds the folate receptor (Gao et al. "Glioma targeting and blood-brain barrier penetration by dual-targeting doxorubincin liposomes," *Biomaterials* 34:5628-5639 (2013), which is hereby incorporated by reference in its entirety), a lactoferrin protein or peptide that binds the lactoferrin receptor (Song et al., "In vitro Study of Receptor-mediated Silica Nanoparticles Delivery Across Blood Brain Barrier," *ACS Appl. Mater. Interfaces* 9 (24): 20410-20416 (2017), which is hereby incorporated by reference in its entirety), low density lipoprotein receptor ligands, such ApoB and ApoE (Wagner et al., "Uptake Mechanisms of ApoE-modified Nanoparticles on Brain Capillary Endothelial Cells as a Blood-brain Barrier Model," *PLoS One* 7: e32568 (2012), which is hereby incorporated by reference in its entirety), substance P peptide (Ruan et al., "Substance P-modified Human Serum Albumin Nanoparticles Loaded with Paclitaxel for Targeted Therapy of Glioma," *Acta Pharmaceutica Sinica B* 8 (1): 85-96 (2018), which is hereby incorporated by reference in its entirety), and an angiopep-2 (An2) peptide (Demeule et al., "Conjugation of a brain-penetrant peptide with neurotensin provides antinociceptive properties," *J. Clin. Invest.* 124:1199-1213 (2014), which is hereby incorporated by reference in its entirety). Other suitable targeting moieties include ligands of the amino acid transporters, e.g., glutathione for transport via the glutathione transporter (Rip et al., "Glutathione PEGylated Liposomes: Pharmacokinetics and Delivery of Cargo Across the Blood-Brain Barrier in Rats," *J. Drug Target* 22:460-67 (2014), which is hereby incorporated be reference in its entirety), and choline derivatives for delivery via the choline transporter (Li et al., "Choline-derivative-modified Nanoparticles for Brain-targeting Gene Delivery," *Adv. Mater.* 23:4516-20 (2011), which is hereby incorporated by reference in its entirety).

A second targeting moiety is one that facilitates glial cell delivery and uptake. Suitable targeting moieties to effectuate astrocyte uptake include, without limitation, low density lipoprotein (LDL) receptor ligands or peptides thereof capable of binding the LDL receptor and oxidized LDL receptor on astrocytes (Lucarelli et al, "The Expression of Native and Oxidized LDL Receptors in Brain Microvessels is Specifically Enhanced by Astrocyte-derived Soluble Factor(s)," *FEBS Letters* 522 (1-3): 19-23 (2002), which is hereby incorporated by reference in its entirety), glucose or other glycans capable of binding the GLUT-1 receptor on astrocytes (Gromnicova et al., "Glucose-coated Gold Nanoparticles Transfer across Human Brain Endothelium and Enter Astrocytes In vitro," *PLoS ONE* 8 (12): e81043 (2013), which is hereby incorporated by reference in its entirety), and platelet derived growth factor or peptide thereof capable of binding PDGFRα of glial progenitor cells.

Glial cell delivery of inhibitory nucleic acid molecules as described herein, e.g., REST antisense oligonucleotides, REST siRNA, REST shRNA, can also be achieved by packaging such nucleic acid molecules in viral vectors. Several viral vectors are known to inherently target astrocytes in vivo, e.g., lentiviral vectors (Colin et al., "Engineered Lentiviral Vector Targeting Astrocytes In vivo," *Glia* 57:667-679 (2009), and Cannon et al., "Pseudotype-dependent Lentiviral Transduction of Astrocytes or Neurons in the Rat Substantia Nigra," *Exp. Neurol.* 228:41-52 (2011), which are hereby incorporated by reference in their entirety), and adeno-associated virus vectors (Furman et al., "Targeting Astrocytes Ameliorates Neurologic Changes in a Mouse Model of Alzheimer's Disease," *J. Neurosci.* 32:16129-40 (2012), which is hereby incorporated by reference in its entirety), and are thus suitable for effectuating delivery of the nucleic acid REST inhibitory molecules in accordance with the methods described herein.

As used herein, "treating" or "treatment" includes the administration of a REST inhibitor to restore or derepress, partially or wholly, potassium channel gene expression in glial cells, restore, partially or wholly, potassium channel uptake activity in glial cells, and restore, partially or wholly, potassium homeostasis in glial cells and the surrounding tissue. With respect to treating a subject having a neuropsychiatric condition, "treating" includes any indication of success in amelioration of the condition, including any objective or subjective parameter such as abatement, remission, diminishing of symptoms (e.g., decreasing neuronal excitability), or making the condition more tolerable to the patient (e.g., seizure incident); slowing the progression of the condition; making the condition less debilitating; or improving a subject's physical or mental well-being. The treatment or amelioration of symptoms can be based on objective or subjective parameters; including the results of a physical examination, neurological examination, and/or psychiatric evaluation.

As referred to herein "under conditions effective" refers to the effective dose, route of administration, frequency of administration, formulation of REST inhibitor, etc. that play a role in achieving the desired therapeutic benefit for the subject. An effective dose of a REST inhibitor to restore $K^+$ uptake by glial cells in a subject and/or to treat or inhibit the onset of a neuropsychiatric disorder in a subject is the dose of a REST inhibitor that is effective to derepress potassium channel gene expression partially or wholly, which in turn will restore potassium channel uptake function (partially or wholly) to permit restoration of brain potassium homeostasis. In instances where the REST inhibitor is administered to a subject having a neuropsychiatric disorder, such as schizophrenia, an effective dose is the dose that restores brain potassium homeostasis to a level sufficient to decrease the extracellular levels of potassium, decrease neuronal excitability, and/or decrease seizure incident. A dosage effective to treat a subject having a neuropsychiatric disorder is the dosage effective to improve disordered cognition in the subject. The effective dose for a particular subject varies, for example, depending upon the health and physical condition of the individual to be treated, the mental and emotional capacity of the individual, the stage of the disorder, the type of REST inhibitor, the route of administration, the formulation, the attending physician's assessment of the medical situation, and other relevant factors.

In one embodiment, the glial cells having impaired $K^+$ uptake are glial progenitor cells. As demonstrated in the Examples herein, REST upregulation in glial progenitor cells suppresses $K^+$ channel gene expression and subsequently $K^+$ uptake by glial progenitor cells. The decrease in $K^+$ uptake inhibits terminal glial progenitor cell differentiation. Thus, in one embodiment, an effective dose of a REST inhibitor is the dose that potentiates astroglial maturation by glial progenitor cells, which reduces, eliminates, or inhibits the onset of a neuropsychiatric disease, symptoms of the neuropsychiatric disease, or side effects of a disease.

In another embodiment, the glial cells having impaired $K^+$ uptake are astrocytes. REST inhibition in astrocytes restores $K^+$ uptake and subsequent $K^+$ homeostasis in the affected astrocytes. REST inhibition in astrocytes of a subject having a neuropsychiatric disease (where potassium channel expression and function is altered) reduces neuronal excitability, decreases seizure incidence, and improves disordered cognition. Thus, treatment with an effective dose of a REST inhibitor decreases, alleviates, arrests, or inhibits development of the symptoms or conditions associated with schizophrenia, autism spectrum disorder, bipolar disorder, or any other neuropsychiatric disorder. Treatment may be prophylactic to prevent or delay the onset or worsening of the disease, condition or disorder, or to prevent the manifestation of clinical or subclinical symptoms thereof. Alternatively, treatment may be therapeutic to suppress and/or alleviate symptoms after the manifestation of the disease, condition or disorder.

A REST inhibitor useful for restoring glial cell $K^+$ uptake in a subject, for example, in a subject having a neuropsychiatric condition, may be administered parenterally via intracerebral delivery, intrathecal delivery, intranasal delivery, or via direct infusion into brain ventricles.

In one embodiment, parenteral administration is by infusion. Infused REST inhibitors may be delivered with a pump. In certain embodiments, broad distribution of the infused REST inhibitor is achieved by delivery to the cerebrospinal fluid by intracranial administration, intrathecal administration, or intracerebroventricular administration.

In certain embodiments, an infused REST inhibitor is delivered directly to a tissue. Examples of such tissues include the striatal tissue, the intracerebroventricular tissue, and the caudate tissue. Specific localization of a REST inhibitor may be achieved by direct infusion to a targeted tissue.

In some embodiments, parenteral administration is by injection. The injection may be delivered with a syringe or a pump. In certain embodiments, the injection is a bolus administered directly to a tissue. Examples of such tissues include the striatal tissue, the intracerebroventricular tissue, and the caudate tissue. Specific localization of pharmaceutical agents, including antisense oligonucleotides, can be achieved via injection to a targeted tissue.

In some embodiments, specific localization of the REST inhibitor, such as a REST antisense oligonucleotide, to a targeted tissue improves the pharmacokinetic profile of the inhibitor as compared to broad diffusion of the same. The specific localization of the REST inhibitor improves potency compared to broad diffusion of the inhibitor, requiring administration of less inhibitor to achieve similar pharmacology. "Similar pharmacology" refers to the amount of time that the target REST mRNA and/or target REST protein is down-regulated/inhibited (e.g. duration of action). In certain embodiments, methods of specifically localizing a REST inhibitor, such as by bolus injection, decreases median effective concentration (EC50) of the inhibitor by a factor of about 20.

In another embodiment, the REST inhibitor as described herein is co-administered with one or more other pharmaceutical agents. According to this embodiment of the disclosure, such one or more other pharmaceutical agents are designed to treat the same disease, disorder, or condition, or one or more symptoms associated therewith, as the REST inhibitor described herein. In one embodiment, the one or more other pharmaceutical agents are designed to treat an undesired side effect of one or more pharmaceutical compositions of the present disclosure. In one embodiment, a REST inhibitor as described herein is co-administered with another pharmaceutical agent to treat an undesired effect. In another embodiment, a REST inhibitor as described herein is co-administered with another pharmaceutical agent to produce a combinational effect. In another embodiment, a REST inhibitor as described herein is co-administered with another pharmaceutical agent to produce a synergistic effect.

In one embodiment, a REST inhibitor as described herein and another pharmaceutical agent are administered at the same time. In another embodiment a REST inhibitor as described herein and another pharmaceutical agent are administered at different times. In another embodiment, a REST inhibitor as described herein and another pharmaceutical agent are prepared together in a single formulation. In another embodiment, a REST inhibitor as described herein and another pharmaceutical agent are prepared separately.

In some embodiments, pharmaceutical agents that may be co-administered with a REST inhibitor as described herein include antipsychotic agents, such as, e.g., haloperidol, chlorpromazine, clozapine, quetapine, and olanzapine; antidepressant agents, such as, e.g., fluoxetine, sertraline hydrochloride, venlafaxine and nortriptyline; tranquilizing agents such as, e.g., benzodiazepines, clonazepam, paroxetine, venlafaxin, and beta-blockers; and mood-stabilizing agents such as, e.g., lithium, valproate, lamotrigine, and carbamazepine.

Preferences and options for a given aspect, feature, embodiment, or parameter of the invention should, unless the context indicates otherwise, be regarded as having been disclosed in combination with any and all preferences and options for all other aspects, features, embodiments, and parameters of the invention.

EXAMPLES

Materials and Methods

Patient identification, protection and sampling. Patients from which induced pluripotent stem cell (iPSC) derived glial progenitor cells (GPCs) were derived were diagnosed with disabling degrees of schizophrenia with onset in early adolescence. All patients and their guardians were consented/assented by a child and adolescent psychiatrist and under an approved protocol of the University Hospitals Case Medical Center Institutional Review Board, blinded as to subsequent line designations. No study investigators had access to patient identifiers.

Cell sources and lines Schizophrenia-derived iPSC lines were produced from subjects with childhood-onset schizophrenia, and control lines were produced from age- and gender-appropriate control subjects. All iPSC lines were derived as previously reported (Windrem et al., "Human iPSC Glial Mouse Chimeras Reveal Glial Contributions to Schizophrenia," *Cell Stem Cell* 21:195-208.e6 (2017), which is hereby incorporated by reference in its entirety). An additional control line (C27) was generously provided by Dr. Lorenz Studer (Memorial Sloan-Kettering). Control-derived lines included: CWRU-22, -17, -37, -208, and C27; SCZ-derived lines included CWRU-8, -51, -52, -193, -164, -29, -30, and -31 (Table 1). CWRU-51/52 and CWRU-29/30/31 comprised different lines from the same patients, and were assessed to estimate inter-line variability from single patients. All iPSCs were generated from fibroblasts by retroviral expression of Cre-excisable Yamanaka factors (Oct4, Sox2, Klf4, c-Myc) (Takahashi et al., "Induction of Pluripotent Stem Cells From Adult Human Fibroblasts by Defined Factors," *Cell* 131:861-872 (2007), which is hereby incorporated by reference in its entirety), with validation of pluripotency and karyotypic stability as described (Windrem et al., "Human iPSC Glial Mouse Chimeras Reveal Glial Contributions to Schizophrenia," *Cell Stem Cell* 21:195-208.e6 (2017), which is hereby incorporated by reference in its entirety).

TABLE 1

| Patient-derived iPSC lines used in this study | | | | | | | |
|---|---|---|---|---|---|---|---|
| Subject number | hiPSC Line(s) | Age of subject | Gender | Ethnicity | RNA-Seq of GPCs | Astrocytic differentiation | Potassium uptake |
| | Control Subjects | | | | | | |
| CTR 1 | 22 | 26 | M | C | √ | √ | √ |
| CTR 2 | 37 | 32 | F | AA | √ | √ | √ |
| CTR 3 | 208 | 25 | M | C | √ | √ | √ |
| CTR 4 | C27 | NA | NA | NA | √ | √ | √ |
| | Schizophrenic Subjects | | | | | | |
| SCZ 1 | 51 | 16 | M | C | √ | √ | √ |
| SCZ 2 | 29, 30, 31 | 12 | M | C | √ | √ | √ |
| SCZ 3 | 193 | 15 | F | NA | | √ | √ |
| SCZ 4 | 164 | 14 | F | AA | √ | √ | √ |
| SCZ 5 | 8 | 10 | F | C | √ | | |

The lines used in this study were previously described and published in Windrem et al., "Human iPSC Glial Mouse Chimeras Reveal Glial Contributions to Schizophrenia," *Cell Stem Cell* 21:195-208.e6 (2017), which is hereby incorporated by reference in its entirety 2017. The additional mainpulations added in the present study - astrocytic differentiation and assessment of $K^+$ uptake by the resultant differentiated astrocytes - are noted in the two most right-hand columns.

hiPSC culture and passage. hiPSCs were cultured on irradiated mouse embryonic fibroblasts (MEFs), in 0.1% gelatin coated 6-well plates with 1-1.2 million cells/well in hES medium (see below) supplemented with 10 ng/ml bFGF (Invitrogen, 13256-029). Media changes were performed daily, and cells passaged at 80% confluence, after 4-7 days of culture. For hiPSC passage, cells were first incubated with 1 ml collagenase (Invitrogen, 17104-019) at 37° C. for 3-5 minutes, and then cells were transferred into a 15 ml tube for centrifuge with 3 minutes. The pellet was re-suspended with ES medium with bFGF, and was plated onto new irradiated MEFs at 1:3-1:4.

GPC and astrocytic generation from hiPSCs. When hiPSCs reached 80% confluence, they were incubated with 1 ml Dispase (Invitrogen, 17105-041) to permit the generation of embryoid bodies (EBs); these were cultured in ES medium without bFGF for 5 days. At DIV6, EBs were plated onto poly-ornithine (Sigma, P4957) and laminin (VWR, 47743)-coated dishes, and cultured in neural induction media (NIM; see below) (Wang et al., "Human iPSC-Derived Oligodendrocyte Progenitor Cells Can Myelinate and Rescue a Mouse Model of Congenital Hypomyelination," *Cell Stem Cell* 12:252-264 (2013), which is hereby incorporated by reference in its entirety), supplemented with 20 ng/ml bFGF, 2 μg/ml heparin and 10 μg/ml laminin for 10 days.

At DIV25, the EBs were gently scraped with a 2 ml glass pipette, then cultured in NIM plus 1 μM purmorphamine (Calbiochem, 80603-730) and 0.1 μM RA (Sigma, R2625). At DIV33, NPCs appeared and were serially switched to NIM with 1 μM purmorphamine and 10 ng/ml bFGF for 7 days, followed by glial induction medium (GIM) (Wang et al., "Human iPSC-Derived Oligodendrocyte Progenitor Cells Can Myelinate and Rescue a Mouse Model of Congenital Hypomyelination," *Cell Stem Cell* 12:252-264 (2013), which is hereby incorporated by reference in its entirety), with 1 μM purmorphamine for another 15 days. At DIV56, the resultant glial spheres were mechanically cut with microsurgical blades under a dissection microscope, and switched to GIM with 10 ng/ml PDGF, 10 ng/ml IGF, and 10 ng/ml NT3, with media changes every 2 days. At DIV150-180, GPCs were incubated with mouse anti-CD44 microbeads (1:50), and then incubated with rabbit anti-mouse IgG2a+b micro-beads (1:100) and further sorted by magnetic cell sorting (MACS) with a magnetic stand column. The $CD44^+$ cells were then directed into astrocytes in M41 supplemented with 10% FBS plus 20 ng/mL BMP4 for 3 weeks.

Media recipes are listed in Table 2 (base, hESC and neural media) and Table 3 (Glial and Astrocyte induction media).

TABLE 2

| Media formulas: Base, hESC and Neural media | | | |
|---|---|---|---|
| Component | Concentration | Vendor | Catalog |
| MEF medium | | | |
| Dulbecco's Modified Eagle Medium | 1X | Invitrogen | 11965-092 |
| Fetal Bovine Serum | 10% | Invitrogen | 16000-044 |
| Non-Essential Amino Acid | 1X | Invitrogen | 11140-050 |
| hES medium | | | |
| Dulbecco's Modified Eagle Medium/Nutrient Mixture F-12 | 1X | Invitrogen | 11330-032 |
| KnockOut Serum Replacement | 20% | Invitrogen | 10828-028 |
| L-glutamine | 1 mM | Invitrogen | 25030-081 |
| 2-Mercaptoethanol | 0.1 mM | Sigma | M7522 |
| Non-Essential Amino Acid | 1X | Invitrogen | 11140-050 |
| Neural induction medium | | | |
| Dulbecco's Modified Eagle Medium/Nutrient Mixture F-12 | 1X | Invitrogen | 11330-032 |

TABLE 2-continued

| Media formulas: Base, hESC and Neural media | | | |
|---|---|---|---|
| Component | Concentration | Vendor | Catalog |
| Non-Essential Amino Acid | 1X | Invitrogen | 11140-050 |
| N2 Supplement | 1X | Invitrogen | 17502-048 |
| Recombinant human FGF-2 protein | 20 ng/ml | Sigma | F0291 |
| Heparin Solution | 2 μg/ml | Fisher Scientific | NC0668440 |
| Laminin | 10 μg/ml | Fisher Scientific | CB-40232 |

TABLE 3

| Media formulas: Glial and astrocytic induction media | | | |
|---|---|---|---|
| Component | Concentration | Vendor | Catalog |
| Glial medium | | | |
| Dulbecco's Modified Eagle Media/F12 | 1X | Invitrogen | 11330-032 |
| B27 Supplement | 1X | Invitrogen | 12587-010 |
| N1 Supplement | 1X | Sigma | N6530 |
| Non-Essential Amino Acid | 1X | Invitrogen | 11140-050 |
| Triiodo-L-Thyronine (T3) | 60 ng/ml | Sigma | T5516-1mg |
| N6,2-O-Dibutyryl cyclic AMP | 1 μM | Sigma | D0260 |
| Biotin | 100 ng/ml | Sigma | B4639 |
| Recombinant human PDGF-AA | 10 ng/ml | R&D | 221-AA-50 |
| Recombinant human IGF-1 protein | 10 ng/ml | R&D | 291-G1-050 |
| Recombinant human NT3 protein | 10 ng/ml | R&D | 267-N3-025 |
| Antibiotic-Antimycotic | 0.5X | Invitrogen | 15240-096 |
| Astrocytic medium | | | |
| Dulbecco's Modified Eagle Medium/Nutrient Mixture F-12 | 1X | Invitrogen | 11330-032 |
| N-2-hydroxyethylpiperazine-N-2-ethane sulfonic acid | 1X | Invitrogen | 15630-080 |
| N1 Supplement | 1X | Sigma | N6530 |
| Non-Essential Amino Acid | 1X | Invitrogen | 11140-050 |
| D-glucose | 46.4 mM | Sigma | G8769 |
| Sodium Pyruvate | 1.5 mM | Invitrogen | 11360-070 |
| L-Glutamine | 6.35 mM | Invitrogen | 25030-081 |
| Penicillin-Streptomycin | 40 U/ml | Invitrogen | 15140-122 |
| Selenite | 0.065 μg/ml | Sigma | S9133 |
| Progesterone | 0.057 μg/ml | Sigma | P6149 |

FACS/MACS sorting. Cells were incubated with Accutase for 5 minutes at 37° C. to obtain a single cell suspension, and then spun down at 200RCF for 10 minutes. These GPCs were re-suspended in cold Miltenyi Wash buffer with primary antibody (phycoerythrin (PE)-conjugated mouse anti-CD140a, 1:50, for FACS; mouse anti-CD140a, 1:100, for MACS), and incubated on ice for 30 min, gently swirling every 10 minutes. After primary antibody incubation, these cells were then washed and either incubated with a secondary antibody (rabbit anti-mouse IgG2a+b micro-beads, 1:100) followed by sorting on a magnetic stand column for MACS, or directly sorted by FACS on a FACSAria IIIu (Becton-Dickinson). The sorted cells were counted and plated onto poly-ornithine- and laminin-coated 24-well plate for further experiments. The primary and secondary antibodies are listed in Table 4.

TABLE 4

| Antibodies used for FACS/MACS sorting | | | |
|---|---|---|---|
| Antigen | Name | Dilution | Company |
| SSEA4 | Mouse anti-SSEA4 FITC Conjugate | 1:20 | Life Technologies |
| CD133 | Mouse anti-CD133 APC Conjugate | 1:50 | Miltenyi Biotech |
| CD140a | Mouse anti-CD140a PE Conjugate | 1:50 | BD |
| CD44 | Mouse anti-CD44 Microbeads | 1:50 | Miltenyi Biotech |
| CD140a | Mouse anti-CD140a | 1:100 | BD |
| Secondary Abs | Rabbit anti-Mouse IgG2a + b microbeads | 1:100 | Miltenyi Biotech |

RT-PCR Total RNA was extracted from cell lines with miRNeasy mini kit (Qiagen, 217004), and then was reversely transcribed into cDNA with Taqman Reverse Transcription kit (N808-0234). The relative expression of mRNA was measured by the Bio-RAD S6048, which was further normalized to the expression of 18S mRNA. The primer sequences are listed in Table 5.

TABLE 5

RT-PCR Primers

| Target | Forward primer | Reverse primer |
|---|---|---|
| 18S | CTGGATACCGCAGCT AGGAA (SEQ ID NO: 9) | CCCTCTTAATCATGG CCTCA (SEQ ID NO: 10) |
| GFAP | TGCGGCCGATTGTGA AC (SEQ ID NO: 11) | CCTCTTTTCTCTGCG GAACGT (SEQ ID NO: 12) |
| KCNJ9 | GTTATCCTCGAGGGC ATGGT (SEQ ID NO: 13) | CGTCCTCCAGAGTCA GCACT (SEQ ID NO: 14) |

TABLE 5-continued

RT-PCR Primers

| Target | Forward primer | Reverse primer |
|---|---|---|
| SLC12A6 | AACTGTTAGACGACG GACATAG (SEQ ID NO: 15) | CTTCGGTCTGGTGTC CATTT (SEQ ID NO: 16) |
| ATP1A2 | TGAACCATCCAACGA CAATCTA (SEQ ID NO: 17) | CTTGCTGAGGTACCA TGTTCT (SEQ ID NO: 18) |
| REST | ATGCGTACTCATTCA GGTGAGA (SEQ ID NO: 19) | TGTGAACCTGTCTTG CATGG (SEQ ID NO: 20) |

In vitro immunocytochemistry Cells were first fixed with 4% paraformaldehyde for 5 minutes at room temperature. After washing with PBS with thimerosal for 3 times, cells were penetrated with 0.1% saponin plus 1% of either goat or donkey serum for 15 minutes at room temperature. Cells were further blocked with 5% of either goat or donkey serum plus 0.05% saponin for 15 minutes at RT. After incubation with primary antibodies at 4° C. overnight, these cells were incubated with secondary antibodies for 30 minutes at RT. The primary and secondary antibodies are listed in Table 6.

TABLE 6

Antibodies used for immunocytochemistry

| Antigen | Name | Dilution | Company |
|---|---|---|---|
| Nanog | Rabbit anti-Nanog | 1:200 | Millipore |
| TRA1-60 | Mouse anti-TRA1-60 | 1:200 | Millipore |
| PAX6 | Rabbit anti-PAX6 | 1:400 | Covance |
| SOX1 | Goat anti-SOX1 | 1:200 | R&D |
| hGFAP | Mouse anti-human (specific) GFAP | 1:500 | Covance |
| PDGFRa | Rabbit anti-PDGFRa, clone D13C6 | 1:300 | Cell Signaling |
| Secondary | AlexaFluor 594 Donkey anti-Mouse IgG (H + L) | 1:400 | Invitrogen |
| antibodies | AlexaFluor 488 Donkey anti-Mouse IgG (H + L) | 1:400 | Invitrogen |
| | AlexaFluor 594 Donkey anti-Rabbit IgG (H + L) | 1:400 | Invitrogen |
| | AlexaFluor 488 Donkey anti-Rabbit IgG (H + L) | 1:400 | Invitrogen |
| | AlexaFluor 594 Donkey anti-Goat IgG (H + L) | 1:400 | Invitrogen |

Molecular cloning shRNAs of human REST (target sequences: GCAGTGGCAACATTGGAATGG (SEQ ID NO: 4) or CGGCTACAATACTAATCGA (SEQ ID NO: 6)) were cloned into the vector pTANK-EF1a-CoGFP-Puro-WPRE immediately downstream puromycin. The human cDNA of REST (a gift from Stephen Elledge, Addgene plasmid 41903) (Westbrook et al., "SCFbeta-TRCP Controls Oncogenic Transformation and Neural Differentiation Through REST Degradation," *Nature* 452:370-374 (2008), which is hereby incorporated by reference in its entirety) was cloned immediately after EF1a promoter in the vector pTANK-EF1a-IRES-mCherry-WPRE (Benraiss et al., "Human Glia Can Both Induce and Rescue Aspects of Disease Phenotype in Huntington Disease," *Nat. Commun.* 7:11758 (2016), which is hereby incorporated by reference in its entirety). The lentiviral vector allowed for expression of REST in tandem with the reporter mCherry.

The final constructs were validated for the correct insertion by sequencing. The plasmids were co-transfected with pLP-VSV (Invitrogen, K497500) and psPAX2 (a gift from Didier Trono, Addgene plasmid 12260) into 293 FT cells (Fisher Scientific, R70007) through X-tremeGENE (Roche, 06366236001) for lentiviral generation. The supernatant of 293T cells were collected and spun down at 76000RCF for 3 hours to concentrate virus (Beckman, L8-70, Ultracentrifuge). A 10-fold serial dilution of virus was prepared and transduced to 293T cells, and fluorescent colonies were counted for determination of viral titration. MACS sorted CD44+ cells were transduced with Lenti-REST or control virus, each at 1 MOI (multiplicities of infection) for 4 hours.

Potassium uptake Astrocytes were plated onto poly-ornithine- and laminin-coated 24-well plates with 30,000 cells/well. For the potassium uptake assay, astrocytes were incubated with $^{86}$Rb (1.0-3.3 uCi/well) for 15 min, and then they were washed three time with ice-cold artificial cerebrospinal fluid (aCSF, 500 μL/well). For cell lysis, 0.5N NaOH (200 μL/well) was put into each well, which was put into 5 ml cocktail liquid (Ultima Gold, Fisher Scientific, 509050575) and measured by scintillation counter (Beckman Coulter, LS6500), and the results were normalized to both total protein (BCA Protein Assay Kit, Fisher Scientific, 23227) and cell number (Hemocytometer, Fisher Scientific, 02-671-54). The aCSF solution contained (in mM) 124 NaCl, 2.5 KCl, 1.75 NaH2PO4, 2 MgCl2, 2 CaCl2, 0.04 Vit.C, 10 glucose and 26 $NaHCO_3$, pH 7.4.

Example 1—Astrocytic Differentiation was Impaired in SCZ GPCs iPSCs were produced from skin samples obtained from patients with childhood-onset schizophrenia, as well as healthy young adult controls free of known mental illness, as previously described (Windrem et al., "Human iPSC Glial Mouse Chimeras Reveal Glial Contributions to Schizophrenia," *Cell Stem Cell* 21:195-208.e6 (2017), which is hereby incorporated by reference in its entirety). Patient identifiers were not available to investigators besides the treating psychiatrist, although age, gender, race, diagnosis and medication history accompanied cell line identifiers. Briefly, fibroblasts were isolated from each sample. From these, 8 hiPSC lines were derived from patient samples and normal controls (5 juvenile-onset schizophrenia patients and 3 healthy gender-matched and age-analogous controls (Table 1). iPSCs were generated using excisable floxed polycistronic hSTEMCCA lentivirus (Somers et al., "Generation of Transgene-Free Lung Disease-Specific Human Induced Pluripotent Stem Cells Using a Single Excisable Lentiviral Stem Cell Cassette," *Stem Cells* 28:1728-1740 (2010); Zou et al., "Establishment of Transgene-Free Induced Pluripotent Stem Cells Reprogrammed From Human Stem Cells of Apical Papilla for Neural Differentiation," *Stem Cell Res. Ther.* 3:43 (2012), which are hereby incorporated by reference in their entirety) encoding Oct4, Sox2, Klf4 and c-Myc (Takahashi et al., "Induction of Pluripotent Stem Cells From Adult Human Fibroblasts by Defined Factors," *Cell* 131:861-872 (2007); Welstead et al., "Generating iPS Cells From MEFS Through Forced Expression of Sox-2, Oct-4, c-Myc, and Klf4," *J. Vis. Exp.* (14): 734 (2008), which are hereby incorporated by reference in their entirety). All lines were validated as pluripotent using RNA sequencing and immunolabeling to assess pluripotent gene expression. The identity of each iPSC line was confirmed to match the parental donor fibroblasts using short tandem repeat (STR)-based DNA fingerprinting, and each line was karyotyped to confirm genomic integrity. A fourth hiPSC control line, C27 (Chambers et al., "Highly Efficient Neural Conversion of Human ES and iPS Cells by Dual Inhibition of SMAD Signaling," *Nature Biotechnology* 27:275-280 (2009), which is hereby incorporated by reference in its entirety), was also used, to ensure that all genomic and phenotypic data were consistent with prior work (Wang et al., "Human iPSC-Derived Oligodendrocyte Progenitor Cells Can Myelinate and Rescue a Mouse Model of Congenital Hypomyelination," *Cell Stem Cell* 12:252-264 (2013), which is hereby incorporated by reference in its entirety).

Glial differentiation efficiency of cells derived from SCZ patients and control subjects (n=4 lines from 4 different patients, each with ≥3 repeats/patient, each versus paired control) was compared by instructing these iPSC cells to GPC fate as previously described (Wang et al., "Human iPSC-Derived Oligodendrocyte Progenitor Cells Can Myelinate and Rescue a Mouse Model of Congenital Hypomyelination," *Cell Stem Cell* 12:252-264 (2013), which is hereby incorporated by reference in its entirety), and assessing their expression of stage-specific markers of maturation as a function of time. All tested iPSCs were found to exhibit typical colonies, and express markers of pluripotency by flow cytometry, including SSEA4 (FIG. 1A). At the neural progenitor cell (NPC) stage, both ICC and flow cytometry revealed that the expression levels of the stage-selective markers, paired box protein pax-6 (PAX6), sex determining region Y-box 1 (SOX1), and the cell surface marker prominin-1/CD133, were no different between CTR- and SCZ-derived lines (FIG. 1B and FIG. 2A). At the GPC stage, the cells were similarly assessed for expression of the GPC-selective platelet-derived growth factor receptor alpha (PDGFRα/CD140a) (Sim et al., "CD140a Identifies a Population of Highly Myelinogenic, Migration-Competent and Efficiently Engrafting Human Oligodendrocyte Progenitor Cells," *Nature Biotechnology* 29:934-941 (2011), which is hereby incorporated by reference in its entirety), which revealed that the efficiencies of GPC generation did not differ significantly between SCZ- and CTR-derived NPCs (FIG. 1C and FIG. 2B). Thus, no differences in the differentiation of SCZ and CTR iPSCs were noted through the GPC stage.

At that point, these SCZ- and CTR-derived GPCs were further differentiated into astrocytes after incubating in M41 medium with 20 ng/ml BMP4 for 3 weeks. Immunolabeling revealed that the proportion of GFAPT astrocytes was significantly higher in control lines (4 CTR lines, n≥3/each line, means of 4 CTR lines/70.1%±2.4%) than in SCZ lines (4 SCZ lines, n≥3/each line, means of 4 SCZ lines/39.9% ±2.0%; $P<0.001$ by two tailed t-test) (FIG. 2C). This defect of astrocytic differentiation was consistently observed in all SCZ GPCs, relative to CTR GPCs, and comprised an in vitro correlate to previously described astroglial differentiation defects in vivo (Windrem et al., "Human iPSC Glial Mouse Chimeras Reveal Glial Contributions to Schizophrenia," *Cell Stem Cell* 21:195-208.e6 (2017), which is hereby incorporated by reference in its entirety).

Example 2—SCZ Astrocytes Exhibit Reduced Potassium Uptake

To identify the molecular concomitants to the defective astrocytic differentiation of SCZ GPCs, RNA-seq on FACS-sorted CD140a+ GPCs from 3 different CTR- and 4 SCZ-derived lines at time points ranging from 154 to 242 days in vitro had been performed (Windrem et al., "Human iPSC Glial Mouse Chimeras Reveal Glial Contributions to Schizophrenia," *Cell Stem Cell* 21:195-208.e6 (2017), which is hereby incorporated by reference in its entirety). mRNA was isolated from these cells with polyA-selection for RNA sequencing on an Illumina HiSeq 2500 platform for approximately 45 million 1×100 bp reads per sample. The original counts were analyzed to determine disease-dysregulated genes at 5% FDR and log 2 fold change >1. By that means, 118 mRNAs that were consistently and significantly differentially expressed by CD140a sorted SCZ hGPCs relative to their control iPSC hGPCs had been identified (Windrem et al., "Human iPSC Glial Mouse Chimeras Reveal Glial Contributions to Schizophrenia," *Cell Stem Cell* 21:195-208.e6 (2017), which is hereby incorporated by reference in its entirety). Among these, a number of genes involved in glial lineage progression were downregulated in SCZ hGPCs, relative to their normal controls, suggesting that astroglial differentiation was impaired in SCZ in a cell autonomous fashion, due to intrinsic defects in SCZ-derived glial progenitor cells.

Together with the impaired astrocytic differentiation of SCZ GPCs, the RNA-seq data suggested that those astrocytes that do successfully differentiate might nonetheless be functionally impaired. In particular, the RNA-seq revealed the downregulated transcription in SCZ GPCs of a broad set of potassium channel (KCN)-encoding genes, including the $Na^+$—$K^+$ ATPase, $Na^+$—$K^+$/2Cl cotransporter (NKCC), and Kir-family inwardly rectifying potassium channels (FIG. 3A) (Windrem et al., "Human iPSC Glial Mouse Chimeras Reveal Glial Contributions to Schizophrenia," *Cell Stem Cell* 21:195-208.e6 (2017), which is hereby incorporated by reference in its entirety), all of which play important roles in potassium uptake by astrocytes (Larsen et al., "Contributions of the Na(+)/K(+)-ATPase, NKCC1, and Kir4.1 to Hippocampal K(+) Clearance and Volume Responses," *Glia* 62:608-622 (2014); Macaulay & Zeuthen, "Glial K(+) Clearance and Cell Swelling: Key Roles for Cotransporters and Pumps," *Neurochem. Res.* 37:2299-2309 (2012), which are hereby incorporated by reference in their entirety) (FIG. 4A). Among these dysregulated KCN genes, ATP1A2, SLC12A6, and KCNJ9, which respectively encode the Na/$K^+$-ATPase, $Na^+$/$K^+$/$2Cl^-$ cotransporter, and the Kir3.3 voltage gated $K^+$ channel (Bottger et al., "Glutamate-System Defects Behind Psychiatric Manifestations in a Familial Hemiplegic Migraine Type 2 Disease-Mutation Mouse Model," *Sci. Rep.* 6:22047 (2016); Gamba & Friedman, "Thick Ascending Limb: The Na(+):K(+):2Cl(−) Cotransporter, NKCC2, and the Calcium-Sensing Receptor, CaSR," *Pflugers Arch.* 458:61-76 (2009); Lesage et al., "*Molecular Properties of Neuronal G-Protein-Activated Inwardly* Rectifying $K^+$ Channels," *J. Biol. Chem.* 270:28660-28667 (1995), which are hereby incorporated by reference in their entirety), were consistently and substantially down-regulated in all 4 SCZ lines assessed, compared to the 4 control lines. These findings suggested a broad-based impairment of $K^+$ uptake by SCZ glia.

On the basis of these genomic data, whether $K^+$ uptake was actually impaired in SCZ astrocytes was assessed. To address this hypothesis, qPCR was used to confirm whether these $K^+$ channel-associated genes were dysregulated in SCZ glia. They were indeed significantly down regulated, thus validating the RNA-seq analysis (FIG. 3B and FIG. 4B). Next, functional $K^+$ uptake was assessed directly, in cultured SCZ- and CTR-derived astrocytes. To obtain mature SCZ and CTR astrocyte cultures, CD44-sorted astrocyte-biased progenitors were cultured in base media supplemented with 10% fetal bovine serum (FBS) and 20 ng/ml BMP4 for 3 weeks, so as to potentiate the differentiation of mature, glial fibrillary acidic protein (GFAP)-expressing, fiber-bearing astrocytes (FIGS. 5A-5C). Under these highly astrogliogenic culture conditions, and using cells already sorted for the early astrocytic marker CD44, astrocytic maturation was achieved by both SCZ—as well as CTR derived astroglial progenitor cells (FIGS. 5A-5C). Astrocytes from 4 different SCZ and 4 different CTR lines were then incubated with $^{86}Rb$, a surrogate monovalent cation for $K^+$ uptake (Larsen et al., "Contributions of the Na(+)/K(+)-ATPase, NKCC1, and Kir4.1 to Hippocampal K(+) Clearance and Volume Responses," *Glia* 62:608-622 (2014), which is hereby incorporated by reference in its entirety), and rubidium uptake measured as a function of both cell number and total protein. The $K^+$ uptake in SCZ glia (4 SCZ cell lines, 5 repeats/each line) was sharply decreased relative to CTR glia (4 CTR cell lines, 5 repeats/each line), normalized by both cell number and total protein (FIG. 4C; $P<0.001$ by two tailed t-test).

Figure 4D:
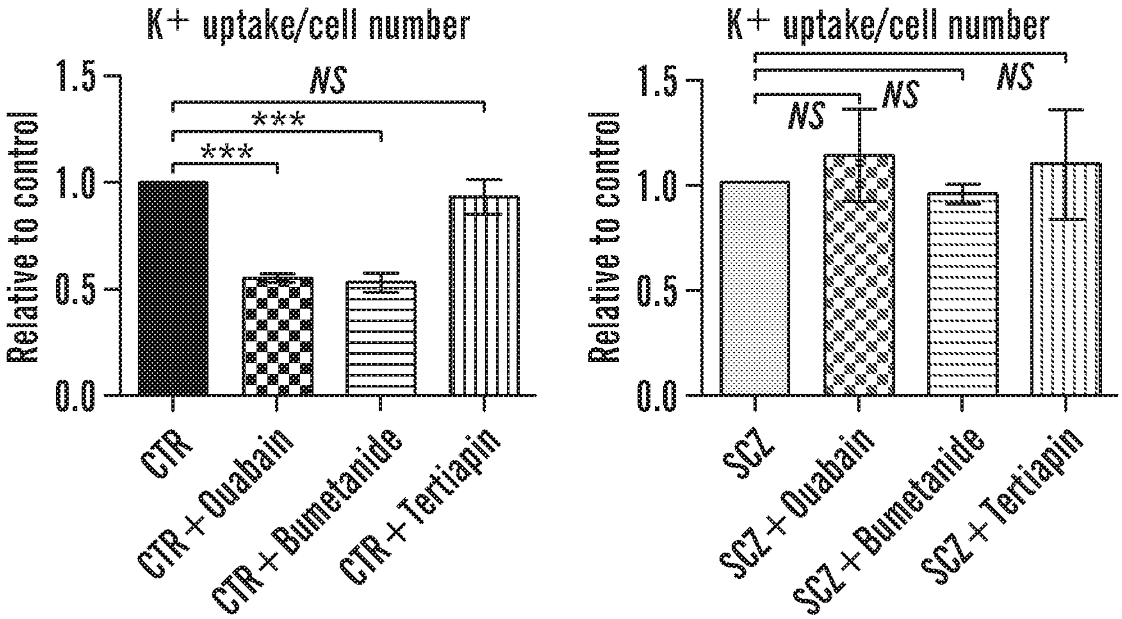
Figure 4E:
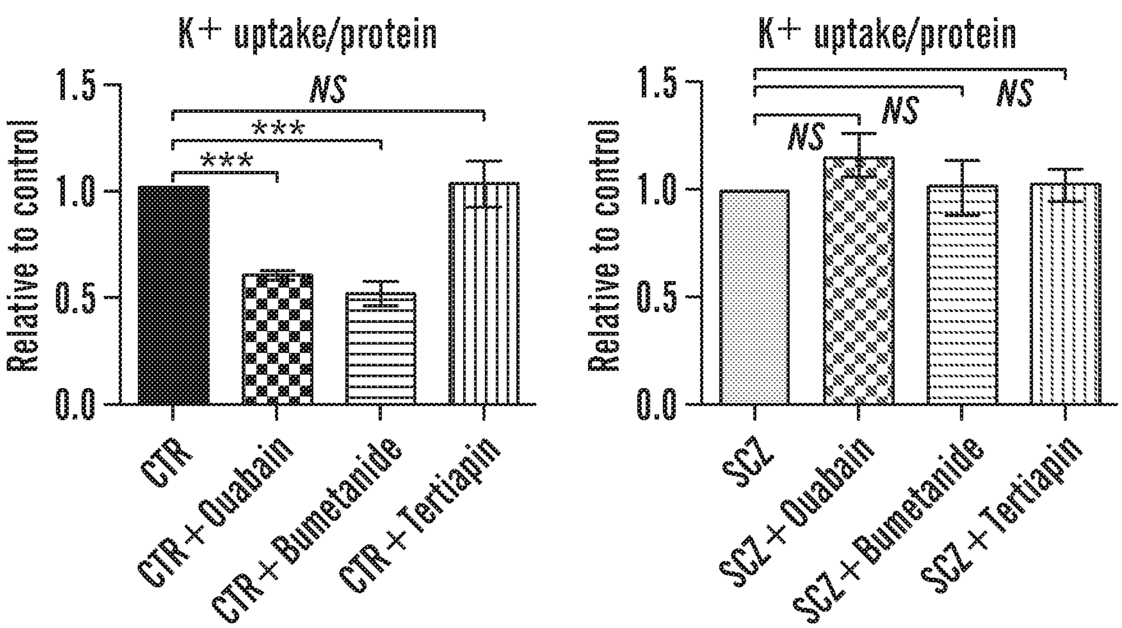

Since several genes involved in $Na^+$/$K^+$-ATPase, $Na^+$/$K^+$/$2Cl^-$ cotransporter, and inwardly rectifying $K^+$ channels were dysregulated in SCZ glia, the drugs ouabain, bumetanide, and tertiapin were used to respectively block these three potassium uptake mechanisms. The actions of these drugs on astrocytes had not been previously assessed, so different concentrations of each were first tested to determine optimal dose ranges for modulating astroglial $K^+$ uptake. Ouabain and bumetanide, respectively, targeting the $Na^+$/$K^+$-ATPase and $Na^+$/$K^+$/$2Cl^-$ cotransporters, significantly inhibited $K^+$ uptake in CTR glia, while tertiapin, which targets Kir channels, did not (FIGS. 4D-4E, left graphs). In marked contrast, neither ouabain nor bumetanide affected $K^+$ uptake by SCZ astrocytes (FIGS. 4D-4E, right graphs). This suggests that the functional decrement in $K^+$ uptake by SCZ-derived astrocytes may be primarily due to down-regulated $Na^+$/$K^+$-ATPase and Na/$K^+$/$2Cl^-$ cotransporter function, rendering these cells refractory to ouabain and bumetanide treatment.

Example 3—REST Regulates Potassium Uptake by SCZ Astrocytes

Since a large number of potassium channel-encoding genes are dysregulated in SCZ glia, it is difficult to modulate glial $K^+$ uptake through genetic means targeting individual potassium channels alone. To address this issue, Biobase-Transfac analysis was used. This analysis was developed to identify regulatory regions common to different genes, as a means of defining their shared upstream regulators (Hu et al., "Genome-Wide Identification of Transcription Factors and Transcription-Factor Binding Sites in Oleaginous Microalgae *Nannochloropsis*," *Sci. Rep.* 4:5454 (2014), which is hereby incorporated by reference in its entirety). By this means, shared regulatory elements within 1 kb of the transcription start sites (TSS) of the SCZ-associated glial genes were identified in the data sets. The intent was to identify upstream transcription factors able to modulate these genes as a group. Using a 13 nucleotide consensus sequence (CCNNGGTGCTGAA; SEQ ID NO: 21), it was determined that the majority of all down-regulated potassium channel genes were targets of the neuron restrictive silencing factor (NRSF) REST (FIG. 3C), a potent transcriptional repressor that can act in non-neural cells to repress neural gene expression (Hirabayashi & Gotoh, "Epigenetic Control of Neural Precursor Cell Fate During Development," *Nat. Rev. Neurosci.* 11:377-388 (2010), which is hereby incorporated by reference in its entirety). On that basis, the RNAseq data was queried, which revealed that REST was indeed consistently and significantly upregulated in SCZ GPCs relative to CTR GPCs (Windrem et al., "Human iPSC Glial Mouse Chimeras Reveal Glial Contributions to Schizophrenia," *Cell Stem Cell* 21:195-208.e6 (2017), which is hereby incorporated by reference in its entirety). qPCR was used to confirm that the upregulation of REST expression by SCZ glia was consistent across all of the patients in the series (FIG. 6A). On that basis, it was postulated that the upregulation of REST in schizophrenia-derived glia, and their attendant epigenetic modification, might be sufficient to repress potassium channel associated gene expression.

To test this postulate, lentivirus was used to overexpress REST in CTR glial cells, and $K^+$ uptake by the transduced cells was assessed. In parallel, REST expression in SCZ glial cells was knocked down through lentiviral shRNAi transduction, and similarly $K^+$ uptake in these cells was assessed. qPCR validation confirmed that REST was significantly modulated as intended in both CTR and SCZ glial cells, respectively (FIG. 7). By this means, it was found that the expression of several $K^+$ channel-associated genes, including SLC12A6, KCNJ9, and ATP1A2, was significantly repressed in CTR glial cells subjected to REST overexpression (FIG. 6B). In contrast, the expression of these potassium channel genes was strongly upregulated in SCZ lines subjected to REST knockdown (FIG. 6B).

Figure 6C:
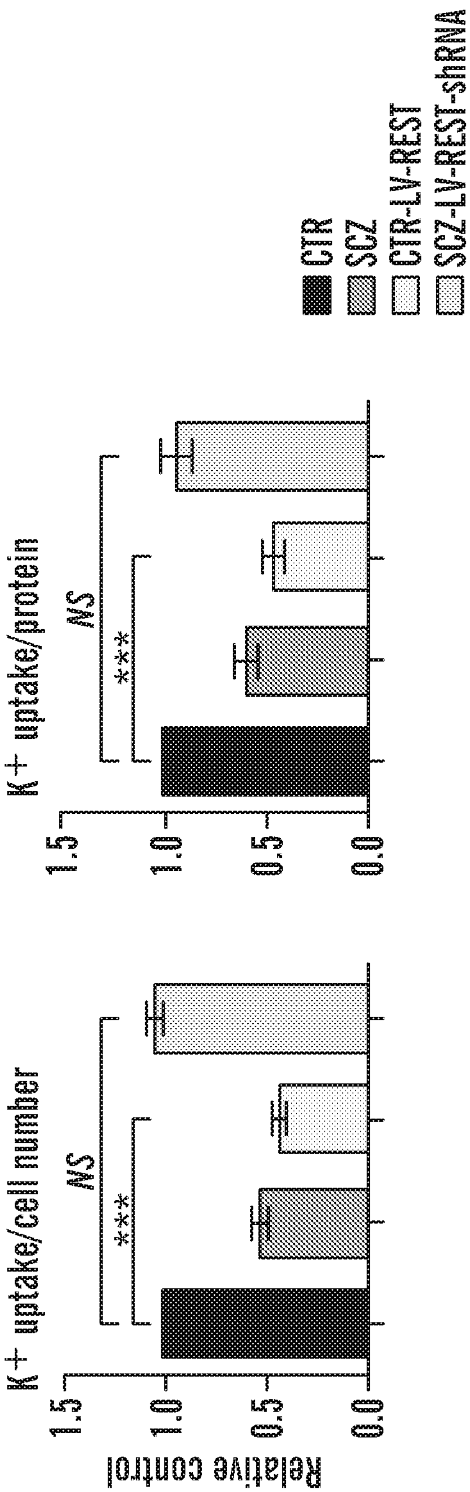
Figure 6D:
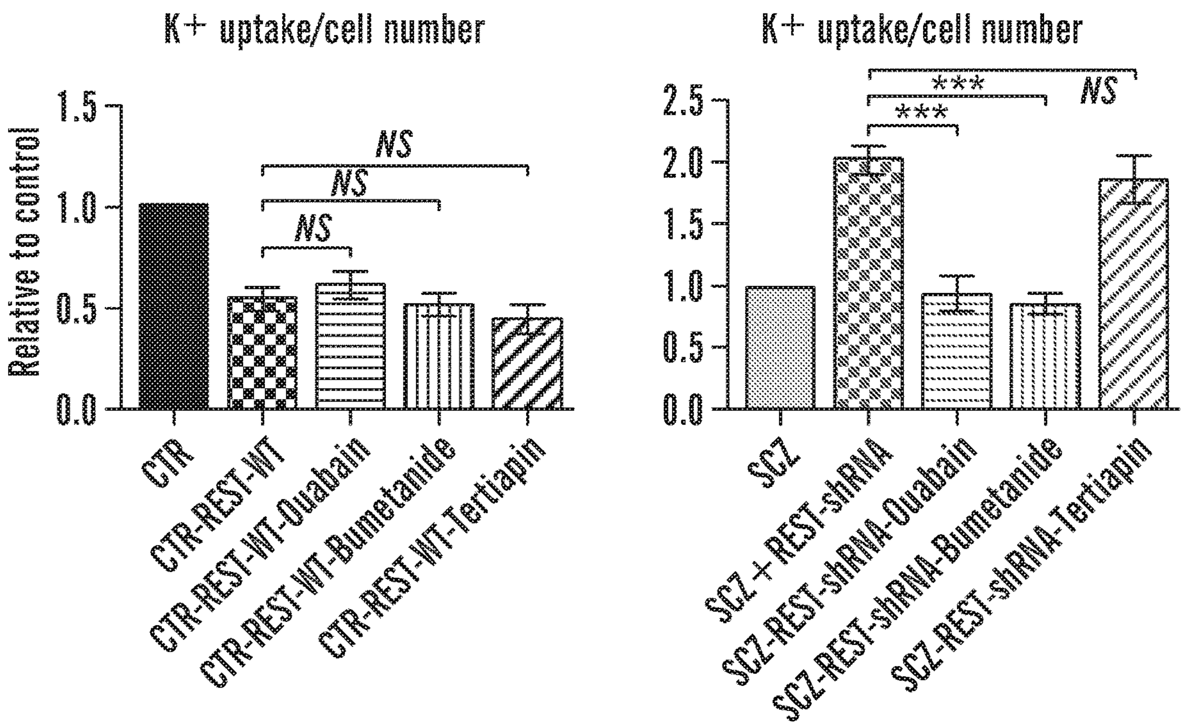
Figure 6E:
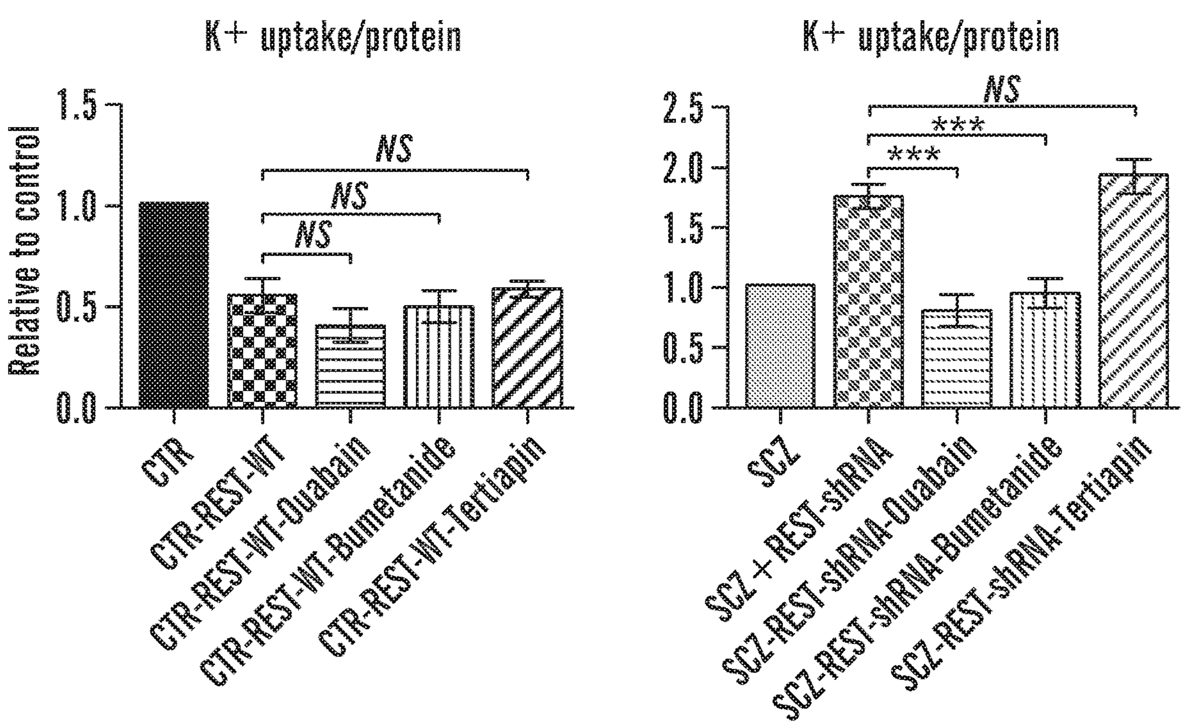

Importantly, REST-overexpressing CTR astrocytes mimicked the functional potassium dysregulation of SCZ glia, in that their $K^+$ uptake was significantly reduced compared to that of non-transduced CTR glia (FIG. 6C). Neither ouabain nor bumetanide further decreased $K^+$ uptake by these cells, suggesting that their targeted channels were down-regulated to the point of functional irrelevance (FIGS. 6D-6E). Conversely, $K^+$ uptake by SCZ astrocytes subjected to REST knockdown was strongly enhanced, to levels no different from those of CTR astrocytes (FIG. 6C). Both ouabain and bumetanide were then able to significantly reduce $K^+$ uptake by these REST shRNAi-transduced SCZ astrocytes (FIGS. 6D-6E). Together, these data suggest that REST knockdown in SCZ glia promoted the restoration of normal $K^+$ uptake by these cells, by rescuing their transcription of both the $Na/K^+$-ATPase and the $Na^+/K^+$ $2Cl^-$ cotransporter, and thereby restoring a salient feature of astroglial potassium homeostasis.

The data herein indicate that astrocytic differentiation is impaired in GPCs derived from childhood onset schizophrenics, and that this maturational defect may be rescued by the de-repression of glial differentiation-associated transcription via REST knock-down. Importantly, astrocytic depletion has been recently noted in both cortical and subcortical regions of patients with schizophrenia, and this might be especially prominent in the white matter, (Rajkowska et al., "Layer-Specific Reductions in GFAP-Reactive Astroglia in the Dorsolateral Prefrontal Cortex in Schizophrenia," *Schizophr. Res.* 57:127-138 (2002); Steffek et al., "Cortical Expression of Glial Fibrillary Acidic Protein and Glutamine Synthetase is Decreased in Schizophrenia," *Schizophr. Res.* 103:71-82 (2008); Williams et al., "Astrocyte Decrease in the Subgenual Cingulate and Callosal Genu in Schizophrenia," *Eur. Arch. Psychiatry Clin. Neurosci.* 263:41-52 (2013), which are hereby incorporated by reference in their entirety). Astrocytes play key contributions to neural circuit formation and stability (Christopherson et al., "Thrombospondins are Astrocyte-Secreted Proteins That Promote CNS Synaptogenesis," Cell 120:421-433 (2005); Clarke & Barres, "Emerging Roles of Astrocytes in Neural Circuit Development," *Nature Reviews Neuroscience* 14:311-321 (2013), which are hereby incorporated by reference in their entirety). Thus, any such developmental defect of astrocytic differentiation in SCZ GPCs might lead to profound defects in the initial formation or stability of neural circuits, a defect that is one of the hallmarks of schizophrenia (Penzes et al., "Dendritic Spine Pathology in Neuropsychiatric Disorders," *Nat. Neurosci.* 14:285-293 (2011), which is hereby incorporated by reference in its entirety).

Glial maturation is precisely regulated in human brain development (Goldman & Kuypers, "How to Make an Oligodendrocyte," Development 142:3983-3995 (2015); Molofsky et al., "Astrocytes and Disease: A Neurodevelopmental Perspective," *Genes & Development* 26:891-907 (2012), which are hereby incorporated by reference in their entirety). Astrocytes have a multitude of roles in the CNS, including energy support to both neurons and oligodendrocytes, potassium buffering, neurotransmitter recycling, and synapse formation and maturation (Blanco-Suarez et al., "Role of Astrocyte-Synapse Interactions in CNS Disorders," *J. Physiol.* 595:1903-1916 (2017); Clarke & Barres, "Emerging Roles of Astrocytes in Neural Circuit Development," *Nature Reviews Neuroscience* 14:311-321 (2013); Verkhratsky et al., "Why are Astrocytes Important?" *Neurochemical Research* 40:389-401 (2015), which are hereby incorporated by reference in their entirety). As such, astrocytes play critical roles in neural circuit formation and maintenance. Astrocytes also contribute to the glymphatic system through the regulation of cerebral spinal fluid flow (Xie et al., "Sleep Drives Metabolite Clearance From the Adult Brain," *Science* 342:373-377 (2013), which is hereby incorporated by reference in its entirety). Thus, the delayed differentiation of SCZ astrocytes may have significant effects on neural network formation, organization and mature function alike.

A number potassium channels were down-regulated in SCZ glia. Interestingly, prior genome wide association studies have identified an association of potassium channel genes with schizophrenia. For instance, the chromosome 1q21-q22 locus, containing KCNN3, has a significant linkage to familial schizophrenia (Brzustowicz et al., "Location of a Major Susceptibility Locus for Familial Schizophrenia on Chromosome 1q21-q22," *Science* 288:678-682 (2000), which is hereby incorporated by reference in its entirety). KCNN3 is widely express in the human brain, and selectively regulates neuronal excitability and neurotransmitter release in monoaminergic neurons (O'Donovan & Owen, "Candidate-Gene Association Studies of Schizophrenia," *Am. J. Hum. Genet.* 65:587-592 (1999), which is hereby incorporated by reference in its entirety). In addition to KCNN3, a number of other potassium channel genes have been associated with schizophrenia, including KCNQ2 and KCNAB1 (Lee et al., "Pathway Analysis of a Genome-Wide Association Study in Schizophrenia," *Gene* 525:107-115 (2013), which is hereby incorporated by reference in its entirety). More recently, a novel de novo mutation in ATP1A3, a subunit of the sodium-potassium pump, has been specifically associated with childhood-onset schizophrenia (Smedemark-Margulies et al., "*A Novel De Novo Mutation in ATP1A3 and Childhood-Onset Schizophrenia," Cold Spring Harb. Mol. Case Stud* 2: a001008 (2016), which is hereby incorporated by reference in its entirety).

The down-regulation or dysfunction of these potassium channel genes in GPCs and their derived astrocytes may contribute significantly to disease phenotype in schizophrenia. Potassium channel genes are widely expressed in both GPCs (Coppi et al., "UDP-Glucose Enhances Outward K(+) Currents Necessary for Cell Differentiation and Stimulates Cell Migration by Activating the GPR17 Receptor in Oligodendrocyte Precursors," *Glia* 61:1155-1171 (2013); Maldonado et al., "Oligodendrocyte Precursor Cells are Accurate Sensors of Local $K^+$ in Mature Gray Matter," *J. Neurosci.* 33:2432-2442 (2013), which are hereby incorporated by reference in their entirety) and astrocytes (Larsen et al., "Contributions of the Na(+)/K(+)-ATPase, NKCC1, and Kir4.1 to Hippocampal K(+) Clearance and Volume Responses," *Glia* 62:608-622 (2014); Zhang & Barres, "Astrocyte Heterogeneity: An Underappreciated Topic in Neurobiology," *Current Opinion in Neurobiology* 20:588-594 (2010), which are hereby incorporated by reference in their entirety), in which they regulate not only proliferation, migration, and differentiation, but also the relationship of glia to neurons (Coppi et al., "UDP-Glucose Enhances Outward K(+) Currents Necessary for Cell Differentiation and Stimulates Cell Migration by Activating the GPR17 Receptor in Oligodendrocyte Precursors," *Glia* 61:1155-1171 (2013); Maldonado et al., "Oligodendrocyte Precursor Cells are Accurate Sensors of Local $K^+$ in Mature Gray Matter," *J. Neurosci.* 33:2432-2442 (2013), which are hereby incorporated by reference in their entirety). In regards to the latter, astrocytes also regulate synaptic $K^+$ uptake through $Na^+/K^+$-ATPase, NKCC, and the inwardly rectifying Kir channels (Larsen et al., "Contributions of the Na(+)/K(+)-ATPase, NKCC1, and Kir4.1 to Hippocampal K(+) Clearance and Volume Responses," *Glia* 62:608-622 (2014); Zhang & Barres, "Astrocyte Heterogeneity: An Underappreciated Topic in Neurobiology," *Current Opinion in Neurobiology* 20:588-594 (2010), which are hereby incorporated by reference in their entirety), thereby establishing neuronal firing thresholds over broad regional domains. In addition, dysregulated potassium channel genes have been associated with a broad variety of neurological and psychiatric diseases. Several Kir genes, including Kir4.1, are involved in astrocytic potassium buffering and glutamate uptake, and deletion of these genes has been noted in both Huntington's disease and multiple sclerosis (Seifert et al., "Astrocyte Dysfunction in Neurological Disorders: A Molecular Perspective," *Nat. Rev. Neurosci.* 7:194-206 (2006); Tong et al., "Astrocyte Kir4.1 Ion Channel Deficits Contribute to Neuronal Dysfunction in Huntington's Disease Model Mice," *Nat. Neurosci.* 17:694-703 (2014), which are hereby incorporated by reference in their entirety). In addition, mutation of astrocytic ATP1A2, the $\alpha2$ isoform of the sodium-potassium pump, may be causally associated with familial hemiplegic migraine (Bottger et al., "Glutamate-System Defects Behind Psychiatric Manifestations in a Familial Hemiplegic Migraine Type 2 Disease-Mutation Mouse Model," *Sci. Rep.* 6:22047 (2016); Swarts et al., "Familial Hemiplegic Migraine Mutations Affect Na,K-ATPase Domain Interactions," *Biochim. Biophys. Acta* 1832:2173-2179 (2013), which are hereby incorporated by reference in their entirety). In all of these examples, glial $K^+$ uptake is impaired, just as in SCZ glia, and all are associated with elements of phenotypic hyperexcitability. Indeed, elevated extracellular $K^+$ has been shown to alter the neuronal excitability and neural circuit stability in a mouse model of schizophrenia (Crabtree et al., "Alteration of Neuronal Excitability and Short-Term Synaptic Plasticity in the Prefrontal Cortex of a Mouse Model of Mental Illness," *J. Neurosci.* 37 (15): 4158-4180 (2017), which is hereby incorporated by reference in its entirety). Thus, the decreased $K^+$ uptake of SCZ glia may be a significant contributor to schizophrenia pathogenesis, especially in regards to those schizophrenic phenotypes associated with hyperexcitability and seizure disorders, which would be potentiated in the setting of disrupted potassium homeostasis.

The upregulated REST in SCZ glia appears to be both necessary and sufficient for the suppression of both potassium channel gene expression and potassium uptake. REST, as a transcriptional repressor, regulates neural gene expression in both neurons and glia (Bruce et al., "Genome-Wide Analysis of Repressor Element 1 Silencing Transcription Factor/Neuron-Restrictive Silencing Factor (REST/NRSF) Target Genes," *Proc. Nat'l. Acad. Sci. U.S.A.* 101:10458-10463 (2004); Dewald et al., "The RE1 Binding Protein REST Regulates Oligodendrocyte Differentiation," *J. Neurosci.* 31:3470-3483 (2011), which are hereby incorporated by reference in their entirety). In broad terms, REST represses neural genes through its recruitment of CoREST and mSIN3a, the complex of which further recruits HDAC1/2 and methyltransferase G9a to promote concurrent histone deacetylation and methylation, which together serve to block transcription (Hirabayashi & Gotoh, "Epigenetic Control of Neural Precursor Cell Fate During Development," *Nat. Rev. Neurosci.* 11:377-388 (2010), which is hereby incorporated by reference in its entirety). As such, the misdirected upregulation of REST inhibits potassium channel gene expression, and thereby contributes to the disease phenotype of those disorders associated with dysregulated potassium homeostasis and its attendant neuronal hyperexcitability. For instance, up-regulated REST in peripheral sensory neurons induces the downregulation of KCNQ2, which in turn potentiates the hyperexcitability of sensory neurons and hence the maintenance of neuropathic pain (Rose et al., "Transcriptional Repression of the M Channel Subunit Kv7.2 in Chronic Nerve Injury," *Pain* 152:742-754 (2011), which is hereby incorporated by reference in its entirety). REST similarly represses KCNQ3 gene expression, and the down regulation of KCNQ3 by REST provokes neuronal hyperexcitability in specific neonatal epilepsies (Mucha et al., "Transcriptional Control of KCNQ Channel Genes and the Regulation of Neuronal Excitability," *J. Neurosci.* 30:13235-13245 (2010), which is hereby incorporated by reference in its entirety).

Furthermore, REST is involved in schizophrenia through its modulation of miR137 (Warburton et al., "Characterization of a REST-Regulated Internal Promoter in the Schizophrenia Genome-Wide Associated Gene MIR137*," Schizophr. Bull.* 41:698-707 (2015), which is hereby incorporated by reference in its entirety), which regulates multiple schizophrenia-associated genes, including CACNA1C, TCF4, and ANK3 (Kwon et al., "Validation of Schizophrenia-Associated Genes CSMD1, C10orf26, CACNA1C and TCF4 as miR-137 Targets," *Mol. Psychiatry* 18:11-12 (2013), which is hereby incorporated by reference in its entirety; Schizophrenia Psychiatric Genome-Wide Association Study (GWAS) Consortium, "Genome-Wide Association Study Identifies Five New Schizophrenia Loci," *Nat. Genet.* 43:969-976 (2011), which are hereby incorporated by reference in their entirety). Other investigators have reported that REST can repress the expression of potassium channel-associated genes (Bruce et al., "Genome-Wide Analysis of Repressor Element 1 Silencing Transcription Factor/Neuron-Restrictive Silencing Factor (REST/NRSF) Target Genes," *Proc. Nat'l. Acad. Sci. U.S.A.* 101:10458-10463 (2004), which is hereby incorporated by reference in its entirety), and can suppress oligodendroglial differentiation within the glial lineage (Dewald et al., "The RE1 Binding Protein REST Regulates Oligodendrocyte Differentiation," *J. Neurosci.* 31:3470-3483 (2011), which is hereby incorporated by reference in its entirety). Thus, it was hypothesized that pathologically high levels of REST might repress $K^+$ channel associated gene expression, and thereby decrease $K^+$ uptake, in schizophrenia-derived glia. This would be expected to lead to high interstitial $K^+$, and hence to relative neuronal hyperexcitability and network desynchronization. That said, the role of REST in disordered glial potassium homeostasis has never before been reported. The data herein suggest the likelihood that some fraction of schizophrenic patients might suffer high interstitial $K^+$ levels, as a function of diminished glial potassium uptake. This would be expected to yield neuronal hyperexcitability, as has been reported Huntington disease, another disorder characterized by glial potassium channel dysfunction (Benraiss et al., "Human Glia Can Both Induce and Rescue Aspects of Disease Phenotype in Huntington Disease," *Nat. Commun.* 7:11758 (2016), which is hereby incorporated by reference in its entirety). As such, the observation of a REST-dependent impairment of $K^+$ uptake by SCZ derived glia indicates that REST is an effective target for the treatment of schizophrenia In that regard, several REST-targeted drugs have been developed for epilepsy and Huntington disease, including valproic acid and X5050 (Charbord et al., "High Throughput Screening for Inhibitors of REST in Neural Derivatives of Human Embryonic Stem Cells Reveals a Chemical Compound That Promotes Expression of Neuronal Genes," *Stem Cells* 31:1816-1828 (2013); Graff & Tsai, "The Potential of HDAC Inhibitors as Cognitive Enhancers," *Annu. Rev. Pharmacol. Toxicol.* 53:311-330 (2013), which are hereby incorporated by reference in their entirety). The data herein indicates that these agents may have therapeutic utility in schizophrenia as well. In that regard, it was noted that ouabain and bumetanide significantly inhibited $K^+$ uptake by both CTR astrocytes and SCZ astrocytes following REST knockdown, and yet neither affected the uptake of $K^+$ by astrocytes transduced to over-express REST. These data suggest that the suppression of $K^+$ uptake in SCZ glia by REST is through the suppression of potassium channel gene expression. A corollary of that observation is that modulators of $K^+$ uptake might have real value in the treatment of schizophrenia (Calcaterra et al., "Schizophrenia-Associated hERG Channel Kv11.1-3.1 Exhibits a Unique Trafficking Deficit that is Rescued Through Proteasome Inhibition for High Throughput Screening," *Sci. Rep.* 6:19976 (2016); He et al., "Current Pharmacogenomic Studies on hERG Potassium Channels," *Trends Mol. Med.* 19:227-238 (2013); Rahmanzadeh et al., "Lack of the Effect of Bumetanide, a Selective NKCC1 Inhibitor, in Patients With Schizophrenia: A Double-Blind Randomized Trial," *Psychiatry Clin. Neurosci.* 71:72-73 (2017), which are hereby incorporated by reference in their entirety). Thus, the data herein reveal the defective differentiation of astrocytes by SCZ GPCs, the REST-dependent suppression of potassium channel genes and consequent defective uptake of $K^+$ by SCZ astrocytes. The resultant deficiencies in synaptic potassium homeostasis may be expected to significantly lower neuronal firing thresholds while accentuating network desynchronization (Benraiss et al., "Human Glia Can Both Induce and Rescue Aspects of Disease Phenotype in Huntington Disease," *Nat. Commun.* 7:11758 (2016), which is hereby incorporated by reference in its entirety). As such, these findings identify a causal contribution of astrocytic pathology to the neuronal dysfunction of SCZ, and by so doing suggests a set of tractable molecular targets for its treatment Although preferred embodiments have been depicted and described in detail herein, it will be apparent to those skilled in the relevant art that various modifications, additions, substitutions, and the like can be made without departing from the spirit of the disclosure and these are therefore considered to be within the scope of the disclosure as defined in the claims which follow.

What is claimed is:

1. A method of restoring $K^+$ uptake in human glial cells having decreased $K^+$ uptake, said method comprising:

selecting a population of human glial cells having decreased $K^+$ uptake and administering, to the human glial cells having decreased $K^+$ uptake, an inhibitor of RE1-Silencing Transcription factor (REST) selective gene expression under conditions effective to restore $K^+$ uptake by said human glial cells, wherein the inhibitor comprises an inhibitory nucleic acid molecule selected from the group consisting of a REST antisense oligonucleotide, a REST shRNA, and a REST siRNA, wherein the inhibitor is packaged in a delivery vehicle that comprises a glial cell targeting moiety.

2. A method of restoring glial cell $K^+$ uptake in a human subject, said method comprising:

selecting a human subject having decreased glial cell $K^+$ uptake, and administering, to the human subject, an inhibitor of RE1-Silencing Transcription factor (REST) selective gene expression under conditions effective to restore glial cell $K^+$ uptake, wherein the inhibitor comprises an inhibitory nucleic acid molecule selected from the group consisting of a REST antisense oligonucleotide, a REST shRNA, and a REST siRNA, wherein the inhibitor is packaged in a delivery vehicle that comprises a glial cell targeting moiety.

3. The method of claim 2, wherein the glial cells are glial progenitor cells and said administering is carried out under conditions effective to restore glial progenitor cell derived astrocytic differentiation in the subject.

4. The method of claim 2, wherein the glial cells are astrocytes and said administering is carried out under conditions effective to restore astrocyte $K^+$ homeostasis.

5. The method of claim 2, wherein the selected human subject has or is at risk of having a neuropsychiatric disorder.

6. The method of claim 5, wherein the neuropsychiatric disorder is selected from the group consisting of schizophrenia, autism spectrum disorder, and bipolar disorder.

7. The method of claim 2, wherein said administering is carried out under conditions effective to decrease neuronal excitability in said human subject.

8. The method of claim 2, wherein said administering is carried out under conditions effective to decrease seizure incidence in said human subject.

9. The method of claim 2, wherein the delivery vehicle comprises a viral vector.

10. A method of treating a neuropsychiatric disorder in a human subject, said method comprising:

selecting a human subject having decreased glial cell $K^+$ uptake and the neuropsychiatric disorder, and administering, to the human subject, an inhibitor of REST selective gene expression under conditions effective to treat the neuropsychiatric disorder in the human subject, wherein the inhibitor comprises an inhibitory nucleic acid molecule selected from the group consisting of a REST antisense oligonucleotide, a REST shRNA, and a REST siRNA, and wherein the neuropsychiatric disorder is selected from the group consisting of schizophrenia, autism spectrum disorder, and bipolar disorder.

11. The method of claim 10, wherein the inhibitor is packaged in a delivery vehicle.

12. The method of claim 11, wherein the delivery vehicle comprises a glial cell targeting moiety.

13. The method of claim 11, wherein the delivery vehicle comprises a viral vector.

14. The method of claim 10, wherein said administering is carried out under conditions effective to decrease neuronal excitability in said subject.

15. The method of claim 10, wherein said administering is carried out under conditions effective to decrease seizure incidence in said human subject.

* * * * *

SEQUENCE LISTING

```
<160> NUMBER OF SEQ ID NOS: 21

<210> SEQ ID NO 1
<211> LENGTH: 1097
<212> TYPE: PRT
<213> ORGANISM: Homosapien

<400> SEQUENCE: 1

Met Ala Thr Gln Val Met Gly Gln Ser Ser Gly Gly Gly Gly Leu Phe
1               5                   10                  15

Thr Ser Ser Gly Asn Ile Gly Met Ala Leu Pro Asn Asp Met Tyr Asp
            20                  25                  30

Leu His Asp Leu Ser Lys Ala Glu Leu Ala Ala Pro Gln Leu Ile Met
        35                  40                  45

Leu Ala Asn Val Ala Leu Thr Gly Glu Val Asn Gly Ser Cys Cys Asp
```

-continued

```
    50                  55                  60

Tyr Leu Val Gly Glu Glu Arg Gln Met Ala Glu Leu Met Pro Val Gly
65                  70                  75                  80

Asp Asn Asn Phe Ser Asp Ser Glu Glu Gly Glu Gly Leu Glu Glu Ser
                85                  90                  95

Ala Asp Ile Lys Gly Glu Pro His Gly Leu Glu Asn Met Glu Leu Arg
            100                 105                 110

Ser Leu Glu Leu Ser Val Val Glu Pro Gln Pro Val Phe Glu Ala Ser
        115                 120                 125

Gly Ala Pro Asp Ile Tyr Ser Ser Asn Lys Asp Leu Pro Pro Glu Thr
    130                 135                 140

Pro Gly Ala Glu Asp Lys Gly Lys Ser Ser Lys Thr Lys Pro Phe Arg
145                 150                 155                 160

Cys Lys Pro Cys Gln Tyr Glu Ala Glu Ser Glu Glu Gln Phe Val His
                165                 170                 175

His Ile Arg Val His Ser Ala Lys Lys Phe Phe Val Glu Glu Ser Ala
            180                 185                 190

Glu Lys Gln Ala Lys Ala Arg Glu Ser Gly Ser Ser Thr Ala Glu Glu
        195                 200                 205

Gly Asp Phe Ser Lys Gly Pro Ile Arg Cys Asp Arg Cys Gly Tyr Asn
    210                 215                 220

Thr Asn Arg Tyr Asp His Tyr Thr Ala His Leu Lys His His Thr Arg
225                 230                 235                 240

Ala Gly Asp Asn Glu Arg Val Tyr Lys Cys Ile Ile Cys Thr Tyr Thr
                245                 250                 255

Thr Val Ser Glu Tyr His Trp Arg Lys His Leu Arg Asn His Phe Pro
            260                 265                 270

Arg Lys Val Tyr Thr Cys Gly Lys Cys Asn Tyr Phe Ser Asp Arg Lys
        275                 280                 285

Asn Asn Tyr Val Gln His Val Arg Thr His Thr Gly Glu Arg Pro Tyr
    290                 295                 300

Lys Cys Glu Leu Cys Pro Tyr Ser Ser Ser Gln Lys Thr His Leu Thr
305                 310                 315                 320

Arg His Met Arg Thr His Ser Gly Glu Lys Pro Phe Lys Cys Asp Gln
                325                 330                 335

Cys Ser Tyr Val Ala Ser Asn Gln His Glu Val Thr Arg His Ala Arg
            340                 345                 350

Gln Val His Asn Gly Pro Lys Pro Leu Asn Cys Pro His Cys Asp Tyr
        355                 360                 365

Lys Thr Ala Asp Arg Ser Asn Phe Lys Lys His Val Glu Leu His Val
    370                 375                 380

Asn Pro Arg Gln Phe Asn Cys Pro Val Cys Asp Tyr Ala Ala Ser Lys
385                 390                 395                 400

Lys Cys Asn Leu Gln Tyr His Phe Lys Ser Lys His Pro Thr Cys Pro
                405                 410                 415

Asn Lys Thr Met Asp Val Ser Lys Val Lys Leu Lys Lys Thr Lys Lys
            420                 425                 430

Arg Glu Ala Asp Leu Pro Asp Asn Ile Thr Asn Glu Lys Thr Glu Ile
        435                 440                 445

Glu Gln Thr Lys Ile Lys Gly Asp Val Ala Gly Lys Lys Asn Glu Lys
    450                 455                 460

Ser Val Lys Ala Glu Lys Arg Asp Val Ser Lys Glu Lys Lys Pro Ser
465                 470                 475                 480
```

-continued

```
Asn Asn Val Ser Val Ile Gln Val Thr Thr Arg Thr Arg Lys Ser Val
                485                 490                 495

Thr Glu Val Lys Glu Met Asp Val His Thr Gly Ser Asn Ser Glu Lys
            500                 505                 510

Phe Ser Lys Thr Lys Lys Ser Lys Arg Lys Leu Glu Val Asp Ser His
        515                 520                 525

Ser Leu His Gly Pro Val Asn Asp Glu Glu Ser Ser Thr Lys Lys Lys
    530                 535                 540

Lys Lys Val Glu Ser Lys Ser Lys Asn Asn Ser Gln Glu Val Pro Lys
545                 550                 555                 560

Gly Asp Ser Lys Val Glu Glu Asn Lys Lys Gln Asn Thr Cys Met Lys
                565                 570                 575

Lys Ser Thr Lys Lys Lys Thr Leu Lys Asn Lys Ser Ser Lys Lys Ser
            580                 585                 590

Ser Lys Pro Pro Gln Lys Glu Pro Val Glu Lys Gly Ser Ala Gln Met
        595                 600                 605

Asp Pro Pro Gln Met Gly Pro Ala Pro Thr Glu Ala Val Gln Lys Gly
    610                 615                 620

Pro Val Gln Val Glu Pro Pro Pro Pro Met Glu His Ala Gln Met Glu
625                 630                 635                 640

Gly Ala Gln Ile Arg Pro Ala Pro Asp Glu Pro Val Gln Met Glu Val
                645                 650                 655

Val Gln Glu Gly Pro Ala Gln Lys Glu Leu Leu Pro Pro Val Glu Pro
            660                 665                 670

Ala Gln Met Val Gly Ala Gln Ile Val Leu Ala His Met Glu Leu Pro
        675                 680                 685

Pro Pro Met Glu Thr Ala Gln Thr Glu Val Ala Gln Met Gly Pro Ala
    690                 695                 700

Pro Met Glu Pro Ala Gln Met Glu Val Ala Gln Val Glu Ser Ala Pro
705                 710                 715                 720

Met Gln Val Val Gln Lys Glu Pro Val Gln Met Glu Leu Ser Pro Pro
                725                 730                 735

Met Glu Val Val Gln Lys Glu Pro Val Gln Ile Glu Leu Ser Pro Pro
            740                 745                 750

Met Glu Val Val Gln Lys Glu Pro Val Lys Ile Glu Leu Ser Pro Pro
        755                 760                 765

Ile Glu Val Val Gln Lys Glu Pro Val Gln Met Glu Leu Ser Pro Pro
    770                 775                 780

Met Gly Val Val Gln Lys Glu Pro Ala Gln Arg Glu Pro Pro Pro Pro
785                 790                 795                 800

Arg Glu Pro Pro Leu His Met Glu Pro Ile Ser Lys Lys Pro Pro Leu
                805                 810                 815

Arg Lys Asp Lys Lys Glu Lys Ser Asn Met Gln Ser Glu Arg Ala Arg
            820                 825                 830

Lys Glu Gln Val Leu Ile Glu Val Gly Leu Val Pro Val Lys Asp Ser
        835                 840                 845

Trp Leu Leu Lys Glu Ser Val Ser Thr Glu Asp Leu Ser Pro Pro Ser
    850                 855                 860

Pro Pro Leu Pro Lys Glu Asn Leu Arg Glu Glu Ala Ser Gly Asp Gln
865                 870                 875                 880

Lys Leu Leu Asn Thr Gly Glu Gly Asn Lys Glu Ala Pro Leu Gln Lys
                885                 890                 895
```

```
Val Gly Ala Glu Glu Ala Asp Glu Ser Leu Pro Gly Leu Ala Ala Asn
            900                 905                 910

Ile Asn Glu Ser Thr His Ile Ser Ser Ser Gly Gln Asn Leu Asn Thr
        915                 920                 925

Pro Glu Gly Glu Thr Leu Asn Gly Lys His Gln Thr Asp Ser Ile Val
    930                 935                 940

Cys Glu Met Lys Met Asp Thr Asp Gln Asn Thr Arg Glu Asn Leu Thr
945                 950                 955                 960

Gly Ile Asn Ser Thr Val Glu Glu Pro Val Ser Pro Met Leu Pro Pro
                965                 970                 975

Ser Ala Val Glu Glu Arg Glu Ala Val Ser Lys Thr Ala Leu Ala Ser
            980                 985                 990

Pro Pro Ala Thr Met Ala Ala Asn  Glu Ser Gln Glu Ile  Asp Glu Asp
        995                 1000                1005

Glu Gly  Ile His Ser His Glu  Gly Ser Asp Leu Ser  Asp Asn Met
    1010                 1015                 1020

Ser Glu  Gly Ser Asp Asp Ser  Gly Leu His Gly Ala  Arg Pro Val
    1025                 1030                 1035

Pro Gln  Glu Ser Ser Arg Lys  Asn Ala Lys Glu Ala  Leu Ala Val
    1040                 1045                 1050

Lys Ala  Ala Lys Gly Asp Phe  Val Cys Ile Phe Cys  Asp Arg Ser
    1055                 1060                 1065

Phe Arg  Lys Gly Lys Asp Tyr  Ser Lys His Leu Asn  Arg His Leu
    1070                 1075                 1080

Val Asn  Val Tyr Tyr Leu Glu  Glu Ala Ala Gln Gly  Gln Glu
    1085                 1090                 1095
```

<210> SEQ ID NO 2
<211> LENGTH: 7333
<212> TYPE: DNA
<213> ORGANISM: Homosapien

<400> SEQUENCE: 2

```
ggcggcggcg gcggcgcgga ctgggtgcgc ggcgcagcgt cctgtgttgg aatgtgcggc     60

tgccgcgagc tcgcggcgca gcagcggagc gagcgccgcc gaggcccggg gccccagacc    120

ctggcggcgg ctgccgcagc cgagacggca gggcgaggcc cggaggcctg agcaccctct    180

gcagccccac tcctgggcct tcttggtcca cgacggcccc agcacccaac tttaccaccc    240

tcccccacct ctcccccgaa actccagcaa caaagaaaag tagtcggaga aggagcggcg    300

actcagggtc gcccgcccct cctcaccgag gaaggccgaa tacagttatg gccacccagg    360

taatggggca gtcttctgga ggaggagggc tgtttaccag cagtggcaac attggaatgg    420

ccctgcctaa cgacatgtat gacttgcatg acctttccaa agctgaactg gccgcacctc    480

agcttattat gctggcaaat gtggccttaa ctggggaagt aaatggcagc tgctgtgatt    540

acctggtcgg tgaagaaaga cagatggcag aactgatgcc ggttggggat aacaactttt    600

cagatagtga agaaggagaa ggacttgaag agtctgctga tataaaaggt gaacctcatg    660

gactggaaaa catggaactg agaagtttgg aactcagcgt cgtagaacct cagcctgtat    720

ttgaggcatc aggtgctcca gatatttaca gttcaaataa agatcttccc cctgaaacac    780

ctggagcgga ggacaaaggc aagagctcga agaccaaacc ctttcgctgt aagccatgcc    840

aatatgaagc agaatctgaa gaacagtttg tgcatcacat cagagttcac agtgctaaga    900

aatttttgt ggaagagagt gcagagaagc aggcaaaagc cagggaatct ggctcttcca    960
```

-continued

```
ctgcagaaga gggagatttc tccaagggcc ccattcgctg tgaccgctgc ggctacaata   1020
ctaatcgata tgatcactat acagcacacc tgaaacacca caccagagct ggggataatg   1080
agcgagtcta caagtgtatc atttgcacat acacaacagt gagcgagtat cactggagga   1140
aacatttaag aaaccatttt ccaaggaaag tatacacatg tggaaaatgc aactattttt   1200
cagacagaaa aaacaattat gttcagcatg ttagaactca tacaggagaa cgcccatata   1260
aatgtgaact ttgtccttac tcaagttctc agaagactca tctaactaga catatgcgta   1320
ctcattcagg tgagaagcca tttaaatgtg atcagtgcag ttatgtggcc tctaatcaac   1380
atgaagtaac ccgccatgca agacaggttc acaatgggcc taaacctctt aattgcccac   1440
actgtgatta caaaacagca gatagaagca acttcaaaaa acatgtagag ctacatgtga   1500
acccacggca gttcaattgc cctgtatgtg actatgcagc ttccaagaag tgtaatctac   1560
agtatcactt caaatctaag catcctactt gtcctaataa aacaatggat gtctcaaaag   1620
tgaaactaaa gaaaaccaaa aaacgagagg ctgacttgcc tgataatatt accaatgaaa   1680
aaacagaaat agaacaaaca aaaataaaag gggatgtggc tggaaagaaa aatgaaaagt   1740
ccgtcaaagc agagaaaaga gatgtctcaa aagagaaaaa gccttctaat aatgtgtcag   1800
tgatccaggt gactaccaga actcgaaaat cagtaacaga ggtgaaagag atggatgtgc   1860
atacaggaag caattcagaa aaattcagta aaactaagaa aagcaaaagg aagctggaag   1920
ttgacagcca ttctttacat ggtcctgtga atgatgagga atcttcaaca aaaaagaaaa   1980
agaaggtaga aagcaaatcc aaaaataata gtcaggaagt gccaaagggt gacagcaaag   2040
tggaggagaa taaaaagcaa aatacttgca tgaaaaaaag tacaaagaag aaaactctga   2100
aaaataaatc aagtaagaaa agcagtaagc ctcctcagaa ggaacctgtt gagaagggat   2160
ctgctcagat ggaccctcct cagatggggc ctgctcccac agaggcggtt cagaaggggc   2220
ccgttcaggt ggagccgcca cctcccatgg agcatgctca gatggagggt gcccagatac   2280
ggcctgctcc tgacgagcct gttcagatgg aggtggttca ggaggggcct gctcagaagg   2340
agctgctgcc tcccgtggag cctgctcaga tggtgggtgc ccaaattgta cttgctcaca   2400
tggagctgcc tcctcccatg gagactgctc agacggaggt tgcccaaatg ggccctgctc   2460
ccatggaacc tgctcagatg gaggttgccc aggtagaatc tgctcccatg caggtggtcc   2520
agaaggagcc tgttcagatg gagctgtctc ctcccatgga ggtggtccag aaggagcctg   2580
ttcagataga gctgtctcct cccatggagg tggtccagaa ggaacctgtt aagatagagc   2640
tgtctcctcc catagaggtg gtccagaagg agcctgttca gatggagttg tctcctccca   2700
tgggggtggt tcagaaggag cctgctcaga gggagccacc tcctcccaga gagcctcccc   2760
ttcacatgga gccaatttcc aaaaagcctc ctctccgaaa agataaaaag gaaaagtcta   2820
acatgcagag tgaaagggca cggaaggagc aagtccttat tgaagttggc ttagtgcctg   2880
ttaaagatag ctggcttcta aaggaaagtg taagcacaga ggatctctca ccaccatcac   2940
caccactgcc aaaggaaaat ttaagagaag aggcatcagg agaccaaaaa ttactcaaca   3000
caggtgaagg aaataaagaa gcccctcttc agaaagtagg agcagaagag gcagatgaga   3060
gcctacctgg tcttgctgct aatatcaacg aatctaccca tatttcatcc tctggacaaa   3120
acttgaatac gccagagggt gaaactttaa atggtaaaca tcagactgac agtatagttt   3180
gtgaaatgaa aatggacact gatcagaaca caagagagaa tctcactggt ataaattcaa   3240
cagttgaaga accagtttca ccaatgcttc ccccttcagc agtagaagaa cgtgaagcag   3300
tgtccaaaac tgcactggca tcacctcctg ctacaatggc agcaaatgag tctcaggaaa   3360
```

-continued

```
ttgatgaaga tgaaggcatc cacagccatg aaggaagtga cctaagtgac aacatgtcag   3420
agggtagtga tgattctgga ttgcatgggg ctcggccagt tccacaagaa tctagcagaa   3480
aaaatgcaaa ggaagccttg gcagtcaaag cggctaaggg agatttttgtt tgtatcttct   3540
gtgatcgttc tttcagaaag ggaaaagatt acagcaaaca cctcaatcgc catttggtta   3600
atgtgtacta tcttgaagaa gcagctcaag ggcaggagta atgaaacttt gaacaaggtt   3660
tcagttctta gtttgtaagg tatattacat tttatattca tttatgatag cagacaacct   3720
tttaagattg ctttaattag tatctgatgt tgatttttaa gtggcattct tttccttagg   3780
actttttatg tatacctgtt gattgttgtg taaattttag taaatctaag agagtgtact   3840
aaaccagcag gtatctgtta gcttatgtgt ttaattgaaa ttagaaggct aagatggtat   3900
aacagcattt tattgctttg tccagctaca acttgtcatt tttttctcca tgtcttatct   3960
tcctgtttca ctttagttta ttcttcgttt tttattgaga tctataaaaa attggcttac   4020
ttaatagcaa attacttgaa gaatttgcct gctttatata aagttagcac tttaagattt   4080
tttttttag agatgagaag acatttaaat tgaagaaaaa ttcccccagc aatagacagt   4140
ctatcagtcc aagtatttac ttcctgagtt ttgatcaata ttttttattt gtgtatgtta   4200
atcgtcataa aaacagtgat tttggtgtgt tttttatttt ggtgctttaa tggcttaaga   4260
tgttgcacat tttttttttc ttttggtttc tgtttatgtt tttttgccta tgcagttaaa   4320
tttttcctag aaatagcatt tgtgttgaac agtaacactt tatacatata tatatgcatg   4380
tttattttgt ttggcgtctt tggagggatg cttttagact tgtttgcaaa agggcagttt   4440
tctttttctt tgctgcagtt gtctattttg cagaataata gtgtgtgcaa gtttgtgagc   4500
aaatgaaata tgcaggttca atctattgat tttgattttt acatcttata tctatgccag   4560
aatctgtatt tcatataact tatttatttc gaatggatgt agtaaattca cagctatcag   4620
ttttgatttt gcaataaata aaccactagg ttgcatgtcg aacaaatttt tatctcaaat   4680
accaaccatc agtttttttt ttcatgtgtt ttggtacagc taattcctaa ttgtagagtg   4740
ttaaatgttt gaggagaacc ttttctcata gatggttggt gttcatatgg ctactttaca   4800
ataaagagaa ctgtaagtga tatttggaaa ctacaaacct ggaattagga gatataatta   4860
ttccttcaag ttttatagaa tatcacttgg gagattccaa agccatagct attacgcggc   4920
aaacctagga taagaaaggt agtatgagtg ctggtagacc agctgcaact ttcctataca   4980
gtgaaaaagg ctggtgaaac aagtacagtc cagatttttt aaaatcatac tttctcaggg   5040
atctccacaa actggtgggt gtcctggctg tctgtgtgat agcctctttc tataggtgag   5100
gcctcaaatg aattgcagct atcctggtgt tcctatgagg gcactttgta tgaaaaaggg   5160
catgtactcc aaaacatttt tgtaggttct ttggccagtt gccaaagagt gtgaaagaat   5220
ccaatagagg atttttctta ctgatagcag tcattcattg cagtaaaata aaatatgatc   5280
ccattaggga atcttgaatt ctgacctccc atactccgtt ttgaaataac cactttatat   5340
ttcatttttt aaaaatctga tgatctcttt gaggcaggtt tcagatttgg cagtacaaca   5400
tgaaagatta ggaaaagcat taataacgtg tgggtggaaa gcttgttaaa aatctgagag   5460
tgaagtttga gttaaaagtt gtttgaacat ggcattgact gggaggccaa agatttaaag   5520
aagcggaaga ttcttctctt aagacatgag gagtaagttg tgtgataatg gtatgtgttt   5580
tgtgtgcatg aatggacatt gtaaatgttg aattctaggc tccgacaatc attgtcaaca   5640
gaagatcaag ctgcaaatat ttatgtttta aaacttaaat tataaagcta gttaagtctt   5700
```

-continued

```
tctaatgact agttttaatg ttcatgggta cattttacct aagttaccgt ttacattgta   5760

tagaaaaaga tacatcttaa gcacagattg gttattagga attagtttgg ggaagaggtt   5820

tttttgtgga ttctttcata ctgcaaagaa aaaccatttg ccttttgggg aattgagcta   5880

acttctaatc tagtcttaag actagaatgc taaaaacaaa aacatgaagg aaattaaaac   5940

cccttattat taaattgatt tgtaaaaaca ttgttactgg aaatttattg gacttgaggc   6000

cttcctccag aaaataagga cttgattgtc aggcctatat taggttctga accttaatgc   6060

catgtatttg tacttactaa aaattgtttc aatgaaaagt acattagcag tatgaacttc   6120

tggtccagtt ggaagttttt ccatttgaaa aatgtgatgt ttgcatggaa ctgtttgaaa   6180

ctttttattt ttctagtccc cctcccccac actggataga atttagccta gaattttccc   6240

tttggataaa agaacaaaaa ttgaacatgt tatttgtaaa ttgatgttta gtaattagtg   6300

ataaacttga aatactagca tatattataa gccttaatct taggtagtct tatgaaaatg   6360

aatctcttaa ctatcttttg aacctgtatt cacattggtt ttcaagatat tttaagttat   6420

atttttcct cttttcagag ctgcttctta ttctggggct acttttttt ttagttgtgt   6480

aattcacaaa gggctgcatt ttttttttt tttaataagg cttataacta tggctggatc   6540

ttttgctcta gtcttctaag aagggccatt ttatttttta gagtcacttc taaagtcatg   6600

tggtaattaa ctttggagac tgttttgcgt atgagtgctg atacaaatta aaacccaagt   6660

agacctcatt gcatgtcacc ctatgaatgt tgacaatgga aggaatacct tgcctgtagt   6720

atactgtcac ttctggattg ataagctgag gaagaaagtt aagtttcttt tttacataag   6780

tcagaaaaac ttacagctgg tgttcctagt ttcctggttg acctcagcag atgaagtgaa   6840

cagatagtgt taattcagat tgaagaaatt atctgaatct tggtttgtgt agatttacaa   6900

tctacatgca atattaacta aatcagatag cttttacagt ttcacatgtg tacataggtt   6960

ccctcccggt cccttccata tccattagtt attgaacttt ctaaactggc attgaaacat   7020

tacaacaatg ttttgttgca ccaattttat aaacttaagc agtgcaatac gtgttacttt   7080

tctgaggcaa accaaaggta aatttctcaa ggttcttgct gccttcttta gcagcattg   7140

atggaagatc ttttatacat ttgtaataga taaaaataaa ccagattgca aatccttttt   7200

taaaatccta aaccatgtac caagtttttg gtccaaatta tgtaggataa gttaaactta   7260

aattgcattc tattaaccaa tatgagtgta tttctgtaag catagttatg ttgaaataaa   7320

gttttaaaaa cca                                                     7333
```

<210> SEQ ID NO 3
<211> LENGTH: 21
<212> TYPE: RNA
<213> ORGANISM: Artificial
<220> FEATURE:
<223> OTHER INFORMATION: REST siRNA

<400> SEQUENCE: 3

```
ccauuccaau guugccacug c                                              21
```

<210> SEQ ID NO 4
<211> LENGTH: 21
<212> TYPE: DNA
<213> ORGANISM: Homosapien

<400> SEQUENCE: 4

```
gcagtggcaa cattggaatg g                                              21
```

-continued

<210> SEQ ID NO 5
<211> LENGTH: 19
<212> TYPE: RNA
<213> ORGANISM: Artificial
<220> FEATURE:
<223> OTHER INFORMATION: REST siRNA

<400> SEQUENCE: 5
ucgauuagua uuguagccg 19

<210> SEQ ID NO 6
<211> LENGTH: 19
<212> TYPE: DNA
<213> ORGANISM: Homosapien

<400> SEQUENCE: 6
cggctacaat actaatcga 19

<210> SEQ ID NO 7
<211> LENGTH: 21
<212> TYPE: RNA
<213> ORGANISM: Artificial
<220> FEATURE:
<223> OTHER INFORMATION: REST RNA aptamer

<400> SEQUENCE: 7
uucagcacca cggacagcgc c 21

<210> SEQ ID NO 8
<211> LENGTH: 21
<212> TYPE: RNA
<213> ORGANISM: Artificial
<220> FEATURE:
<223> OTHER INFORMATION: REST RNA aptamer

<400> SEQUENCE: 8
aagucguggu gccugucgcg g 21

<210> SEQ ID NO 9
<211> LENGTH: 20
<212> TYPE: DNA
<213> ORGANISM: Artificial
<220> FEATURE:
<223> OTHER INFORMATION: primers

<400> SEQUENCE: 9
ctggataccg cagctaggaa 20

<210> SEQ ID NO 10
<211> LENGTH: 20
<212> TYPE: DNA
<213> ORGANISM: Artificial
<220> FEATURE:
<223> OTHER INFORMATION: primers

<400> SEQUENCE: 10
ccctcttaat catggcctca 20

<210> SEQ ID NO 11
<211> LENGTH: 17
<212> TYPE: DNA
<213> ORGANISM: Artificial
<220> FEATURE:
<223> OTHER INFORMATION: primers

<400> SEQUENCE: 11
tgcggccgat tgtgaac 17

<210> SEQ ID NO 12
<211> LENGTH: 21
<212> TYPE: DNA
<213> ORGANISM: Artificial
<220> FEATURE:
<223> OTHER INFORMATION: primers

<400> SEQUENCE: 12
cctcttttct ctgcggaacg t 21

<210> SEQ ID NO 13
<211> LENGTH: 20
<212> TYPE: DNA
<213> ORGANISM: Artificial
<220> FEATURE:
<223> OTHER INFORMATION: primers

<400> SEQUENCE: 13
gttatcctcg agggcatggt 20

<210> SEQ ID NO 14
<211> LENGTH: 20
<212> TYPE: DNA
<213> ORGANISM: Artificial
<220> FEATURE:
<223> OTHER INFORMATION: primers

<400> SEQUENCE: 14
cgtcctccag agtcagcact 20

<210> SEQ ID NO 15
<211> LENGTH: 22
<212> TYPE: DNA
<213> ORGANISM: Artificial
<220> FEATURE:
<223> OTHER INFORMATION: primers

<400> SEQUENCE: 15
aactgttaga cgacggacat ag 22

<210> SEQ ID NO 16
<211> LENGTH: 20
<212> TYPE: DNA
<213> ORGANISM: Artificial
<220> FEATURE:
<223> OTHER INFORMATION: primers

<400> SEQUENCE: 16
cttcggtctg gtgtccattt 20

<210> SEQ ID NO 17
<211> LENGTH: 22
<212> TYPE: DNA
<213> ORGANISM: Artificial
<220> FEATURE:
<223> OTHER INFORMATION: primers

<400> SEQUENCE: 17
tgaaccatcc aacgacaatc ta 22

<210> SEQ ID NO 18
<211> LENGTH: 21
<212> TYPE: DNA
<213> ORGANISM: Artificial

-continued

```
<220> FEATURE:
<223> OTHER INFORMATION: primers

<400> SEQUENCE: 18

cttgctgagg taccatgttc t                                               21


<210> SEQ ID NO 19
<211> LENGTH: 22
<212> TYPE: DNA
<213> ORGANISM: Artificial
<220> FEATURE:
<223> OTHER INFORMATION: primers

<400> SEQUENCE: 19

atgcgtactc attcaggtga ga                                              22


<210> SEQ ID NO 20
<211> LENGTH: 20
<212> TYPE: DNA
<213> ORGANISM: Artificial
<220> FEATURE:
<223> OTHER INFORMATION: primers

<400> SEQUENCE: 20

tgtgaacctg tcttgcatgg                                                 20


<210> SEQ ID NO 21
<211> LENGTH: 13
<212> TYPE: DNA
<213> ORGANISM: Artificial
<220> FEATURE:
<223> OTHER INFORMATION: primers
<220> FEATURE:
<221> NAME/KEY: misc_feature
<222> LOCATION: (3)..(4)
<223> OTHER INFORMATION: n is a, c, g, or t

<400> SEQUENCE: 21

ccnnggtgct gaa                                                        13
```